(12) United States Patent
Berka et al.

(10) Patent No.: US 7,413,882 B2
(45) Date of Patent: Aug. 19, 2008

(54) METHODS FOR DEGRADING OR CONVERTING PLANT CELL WALL POLYSACCHARIDES

(75) Inventors: Randy Berka, Davis, CA (US); Joel Cherry, Davis, CA (US)

(73) Assignee: Novozymes, Inc., Davis, CA (US)

(*) Notice: Subject to any disclaimer, the term of this patent is extended or adjusted under 35 U.S.C. 154(b) by 8 days.

(21) Appl. No.: 11/078,921

(22) Filed: Mar. 10, 2005

(65) Prior Publication Data
US 2005/0233423 A1  Oct. 20, 2005

Related U.S. Application Data

(60) Provisional application No. 60/556,779, filed on Mar. 25, 2004.

(51) Int. Cl.
C12P 19/02 (2006.01)
C12P 7/06 (2006.01)
C12P 21/06 (2006.01)
C12N 9/24 (2006.01)
C12N 7/00 (2006.01)
C12N 1/12 (2006.01)
D21C 3/00 (2006.01)

(52) U.S. Cl. .......... 435/105; 435/101; 435/99; 435/161; 435/69.1; 435/200; 435/235.1; 435/254.11; 435/254.6; 435/277

(58) Field of Classification Search ............... None
See application file for complete search history.

(56) References Cited

U.S. PATENT DOCUMENTS

| 5,597,728 | A | 1/1997 | Wyatt et al. |
| 2002/0037342 | A1 | 3/2002 | Labielle et al. |
| 2002/0159990 | A1* | 10/2002 | Ingram et al. ............ 424/94.61 |
| 2003/0044951 | A1 | 3/2003 | Sporleder et al. |
| 2003/0203454 | A1 | 10/2003 | Chotani et al. |

FOREIGN PATENT DOCUMENTS

| WO | WO 00/70729 A2 | 11/2000 |
| WO | WO 00/71729 A2 * | 11/2000 |
| WO | WO 02/095014 A2 * | 11/2002 |

OTHER PUBLICATIONS

Broun et al., Catalytic plasticity of fatty acid modification enzymes underlying chemical diversity of plant lipids. Science, 1998, vol. 282: 1315-1317.*
Witkowski et al., Conversion of b-ketoacyl synthase to a malonyl decarboxylase by replacemnt of the active-site cysteine with glutamine. Biochemistry, 1999, vol. 38: 11643-11650.*
Seffernick et al., Melamine deaminase and Atrazine chlorohydrolase: 98 percent identical but functionally different. J. Bacteriol.,2001, vol. 183 (8): 2405-2410.*
Salvador et al., Degradation of cell wall materials from sweetpotato, cassava, and potato by a bacterial protopectinase and terminal sugar analysis of the resulting solubilized products. *J. Biosci. Bioeng.*, 2002, vol. 93, pp. 67-72.
Carpita et al., *Plant Physiology*, Oct. 2001, vol. 127, pp. 551-565.
Fujita et al., Synergistic saccharification, and direct fermentation to ethanol, or amorphous cellulose by use of an engineered yeast strain codisplaying three types of cellulolytic enzyme. *Applied and Environmental Microbiology*, 2004, vol. 70, pp. 1207-1212.
Penttila et al., Efficient secretion of two fungal cellobiohydrolases by saccharomyces-cerevisiae, Gene, 1988, vol. 63, pp. 103-112.
Rensburg Van P et al., Engineering yeast for effcient cellulose degradation, Yeast, 1998, vol. 14, pp. 67-76.

* cited by examiner

*Primary Examiner*—Rebecca E. Prouty
*Assistant Examiner*—Ganapathirama Raghu
(74) *Attorney, Agent, or Firm*—Robert L. Stames

(57) ABSTRACT

The present invention relates to methods for converting plant cell wall polysaccharides into one or more products, comprising: treating the plant cell wall polysaccharides with an effective amount of a spent whole fermentation broth of a recombinant microorganism, wherein the recombinant microorganism expresses one or more heterologous genes encoding enzymes which degrade or convert the plant cell wall polysaccharides into the one or more products. The present invention also relates to methods for producing an organic substance, comprising: (a) saccharifying plant cell wall polysaccharides with an effective amount of a spent whole fermentation broth of a recombinant microorganism, wherein the recombinant microorganism expresses one or more heterologous genes encoding enzymes which degrade or convert the plant cell wall polysaccharides into saccharified material; (b) fermenting the saccharified material of step (a) with one or more fermenting microorganisms; and (c) recovering the organic substance from the fermentation.

9 Claims, 17 Drawing Sheets

Met Lys Leu Gly Trp Ile Glu Val Ala Ala Leu Ala Ala Ala Ser Val Val Ser Ala
ATG AAG CTT GGT TGG ATC GAG GTG GCC GCA TTG GCG GCT GCC CCT CAG TAG CAG TGC

Fig. 8

```
Met Arg Ser Ser Pro Leu Leu Arg Ser Ala Val Val Ala Ala Leu Pro Val Leu Ala
ATG CGT TCC TCC CCC CTC CTC CGC TCC GCC GTT GTG GCC GCC CTG CCG GTG TTG GCC

Leu Ala
CTT GCC
```

METHODS FOR DEGRADING OR CONVERTING PLANT CELL WALL POLYSACCHARIDES

CROSS-REFERENCE TO RELATED APPLICATION

This application claims the benefit of U.S. Provisional Application No. 60/556,779, filed Mar. 25, 2004, which application is incorporated herein by reference.

STATEMENT AS TO RIGHTS TO INVENTIONS MADE UNDER FEDERALLY SPONSORED RESEARCH AND DEVELOPMENT

This invention was made with Government support under NREL Subcontract No. ZCO-30017-02, Prime Contract DE-AC36-98GO10337 awarded by the Department of Energy. The government has certain rights in this invention.

BACKGROUND OF THE INVENTION

1. Field of the Invention

The present invention relates to methods for degrading or converting plant cell wall polysaccharides and to products obtained by such methods.

2. Description of the Related Art

Plant cell walls are composed of a mixture of polysaccharides interlocked in a complex structure (Carpita et al., 2001, *Plant Physiology* 127: 551-565). The mixture of polysaccharides include cellulose, xyloglycan (hemicellulose), and pectic polymers, which are primarily composed of hexoses, e.g., glucose, galactose, and mannose; pentoses, e.g., xylose and arabinose; uronic acids, e.g., galacturonic acid and glucuronic acid; and deoxyhexoses, e.g., rhamnose and fucose.

Plant cell wall polysaccharides can be enzymatically degraded to glucose, xylose, mannose, galactose, and arabinose, which can then be converted to other organic substances, for example, glucose is easily fermented by yeast into ethanol. Wood, agricultural residues, herbaceous crops, and municipal solid wastes can be used as sources of plant cell wall polysaccharides.

Cellulose is a primary component of plant cell walls. Many microorganisms produce enzymes that degrade cellulose. These enzymes include, for example, endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

Natural microorganisms that degrade cellulose and other cell wall polysaccharides may not be ideal for large-scale conversion of cellulosic materials because (a) the full complement of enzymes may be lacking, (b) one or more enzyme components perform poorly, are labile, or their kinetic behavior fails to meet the specification of the intended use, (c) the conversion and/or degradation could be improved by expression of a heterologous enzyme gene that enhances the conversion/degradation, or (d) the full complement of enzymes may be in insufficient amounts to be economically viable. It would be an advantage to the art to improve the degradation and conversion of plant cell wall polysaccharides by using whole fermentation broth from recombinant microorganisms to circumvent expensive cell removal and enzyme formulation steps.

It is an object of the present invention to provide new methods for degrading or converting plant cell wall polysaccharides into various products using spent whole fermentation broths from recombinant microorganisms.

SUMMARY OF THE INVENTION

The present invention relates to methods for degrading or converting plant cell wall polysaccharides into one or more products, comprising: treating the plant cell wall polysaccharides with an effective amount of a spent whole fermentation broth of a recombinant microorganism, wherein the recombinant microorganism expresses one or more heterologous genes encoding enzymes which degrade or convert the plant cell wall polysaccharides into the one or more products.

The present invention also relates to methods for producing one or more organic substances, comprising:

(a) saccharifying plant cell wall polysaccharides with an effective amount of a spent whole fermentation broth of a recombinant microorganism, wherein the recombinant microorganism expresses one or more heterologous genes encoding enzymes which degrade or convert the plant cell wall polysaccharides into saccharified material;

(b) fermenting the saccharified material of step (a) with one or more fermenting microoganisms; and (c) recovering the one or more organic substances from the fermentation.

The present invention further relates to products or organic substances obtained by such methods. In a preferred aspect, the organic substance is alcohol.

BRIEF DESCRIPTION OF THE FIGURES

FIG. 8 shows the DNA sequence (SEQ ID NO: 32) and deduced amino acid sequence (SEQ ID NO: 33) of the secretion signal sequence of an *Aspergillus oryzae* beta-glucosidase.
FIG. 9 shows the DNA sequence (SEQ ID NO: 36) and deduced amino acid sequence (SEQ ID NO: 37) of the secretion signal sequence of a *Humicola insolens* endoglucanase V.

SMA135-04 fermentation broth. *Trichoderma reesei* strain SMA135-04 expresses recombinant *Aspergillus oryzae* beta-glucosidase. Each profile is plotted as % RS yield (% of theoretical maximum reducing sugar based on the glucan composition of 10 mg of PCS per ml) as a function of hydrolysis time (1-120 hours). Enzyme doses are noted in the upper right of each panel.

Figure 15:
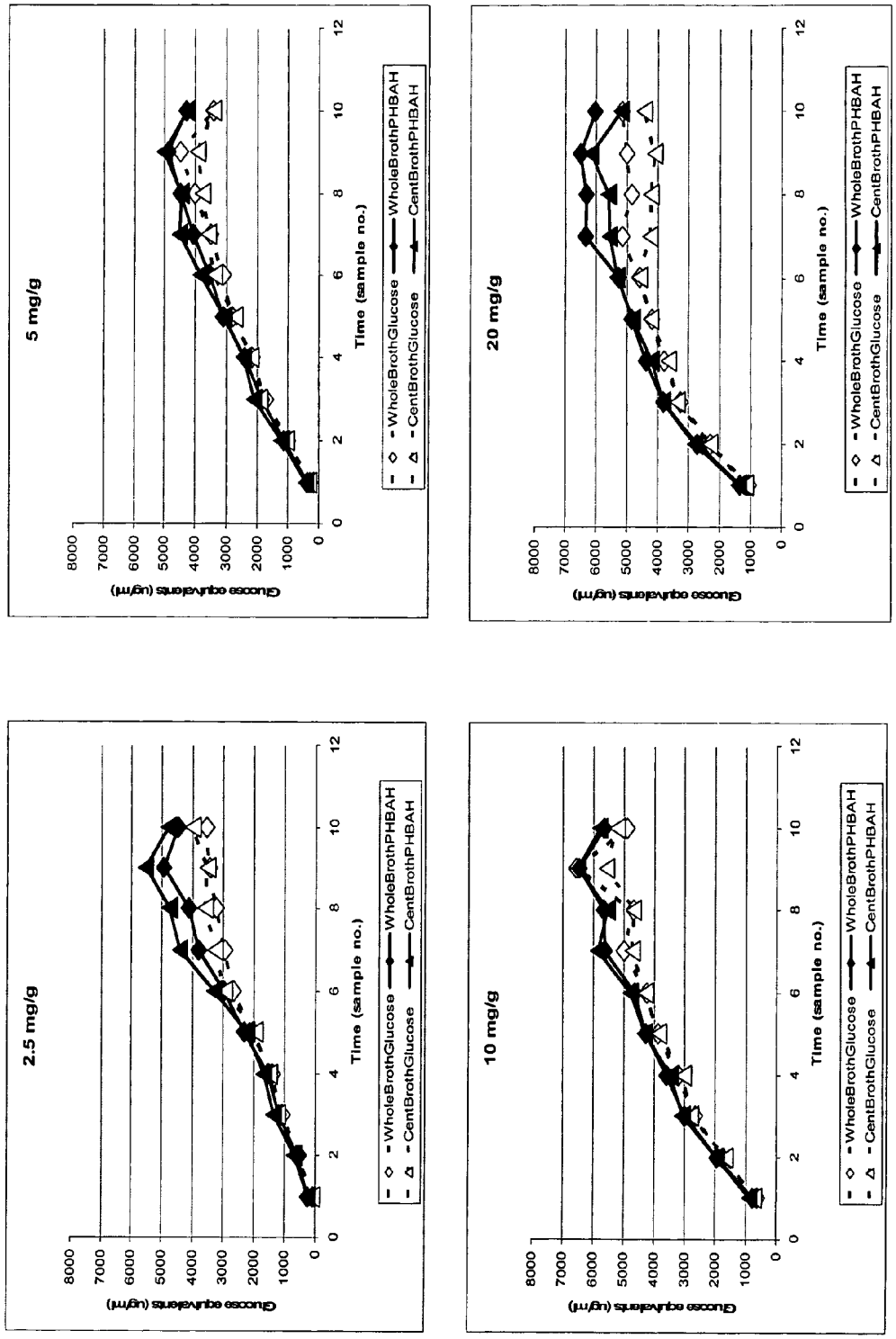

FIG. 15 shows a comparison of total reducing sugar (RS) and glucose liberated during PCS hydrolysis reactions using WB and CB samples from *Trichoderma reesei* SMA135-04 that harbors an expression vector directing synthesis and secretion of *Aspergillus oryzae* beta-glucosidase. Enzyme doses are noted at the top of each panel. The sample numbers noted on the X-axis correspond to hydrolysis times spanning 1 to 120 hours.

Figure 16:
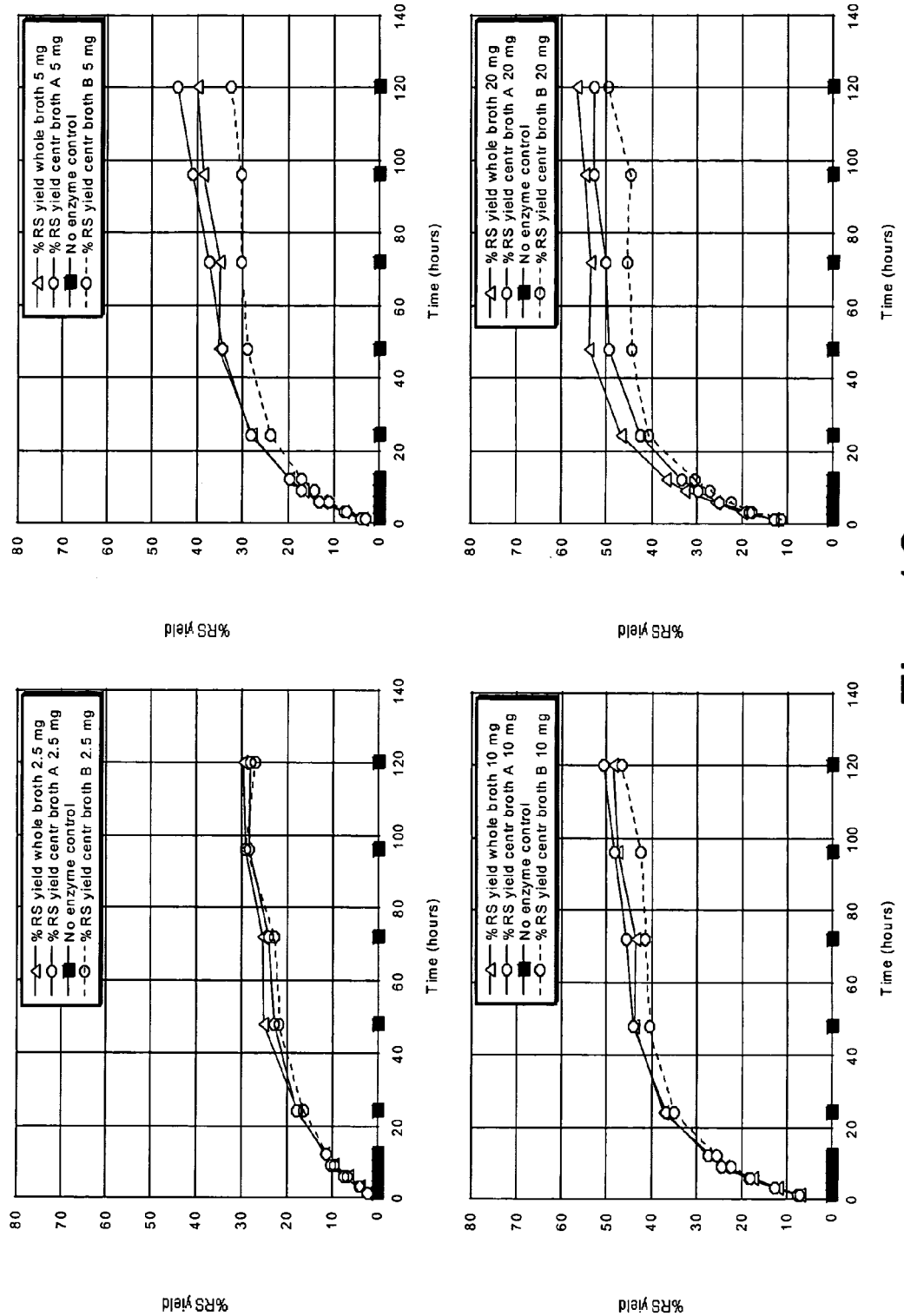

FIG. 16 shows the PCS hydrolysis curves for WB and CB samples derived from *Trichoderma reesei* RutC30 fermentation broth stored two weeks at 4° C. Each profile is plotted as % RS yield (% of theoretical maximum reducing sugar based on the glucan composition of 10 mg of PCS per ml) as a function of hydrolysis time (1-120 hours). Enzyme doses are noted in the upper right of each panel.

Figure 17:
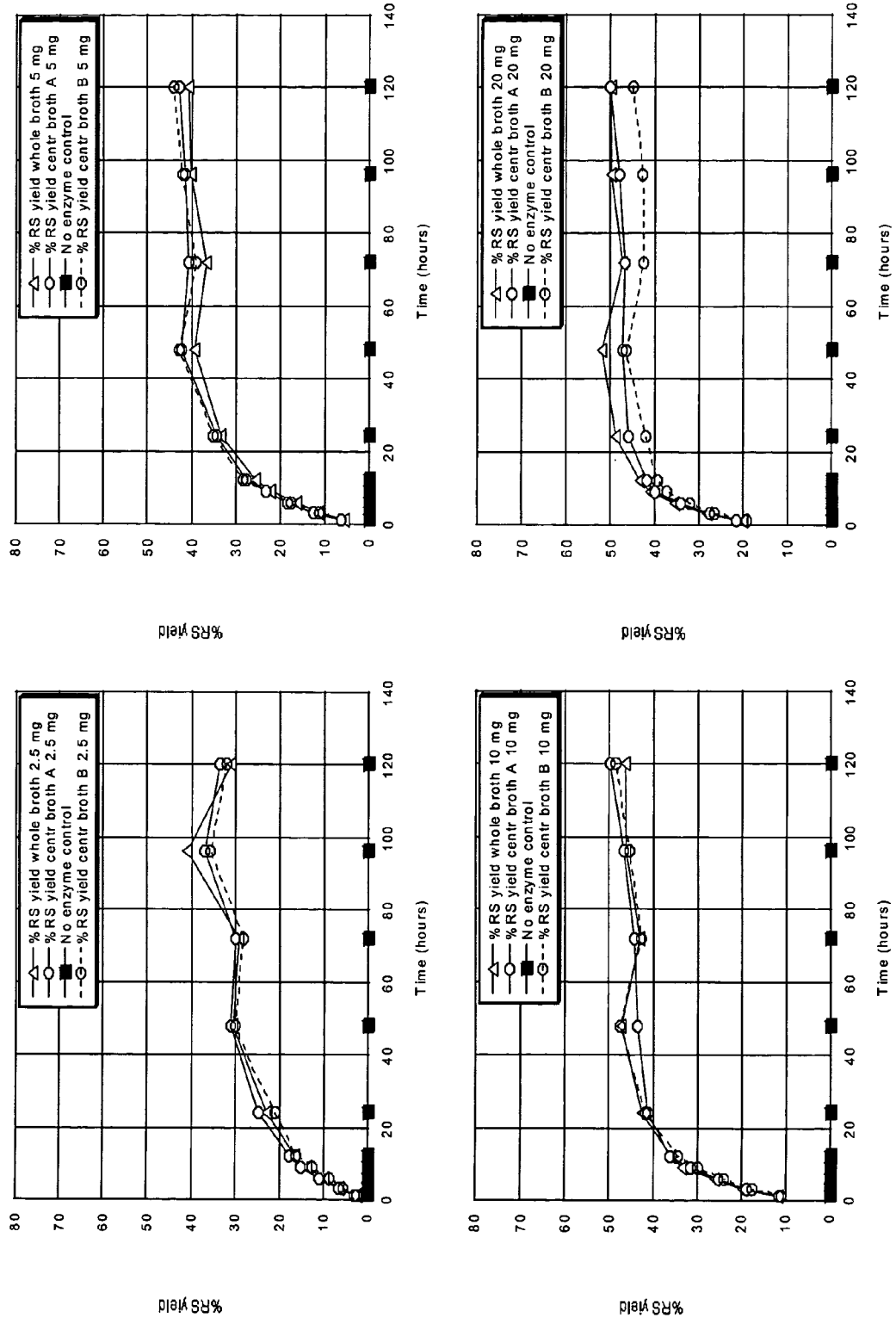

FIG. 17 shows the PCS hydrolysis curves for WB and CB samples derived from *Trichoderma reesei* SMA135-04 fermentation broth stored two weeks at 4° C. Each profile is plotted as % RS yield (% of theoretical maximum based on the glucan composition of 10 mg/ml PCS) as a function of hydrolysis time (1-120 hours). Enzyme doses are noted in the upper right of each panel.

DETAILED DESCRIPTION OF THE INVENTION

The present invention relates to methods for degrading or converting plant cell wall polysaccharides into one or more products, comprising: treating the plant cell wall polysaccharides with an effective amount of a spent whole fermentation broth of a recombinant microorganism, wherein the recombinant microorganism expresses one or more heterologous genes encoding enzymes which degrade or convert the plant cell wall polysaccharides into the one or more products. The present invention also relates to methods for producing one or more organic substances, comprising: (a) saccharifying plant cell wall polysaccharides with an effective amount of a spent whole fermentation broth of a recombinant microorganism, wherein the recombinant microorganism expresses one or more heterologous genes encoding enzymes which degrade or convert the plant cell wall polysaccharides into one or more products; (b) fermenting the saccharified material of step (a) with one or more fermenting microoganisms; and (c) recovering the one or more organic substances from the fermentation.

Plant Cell Wall Polysaccharides

In the methods of the present invention, the source of the plant cell wall polysaccharides can be any plant biomass containing cell wall polysaccharides. Such sources include, but are not limited to, herbaceous material, agricultural residues, forestry residues, municipal solid waste, waste paper, and pulp and paper mill residues.

In a preferred aspect, the plant cell wall biomass is corn stover. In another preferred aspect, the plant cell wall biomass is corn fiber. In another preferred aspect, the plant cell wall biomass is rice straw. In another preferred aspect, the plant cell wall biomass is paper and pulp processing waste. In another preferred aspect, the plant cell wall biomass is woody or herbaceous plants. In another preferred aspect, the plant cell wall biomass is fruit pulp. In another preferred aspect, the plant cell wall biomass is vegetable pulp. In another preferred aspect, the plant cell wall biomass is pumice. In another preferred aspect, the plant cell wall biomass is distillers grain.

The plant cell wall biomass may be used as is or may be subjected to pretreatment using conventional methods known in the art. Such pretreatments includes physical, chemical, and biological pretreatment. For example, physical pretreatment techniques can include various types of milling, crushing, irradiation, steaming/steam explosion, and hydrothermolysis. Chemical pretreatment techniques can include dilute acid, alkaline, organic solvent, ammonia, sulfur dioxide, carbon dioxide, and pH-controlled hydrothermolysis. Biological pretreatment techniques can involve applying lignin-solubilizing microorganisms (see, for example, Hsu, T.-A., 1996, Pretreatment of biomass, in *Handbook on Bio-ethanol: Production and Utilization*, Wyman, C. E., ed., Taylor & Francis, Washington, D.C., 179-212; Ghosh, P., Singh, A., 1993, Physicochemical and biological treatments for enzymatic/microbial conversion of lignocellulosic biomass, *Adv. Appl. Microbiol.*, 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson, L., and Hahn-Hagerdal, B., 1996, Fermentation of lignocellulosic hydrolysates for ethanol production, *Enz. Microb. Tech*, 18: 312-331; and Vallander, L., and Eriksson, K.-E. L., 1990, Production of ethanol from lignocellulosic materials: State of the art, *Adv. Biochem. Eng./Biotechnol.*, 42: 63-95).

In the present invention, the plant cell wall polysaccharides include, but are not limited to, cellulose, hemicellulose, and pectic substances.

Cellulose is composed of beta-1,4-glucan. Hemicellulose is composed of beta-1,3-1,4-glucan, xyloglucan, xylan (arabinoxylan), mannan (galactomannan), galactan (arabinogalactan), and arabinan. Pectic substances are composed of homogalacturonan (pectin), rhamnogalacturonan, and xylogalacturonan.

Beta-1,4-glucan is composed of beta-1,4-linked glucose. Enzymes that degrade beta-1,4-glucan include endoglucanase, cellobiohydrolase, and beta-glucosidase.

Beta-1,3-1,4-glucan is composed of beta-1,4-linked glucose interrupted by beta-1,3-linked glucose. Enzymes that degrade beta-1,3-1,4-glucan include endo-beta-1,3(4)-glucanase, endoglucanase (beta-glucanase, cellulase), and beta-glucosidase.

Xyloglucans are composed of beta-1,4-linked glucose with alpha-1,6-linked xylose substituents. Enzymes that degrade xyloglucans include xyloglucanase, endoglucanase, and cellulase.

Xylan (arabinoxylan) is composed of beta-1,4-linked xylose, with alpha-1,2 or alpha-1,3 linked arabinoses. The xylose can be acetylated. Glucuronic acid is also present. Enzymes that degrade xylan include xylanase, xylosidase, alpha-arabinofuranosidase, alpha-glucuronidase, and acetyl xylan esterase.

Mannan (galactomannan) is composed of beta-1,4-linked mannose with alpha-1,6-linked galactose substituents. The mannose substituents can also be acetylated. Enzymes that degrade mannan include mannanase, mannosidase, alpha-galactosidase, and mannan acetyl esterase.

Galactan (arabinogalactan) is composed of D-galactose and 3,6-anhydrogalactose linked by beta-1,3-linkages. Enzymes that degrade galactan include galactanases.

Arabinan is composed of 1,3-1,5-linked L-arabinose. Enzymes that degrade arabinan include arabinanases.

Homogalacturonan is composed of alpha-1,4-linked galacturonic acid. The galacturonic acid substituents may be acetylated and/or methylated. Enzymes that degrade homogalacturonan include pectate lyase, pectin lyase, pectate lyase, polygalacturonase, pectin acetyl esterase, and pectin methyl esterase.

Rhamnogalacturonan is composed of alternating alpha-1, 4-rhamnose and alpha-1,2-linked galacturonic acid, with side chains linked 1,4 to rhamnose. The side chains include Type I galactan, which is beta-1,4-linked galactose with alpha-1, 3-linked arabinose substituents; Type II galactan, which is beta-1,3-1,6-linked galactoses (very branched) with arabinose substituents; and arabinan, which is alpha-1,5-linked arabinose with alpha-1,3-linked arabinose branches. The galacturonic acid substituents may be acetylated and/or methylated. Enzymes that degrade rhamnogalacturonan include alpha-arabinofuranosidase, beta-galactosidase, galactanase, arabinanase, alpha-arabinofuranosidase, rhamnogalacturonase, rhamnogalacturonan lyase, and rhamnogalacturonan acetyl esterase.

Xylogalacturonan is composed of alpha-1,4-linked galacturonic acid with side chains of xylose. Galactose and fucose may be linked to the xylose substituents. Rhamnose is also present. The galacturonic acid substituents may be acetylated and/or methylated. Enzymes that degrade xylogalacturonan include xylogalacturonosidase, xylogalacturonase, and rhamnogalacturonan lyase.

Cellulose may also be present as lignocellulose. Lignin is composed of methoxylated phenyl-propane units linked by ether linkages and C—C bonds. The chemical composition of lignin differs according to the plant species. Such components include guaiacyl, 4-hydroxyphenyl, and syringyl groups. Enzymes that degrade the lignin component of lignocellulose include lignin peroxidases, manganese-dependent peroxidases, hybrid peroxidases, with combined properties of lignin peroxidases and manganese-dependent peroxidases, and laccases (Vicuna, 2000, *Molecular Biotechnology* 14: 173-176; Broda et al., 1996, *Molecular Microbiology* 19: 923-932).

Recombinant Microorganisms

In the methods of the present invention, the recombinant microorganism can be any microorganism that is useful as a host for the recombinant production of enzymes useful in the conversion or degradation of plant cell wall polysaccharides. The microorganism chosen as a host for recombinant production may already contain one or more native genes encoding enzymes that degrade or convert plant cell wall polysaccharides. However, the host may be deficient in the full complement of enzymes necessary to degrade or convert plant cell wall polysaccharides, i.e., the host may lack one or more genes. Alternatively, the host may contain the full complement of enzymes, but one or more enzymes may be poorly expressed. Moreover, the host may lack one or more genes required to produce the full complement of enzymes and one or more enzymes the host does produce may be poorly expressed. It will be understood in the present invention that a gene native to the host that has undergone manipulation, as described herein, will be considered a heterologous gene.

The host is preferably a fungal strain. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a preferred aspect, the fungal host is a yeast strain. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A.,. Passmore, S. M., and Davenport, R. R., eds, Soc. App. Bacteriol. Symposium Series No. 9, 1980).

In a more preferred aspect, the yeast host is a *Candida, Hansenula, Kluyveromyces, Pichia, Saccharomyces, Schizosaccharomyces*, or *Yarrowia* strain.

In a most preferred aspect, the yeast host is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* strain. In another most preferred aspect, the yeast host is a *Kluyveromyces lactis* strain. In another most preferred aspect, the yeast host is a *Yarrowia lipolytica* strain.

In another preferred aspect, the fungal host is a filamentous fungal strain. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In a more preferred aspect, the filamentous fungal host is, but not limited to, an *Acremonium, Aspergillus, Fusarium, Humicola, Mucor, Myceliophthora, Neurospora, Penicillium, Scytalidium, Thielavia, Tolypocladium*, or *Trichoderma* strain.

In an even more preferred aspect, the filamentous fungal host is an *Aspergillus awamori, Aspergillus foetidus, Aspergillus japonicus, Aspergillus nidulans, Aspergillus niger*, or *Aspergillus oryzae* strain. In another even more preferred aspect, the filamentous fungal host is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum* strain. In another even more preferred aspect, the filamentous fungal host is a *Humicola insolens, Humicola lanuginosa, Mucor miehei, Myceliophthora thermophila, Neurospora crassa, Penicillium purpurogenum, Scytalidium thermophilum*, or *Thielavia terrestris* strain. In a further even more preferred aspect, the filamentous fungal host is a *Trichoderma harzianum, Trichoderma koningii, Trichoderma longibrachiatum, Trichoderma reesei*, or *Trichoderma viride* strain.

In a most preferred aspect, the filamentous fungal host is *Trichoderma reesei* RutC30, which is available from the American Type Culture Collection as *Trichoderma reesei* ATCC 56765.

In a preferred aspect, the host or recombinant microorganism comprises one or more heterologous genes encoding enzymes selected from the group consisting of endoglucanase (cellulase), cellobiohydrolase, and beta-glucosidase.

In a more preferred aspect, the recombinant microorganism comprises a heterologous gene encoding an endoglucanase. In another more preferred aspect, the recombinant microorganism comprises a heterologous gene encoding a cellobiohydrolase gene. In another more preferred aspect, the recombinant microorganism comprises a heterologous gene encoding a beta-glucosidase.

In a most preferred aspect, the recombinant microorganism comprises heterologous genes encoding an endoglucanase and a cellobiohydrolase. In another most preferred aspect, the recombinant microorganism comprises heterologous genes encoding an endoglucanase and a beta-glucosidase.

In another most preferred aspect, the recombinant microorganism comprises heterologous genes encoding an endoglucanase, a cellobiohydrolase, and a beta-glucosidase.

In another preferred aspect, the recombinant microorganism further comprises a glucohydrolase.

In another preferred aspect, the recombinant microorganism further comprises one or more heterologous genes encoding enzymes selected from the group consisting of xyloglucanase, xylanase, xylosidase, alpha-arabinofuranosidase, alpha-glucuronidase, and acetyl xylan esterase.

In another preferred aspect, the recombinant microorganism further comprises one or more heterologous genes encoding enzymes selected from the group consisting of mannanase, mannosidase, alpha-galactosidase, mannan acetyl esterase, galactanase, and arabinanase.

In another preferred aspect, the recombinant microorganism further comprises one or more heterologous genes encoding enzymes selected from the group consisting of pectate lyase, pectin lyase, polygalacturonase, pectin acetyl esterase, pectin methyl esterase, alpha-arabinofuranosidase, beta-galactosidase, galactanase, arabinanase, alpha-arabinofuranosidase, rhamnogalacturonase, rhamnogalacturonan lyase, rhamnogalacturonan acetyl esterase, xylogalacturonosidase, xylogalacturonase, and rhamnogalacturonan lyase.

In another preferred aspect, the recombinant microorganism further comprises one or more heterologous genes encoding enzymes selected from the group consisting of a lignin peroxidase, manganese-dependent peroxidase, and hybrid peroxidase.

In another preferred aspect, the recombinant microorganism even further comprises one or more heterologous genes encoding enzymes selected from the group consisting of an esterase, lipase, oxidase, phospholipase, phytase, protease, and peroxidase.

A gene encoding a plant cell wall degrading or converting enzyme may be of fungal or bacterial origin, e.g., species of *Humicola, Coprinus, Thielavia, Fusarium, Myceliophthora, Acremonium, Cephalosporium, Scytalidium, Penicillium* or *Aspergillus* (see, for example, EP 458162), especially those selected from the species *Humicola insolens* (reclassified as *Scytalidium thermophilum*, see for example, U.S. Pat. No. 4,435,307), *Coprinus cinereus, Fusarium oxysporum, Myceliophthora thermophila, Meripilus giganteus, Thielavia terrestris, Acremonium* sp., *Acremonium persicinum, Acremonium acremonium, Acremonium brachypenium, Acremonium dichromosporum, Acremonium obclavatum, Acremonium pinkertoniae, Acremonium roseogriseum, Acremonium incoloratum,* and *Acremonium furatum*; preferably from the species *Humicola insolens* DSM 1800, *Fusarium oxysporum* DSM 2672, *Myceliophthora thermophila* CBS 117.65, *Cephalosporium* sp. RYM-202, *Acremonium* sp. CBS 478.94, *Acremonium* sp. CBS 265.95, *Acremonium persicinum* CBS 169.65, *Acremonium acremonium* AHU 9519, *Cephalosporium* sp. CBS 535.71, *Acremonium brachypenium* CBS 866.73, *Acremonium dichromosporum* CBS 683.73, *Acremonium obclavatum* CBS 311.74, *Acremonium pinkertoniae* CBS 157.70, *Acremonium roseogriseum* CBS 134.56, *Acremonium incoloratum* CBS 146.62, and *Acremonium furatum* CBS 299.70H. Plant cell wall hydrolytic enzyme genes may also be obtained from *Trichoderma* (particularly *Trichoderma viride, Trichoderma reesei,* and *Trichoderma koningii*), alkalophilic *Bacillus* (see, for example, U.S. Pat. No. 3,844,890 and EP 458162), and *Streptomyces* (see, for example, EP 458162).

The enzymes and genes thereof referenced herein may be obtained from any suitable origin, including, bacterial, fungal, yeast or mammalian origin. The term "obtained" as used herein in connection with a given source shall mean that the polypeptide encoded by a nucleotide sequence is produced by the source or by a strain in which the nucleotide sequence from the source has been inserted. Encompassed within the meaning of a native enzyme are natural variants or variants obtained, for example, by site-directed mutagenesis or shuffling.

Techniques used to isolate or clone a gene encoding an enzyme are known in the art and include isolation from genomic DNA, preparation from cDNA, or a combination thereof. The cloning of a gene from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleotide sequence-based amplification (NASBA) may be used.

Fungal cells may be transformed by a process involving protoplast formation, transformation of the protoplasts, and regeneration of the cell wall in a manner known per se. Suitable procedures for transformation of *Aspergillus* and *Trichoderma* host strains are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology,* Volume 194, pp 182-187, Academic Press, Inc., New York; Ito et al., 1983, *Journal of Bacteriology* 153: 163; and Hinnen et al., 1978, *Proceedings of the National Academy of Sciences USA* 75:1920.

Enzymes Having Plant Cell Wall Hydrolytic Activity and Genes Thereof

In the methods of the present invention, the recombinant microorganism comprises one or more genes which are heterologous or foreign to the microorganism, wherein the one or more genes encode enzymes involved in the degradation or conversion of plant cell wall polysaccharides.

The heterologous genes may encode enzymes that degrade beta-1,4-glucan such as endoglucanase (cellulase), cellobiohydrolase, glucohydrolase, and beta-glucosidase; degrade beta-1,3-1,4-glucan such as endo-beta-1,3(4)-glucanase, endoglucanase (beta-glucanase, cellulase), and beta-glucosidase; degrade xyloglucans such as xyloglucanase, endoglucanase, and cellulase; degrade xylan such as xylanase, xylosidase, alpha-arabinofuranosidase, alpha-glucuronidase, and acetyl xylan esterase; degrade mannan such as mannanase, mannosidase, alpha-galactosidase, and mannan acetyl esterase; degrade galactan such as galactanase; degrade arabinan such as arabinanase; degrade homogalacturonan such as pectate lyase, pectin lyase, pectate lyase, polygalacturonase, pectin acetyl esterase, and pectin methyl esterase; degrade rhamnogalacturonan such as alpha-arabinofuranosidase, beta-galactosidase, galactanase, arabinanase, alpha-arabinofuranosidase, rhamnogalacturonase, rhamnogalacturonan lyase, and rhamnogalacturonan acetyl esterase; degrade xylogalacturonan such as xylogalacturonosidase, xylogalacturonase, and rhamnogalacturonan lyase; and degrade lignin such as lignin peroxidases, manganese-dependent peroxidases, hybrid peroxidases, with combined properties of lignin peroxidases and manganese-dependent peroxidases, and laccases.

Genes encoding polysaccharide-degrading enzymes may be obtained from sources as described by B. Henrissat, 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696, which is incorporated herein by reference.

The recombinant microorganism may further comprise one or more heterologous genes encoding enzymes such as esterases, lipases, oxidases, phospholipases, phytases, proteases, and peroxidases.

The enzymes may have activity either in the acid, neutral, or alkaline pH-range. In a preferred aspect, the enzymes have activity in the pH range of about 2 to about 7.

Endoglucanases

The term "endoglucanase" is defined herein as an endo-1,4-(1,3;1,4)-beta-D-glucan 4-glucanohydrolase (E.C. No. 3.2.1.4) which catalyses endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. For purposes of the present invention, endoglucanase activity is determined using carboxymethyl cellulose (CMC) hydrolysis according to the procedure of Ghose, 1987, *Pure and Appl. Chem.* 59: 257-268.

In a preferred aspect, an endoglucanase gene is obtained from a *Trichoderma reesei* strain. In another preferred aspect, an endoglucanase gene is obtained from an *Aspergillus oryzae* strain. In another preferred aspect, an endoglucanase gene is obtained from an *Aspergillus aculeatus* strain. In another preferred aspect, an endoglucanase gene is obtained from a *Humicola insolens* strain.

Preferred examples of endoglucanase genes that can be used in the invention are obtained from *Aspergillus aculeatus* (U.S. Pat. No. 6,623,949; WO 94/14953), *Aspergillus kawachii* (U.S. Pat. No. 6,623,949), *Aspergillus oryzae* (Kitamoto et al., 1996, *Appl. Microbiol. Biotechnol.* 46: 538-544; U.S. Pat. No. 6,635,465), *Aspergillus nidulans* (Lockington et al., 2002, *Fungal Genet. Biol.* 37: 190-196), *Cellulomonas fimi* (Wong et al., 1986, *Gene* 44: 315-324), *Bacillus subtilis* (MacKay et al., 1986, *Nucleic Acids Res.* 14: 9159-9170), *Cellulomonas pachnodae* (Cazemier et al., 1999, *Appl. Microbiol. Biotechnol.* 52: 232-239), *Fusarium equiseti* (Goedegebuur et al., 2002, *Curr. Genet.* 41: 89-98), *Fusarium oxysporum* (Hagen et al., 1994, *Gene* 150: 163-167; Sheppard et al., 1994, *Gene* 150: 163-167), *Humicola insolens* (U.S. Pat. No. 5,912,157; Davies et al., 2000, *Biochem J.* 348: 201-207), *Hypocrea jecorina* (Penttila et al., 1986, *Gene* 45: 253-263), *Humicola grisea* (Goedegebuur et al., 2002, *Curr. Genet.* 41: 89-98), *Micromonospora cellulolyticum* (Lin et al., 1994, *J. Ind. Microbiol.* 13: 344-350), *Myceliophthora thermophila* (U.S. Pat. No. 5,912,157), *Rhizopus oryzae* (Moriya et al., 2003, *J. Bacteriol.* 185: 1749-1756), *Trichoderma reesei* (Saloheimo et al., 1994, *Mol. Microbiol.* 13: 219-228), and *Trichoderma viride* (Kwon et al., 1999, *Biosci. Biotechnol. Biochem.* 63: 1714-1720; Goedegebuur et al., 2002, *Curr. Genet.* 41: 89-98).

Cellobiohydrolases

Cellobiohydrolase, an exo-1,4-beta-D-glucan cellobiohydrolase (E.C. 3.2.1.91), catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain. For purposes of the present invention, cellobiohydrolase activity is determined according to the procedures described by Lever et al., 1972, *Anal. Biochem.* 47: 273-279; van Tilbeurgh et al., 1982, *FEBS Letters*, 149: 152-156; and van Tilbeurgh and Claeyssens, 1985, *FEBS Letters*, 187: 283-288. In the present invention, the Lever et al. method is employed to assess hydrolysis of cellulose in corn stover, while the methods of van Tilbeurgh et al. are used to determine the cellobiohydrolase activity on a fluorescent disaccharide derivative.

In a preferred aspect, a cellobiohydrolase gene is obtained from a *Trichoderma reesei* strain. In another preferred aspect, a cellobiohydrolase gene is obtained from an *Aspergillus aculeatus* strain. In another preferred aspect, a cellobiohydrolase gene is obtained from an *Aspergillus niger* strain. In another preferred aspect, a cellobiohydrolase gene is obtained from an *Aspergillus oryzae* strain. In another preferred aspect, a cellobiohydrolase gene is obtained from an *Emericella nidulans* strain.

Preferred examples of cellobiohydrolase genes that can be used in the invention are obtained from *Acremonium cellulolyticus* (U.S. Pat. No. 6,127,160), *Agaricus bisporus* (Chow et al., 1994, *Appl. Environ. Microbiol.* 60: 2779-2785; Yague et al., 1997, *Microbiology* (Reading, Engl.) 143: 239-244), *Aspergillus aculeatus* (Takada et al., 1998, *J. Ferment. Bioeng.* 85: 1-9), *Aspergillus niger* (Gielkens et al., 1999, *Appl. Environ. Microbiol.* 65: 4340-4345), *Aspergillus oryzae* (Kitamoto et al., 1996, *Appl. Microbiol. Biotechnol.* 46: 538-544), *Athelia rolfsii* (EMBL accession number AB103461), *Chaetomium thermophilum* (EMBL accession numbers AX657571 and CQ838150), *Cullulomonas fimi* (Meinke et al., 1994, *Mol. Microbiol.* 12: 413-422), *Emericella nidulans* (Lockington et al., 2002, *Fungal Genet. Biol.* 37: 190-196), *Fusarium oxysporum* (Hagen et al., 1994, *Gene* 150: 163-167), *Geotrichum* sp. 128 (EMBL accession number AB089343), *Humicola grisea* (de Oliviera and Radford, 1990, *Nucleic Acids Res.* 18: 668; Takashima et al., 1998, *J. Biochem.* 124: 717-725), *Humicola nigrescens* (EMBL accession number AX657571), *Hypocrea koningii* (Teeri et al., 1987, *Gene* 51: 43-52), *Mycelioptera thermophila* (EMBL accession numbers AX657599), *Neocallimastix patriciarum* (Denman et al., 1996, *Appl. Environ. Microbiol.* 62 (6), 1889-1896), *Phanerochaete chrysosporium* (Tempelaars et al., 1994, *Appl. Environ. Microbiol.* 60: 4387-4393), *Thermobifida fusca* (Zhang, 1995, *Biochemistry* 34: 3386-3395), *Trichoderma reesei* (Terri te al., 1983, *Bio/Technology* 1: 696-699; Chen et al., 1987, *Bio/Technology* 5: 274-278), and *Trichoderma viride* (EMBL accession numbers A4368686 and A4368688).

Beta-glucosidase

Beta-glucosidase, a beta-D-glucoside glucohydrolase (E.C. 3.2.1.21), catalyzes the hydrolysis of terminal non-reducing beta-D-glucose residues with the release of beta-D-glucose. For purposes of the present invention, beta-glucosidase activity is determined according to the basic procedure described by Venturi et al., 2002, *J. Basic Microbiol.* 42: 55-66, except different conditions were employed as described herein. One unit of beta-glucosidase activity is defined as 1.0 µmole of p-nitrophenol produced per minute at 50° C., pH 5 from 4 mM p-nitrophenyl-beta-D-glucopyranoside as substrate in 100 mM sodium citrate, 0.01% Tween-20.

Encompassed within the definition of beta-glucosidases are cellobiases. Cellobiases hydrolyze cellobiose to glucose.

In a preferred aspect, a beta-glucosidase gene is obtained from an *Aspergillus aculeatus* strain. In another preferred aspect, a beta-glucosidase gene is obtained from an *Aspergillus kawachi* strain. In another preferred aspect, a beta-glucosidase gene is obtained from a *Trichoderma reesei* strain.

Preferred examples of beta-glucosidase genes that can be used in the invention are obtained from *Aspergillus aculeatus* (Kawaguchi et al., 1996, *Gene* 173: 287-288), *Aspergillus kawachi* (Iwashita et al., 1999, *Appl. Environ. Microbiol.* 65: 5546-5553), *Aspergillus oryzae* (WO 2002/095014), *Cellulomonas biazotea* (Wong et al., 1998, *Gene* 207: 79-86), *Penicillium funiculosum* (WO 200478919), *Saccharomycopsis fibuligera* (Machida et al., 1988, *Appl. Environ. Microbiol.* 54: 3147-3155), *Schizosaccharomyces pombe* (Wood et al., 2002, *Nature* 415: 871-880), and *Trichoderma reesei* (Barnett et al., 1991, *Bio/Technology* 9: 562-567).

Glucohydrolases

Glucohydrolase, an exo-1,4-beta-D-glucan glucohydrolase (E.C. 3.2.1.74), catalyzes the hydrolysis of 1,4-linkages (O-glycosyl bonds) in 1,4-beta-D-glucans so as to remove successive glucose units. For purposes of the present invention, exoglucanase activity is determined according to the procedure described by Himmel et al., 1986, *J. Biol. Chem.* 261: 12948-12955.

In a preferred aspect, a glucohydrolase gene is obtained from a *Trichoderma reesei* strain. In another preferred aspect, a glucohydrolase gene is obtained from a *Humicola insolens* strain. In another preferred aspect, a glucohydrolase gene is obtained from an *Aspergillus niger* strain. In another preferred aspect, a cellobiohydrolase gene is obtained from a *Chaetomium thermophilum* strain. In another preferred aspect, a glucohydrolase gene is obtained from a *Thermoascus aurantiacus* strain. In another preferred aspect, a glucohydrolase gene is obtained from a *Thielavia terrestris* strain.

Hemicellulases

Enzymatic hydrolysis of hemicellulose can be performed by a wide variety of fungi and bacteria (Saha, 2003, *J. Ind. Microbiol. Biotechnol.* 30: 279-291). Similar to cellulose degradation, hemicellulose hydrolysis requires coordinated action of several enzymes. Hemicellulases can be placed into three general categories: the endo-acting enzymes that attack internal bonds within the polysaccharide chain, the exo-acting enzymes that act processively from either the reducing or nonreducing end of polysaccharide chain, and the accessory enzymes, acetylesterases and esterases that hydrolyze lignin glycoside bonds, such as coumaric acid esterase and ferulic acid esterase (Wong, K. K. Y., Tan, L. U. L., and Saddler, J. N., 1988, Multiplicity of β-1,4-xylanase in microorganisms: Functions and applications, *Microbiol. Rev.*, 52: 305-317; Tenkanen, M., and Poutanen, K., 1992, Significance of esterases in the degradation of xylans, in *Xylans and Xylanases*, Visser, J., Beldman, G., Kuster-van Someren, M. A., and Voragen, A. G. J., eds., Elsevier, New York, N.Y., 203-212; Coughlan, M. P., and Hazlewood, G. P., 1993, *Hemicellulose and hemicellulases*, Portland, London, UK; Brigham, J. S., Adney, W. S., and Himmel, M. E., 1996, Hemicellulases: Diversity and applications, in *Handbook on Bioethanol: Production and Utilization*, Wyman, C. E., ed., Taylor & Francis, Washington, D.C., 119-141).

Examples of endo-acting hemicellulases and accessory enzymes include endoarabinanase, endoarabinogalactanase, endoglucanase, endomannanase, endoxylanase, and feraxan endoxylanase. Examples of exo-acting hemicellulases and accessory enzymes include α-L-arabinosidase, β-L-arabinosidase, α-1,2-L-fucosidase, α-D-galactosidase, β-D-galactosidase, β-D-glucosidase, β-D-glucuronidase, β-D-mannosidase, β-D-xylosidase, exo-glucosidase, exo-cellobiohydrolase, exo-mannobiohydrolase, exo-mannanase, exo-xylanase, xylan α-glucuronidase, and coniferin β-glucosidase. Examples of esterases include acetyl esterases (acetylgalactan esterase, acetylmannan esterase, and acetylxylan esterase), and aryl esterases (coumaric acid esterase and ferulic acid esterase).

Hemicellulases include xylanases, arabinofuranosidases, acetyl xylan esterases, glucuronidases, endo-galactanases, mannanases, endo- or exo-arabinases, exo-galactanases, and mixtures thereof. Preferably, the hemicellulase is an exo-acting hemicellulase, and more preferably, an exo-acting hemicellulase which has the ability to hydrolyze hemicellulose preferably in the pH range of about 2 to about 7.

A hemicellulase, such as a xylanase, arabinofuranosidase, acetyl xylan esterase, glucuronidase, endo-galactanase, mannanase, endo- or exo-arabinase, or exo-galactanase, or genes thereof, may be obtained from any suitable source, including fungal and bacterial organisms, such as *Aspergillus*, *Disporotrichum*, *Penicillium*, *Neurospora*, *Fusarium*, *Trichoderma*, *Humicola*, *Thermomyces*, and *Bacillus*.

Preferred examples of hemicellulase genes that can be used in the invention are obtained from *Acidobacterium capsulatum* (Inagaki et al., 1998, *Biosci. Biotechnol. Biochem.* 62: 1061-1067), *Agaricus bisporus* (De Groot et al., 1998, *J. Mol. Biol.* 277: 273-284), *Aspergillus aculeatus* (U.S. Pat. No. 6,197,564; U.S. Pat. No. 5,693,518), *Aspergillus kawachii* (Ito et al., 1992, *Biosci. Biotechnol. Biochem.* 56: 906-912), *Aspergillus niger* (EMBL accession number AF108944), *Magnaporthe grisea* (Wu et al., 1995, *Mol. Plant Microbe Interact.* 8: 506-514), *Penicillium chrysogenum* (Haas et al., 1993, *Gene* 126: 237-242), *Talaromyces emersonii* (WO 02/24926), and *Trichoderma reesei* (EMBL accession numbers X69573, X69574, and AY281369).

Lignin-Degrading Enzymes

Lignin is an aromatic polymer occurring in the woody tissue of higher plants. Due to its hydrophobicity and complex random structure lacking regular hydrolyzable bonds, lignin is poorly degraded by most organisms. The best degraders of lignin are white rot fungi that produce extracellular peroxidases and laccases, which are involved in the initial attack of lignin.

Lignin-degrading enzymes include, but are not limited to, lignin peroxidases, manganese-dependent peroxidases, hybrid peroxidases, with combined properties of lignin peroxidases and manganese-dependent peroxidases, and laccases (Vicuna, 2000, supra; Broda et al., 1996, supra). Hydrogen peroxide, required as a co-substrate by the peroxidases, can be generated by glucose oxidase, aryl alcohol oxidase, and/or lignin peroxidase-activated glyoxal oxidase.

Manganese-dependent peroxidase is a frequently encountered peroxidase produced by white rot fungi. The peroxidase has a catalytic cycle involving a 2-electron oxidation of the heme by hydrogen peroxide and subsequent oxidation of compound I via compound II in two 1-electron steps to the native enzyme. The best reducing substrate for compounds I and II is Mn(II), a metal naturally present in wood. The Mn(III) formed oxidizes other substrates.

Organic acids such as oxalate, glyoxylate, and lactate are known to have an important role in the mechanism of manganese-dependent peroxidase and lignin degradation. Mn(III) is stripped from the enzyme by organic acids, and the produced Mn(III)-organic acid complex acts as a diffusible mediator in the oxidation of lignin by manganese-dependent peroxidase. Mn(III) can also oxidize organic acids, yielding radicals. The organic acids may also be supplied from the degradation of lignin and by microorganisms.

Lignin-degrading enzymes and genes thereof may be obtained from a *Bjerkandera adusta, Ceriporiopsis subvermispora* (see WO 02/079400), *Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* strain.

Preferred examples of genes encoding lignin-degrading enzymes that can be used in the invention are obtained from *Bjerkandera adusta* (WO 2001/098469), *Ceriporiopsis subvermispora* (Conesa et al., 2002, *Journal of Biotechnology* 93: 143-158), *Cantharellus cibariusi* (Ng et al., 2004, *Biochemical and Biophysical Research Communications* 313: 37-41), *Coprinus cinereus* (WO 97/008325; Conesa et al., 2002, supra), *Lentinula edodes* (Nagai et al., 2002, *Applied Microbiology and Biotechnology* 60: 327-335, 2002), *Melanocarpus albomyces* (Kiiskinen et al., 2004, *FEBS Letters* 576: 251-255, 2004), *Myceliophthora thermophila* (WO 95/006815), *Phanerochaete chrysosporium* (Conesa et al., 2002, supra; Martinez, 2002, *Enzyme and Microbial Technology* 30: 425-444, 2002), *Phlebia radiata* (Conesa et al., 2002, supra), *Pleurotus eryngii* (Conesa et al., 2002, supra), *Polyporus pinsitus* (WO 96/000290), *Rigidoporus lignosus* (Garavaglia et al., 2004, *Journal of Molecular Biology* 342: 1519-1531), *Rhizoctonia solani* (WO 96/007988), *Scytalidium thermophilum* (WO 95/033837), *Tricholoma giganteum* (Wang et al., 2004, *Biochemical and Biophysical Research Communications* 315: 450-454), and *Trametes versicolor* (Conesa et al., 2002, supra).

Esterases

Esterase, a carboxylic ester hydrolase (EC 3.1.1), catalyzes the hydrolysis of ester bonds. Esterases useful in the degradation or conversion of plant cell wall polysaccharides include acetyl esterases such as acetylgalactan esterase, acetylmannan esterase, and acetylxylan esterase, and esterases that hydrolyze lignin glycoside bonds, such as coumaric acid esterase and ferulic acid esterase.

Non-limiting examples of esterases include arylesterase, triacylglycerol lipase, acetylesterase, acetylcholinesterase, cholinesterase, tropinesterase. pectinesterase, sterol esterase, chlorophyllase, L-arabinonolactonase, gluconolactonase, uronolactonase, tannase, retinyl-palmitate esterase, hydroxybutyrate-dimer hydrolase, acylglycerol lipase, 3-oxoadipate enol-lactonase, 1,4-lactonase, galactolipase, 4-pyridoxolactonase, acylcarnitine hydrolase, aminoacyl-tRNA hydrolase, D-arabinonolactonase, 6-phosphogluconolactonase, phospholipase A1, 6-acetylglucose deacetylase, lipoprotein lipase, dihydrocoumarin lipase, limonin-D-ring-lactonase, steroid-lactonase, triacetate-lactonase, actinomycin lactonase, orsellinate-depside hydrolase, cephalosporin-C deacetylase, chlorogenate hydrolase, alpha-amino-acid esterase, 4-methyloxaloacetate esterase, carboxymethylenebutenolidase, deoxylimonate A-ring-lactonase, 2-acetyl-1-alkylglycerophosphocholine esterase, fusarinine-C ornithinesterase, sinapine esterase, wax-ester hydrolase, phorbol-diester hydrolase, phosphatidylinositol deacylase, sialate O-acetylesterase, acetoxybutynylbithiophene deacetylase, acetylsalicylate deacetylase, methylumbelliferyl-acetate deacetylase, 2-pyrone-4,6-dicarboxylate lactonase, N-acetylgalactosaminoglycan deacetylase, juvenile-hormone esterase, bis(2-ethylhexyl)phthalate esterase, proteinglutamate methylesterase, 11-cis-retinyl-palmitate hydrolase, all-trans-retinyl-palmitate hydrolase, L-rhamnono-1,4-lactonase, 5-(3,4-diacetoxybut-1-ynyl)-2,2'-bithiophene deacetylase, fatty-acyl-ethyl-ester synthase, xylono-1,4-lactonase, N-acetylglucosaminylphosphatidylinositol deacetylase, cetraxate benzylesterase, acetylalkylglycerol acetylhydrolase, and acetylxylan esterase.

Preferred esterases for use in the present invention are lipolytic enzymes, such as, lipases (EC 3.1.1.3, EC 3.1.1.23 and/or EC 3.1.1.26) and phospholipases (EC 3.1.1.4 and/or EC 3.1.1.32, including lysophospholipases classified by EC 3.1.1.5). Other preferred esterases are cutinases (EC 3.1.1.74). Further preferred esterases are acetylxylan esterase and pectin methylesterase.

The esterase may be added in an amount effective to obtain the desired benefit to improve the performance of the spent whole broth or a fermenting microorganism, e.g., to change the lipid composition/concentration inside and/or outside of the fermenting microorganism or in the cell membrane of the fermenting microorganism, to result in an improvement in the movement of solutes into and/or out of the fermenting microorganisms during fermentation and/or to provide more metabolizable energy sources (such as, e.g., by converting components, such as, oil from the corn substrate, to components useful the fermenting microorganism, e.g., unsaturated fatty acids and glycerol), to increase ethanol yield. Examples of effective amounts of esterase are from 0.01 to 400 LU/g DS (Dry Solids). Preferably, the esterase is used in an amount of 0.1 to 100 LU/g DS, more preferably 0.5 to 50 LU/g DS, and even more preferably 1 to 20 LU/g DS. Further optimization of the amount of esterase can hereafter be obtained using standard procedures known in the art.

One Lipase Unit (LU) is the amount of enzyme which liberates 1.0 μmol of titratable fatty acid per minute with tributyrin as substrate and gum arabic as an emulsifier at 30° C., pH 7.0 (phosphate buffer).

In a preferred aspect the esterase is a lipolytic enzyme, more preferably, a lipase. As used herein, a "lipolytic enzyme" refers to lipases and phospholipases (including lysophospholipases). In a more preferred aspect, the lipolytic enzyme is a lipase. Lipases may be applied herein for their ability to modify the structure and composition of triglyceride oils and fats in the fermentation media (including fermentation yeast), for example, resulting from a corn substrate. Lipases catalyze different types of triglyceride conversions, such as hydrolysis, esterification and transesterification. Suitable lipases include acidic, neutral and basic lipases, as are well-known in the art, although acidic lipases (such as, e.g., the lipase G AMANO 50, available from Amano) appear to be more effective at lower concentrations of lipase as compared to either neutral or basic lipases. Preferred lipases for use in the present invention included *Candida antarctica* lipase and *Candida cylindracea* lipase. More preferred lipases are purified lipases such as *Candida antarctica* lipase (lipase A), *Candida antarctica* lipase (lipase B), *Candida cylindracea* lipase, and *Penicillium camembertii* lipase.

The lipase may be the lipase disclosed in EP 258,068-A or may be a lipase variant such as a variant disclosed in WO 00/60063 or WO 00/32758, hereby incorporated by reference.

Lipases are preferably present in amounts from about 1 to 400 LU/g DS, preferably 1 to 10 LU/g DS, and more preferably 1 to 5 LU/g DS.

The lipolytic enzyme is preferably of microbial origin, in particular, of bacterial, fungal or yeast origin. The lipolytic enzyme or gene thereof used may be obtained from any source, including, for example, a strain of *Absidia*, in particular *Absidia blakesleena* and *Absidia corymbifera*, a strain of *Achromobacter*, in particular *Achromobacter iophagus*, a strain of *Aeromonas*, a strain of *Alternaria*, in particular *Alternaria brassiciola*, a strain of *Aspergillus*, in particular *Aspergillus niger* and *Aspergillus flavus*, a strain of *Achromobacter*, in particular *Achromobacter iophagus*, a strain of *Aureobasidium*, in particular *Aureobasidium pullulans*, a strain of *Bacillus*, in particular *Bacillus pumilus, Bacillus strearothermophilus*, and *Bacillus subtilis*, a strain of *Beauveria*, a strain of *Brochothrix*, in particular *Brochothrix thermosohata*, a strain of *Candida*, in particular *Candida cylindracea* (*Candida rugosa*), *Candida paralipolytica*, and *Candida antarctica*, a strain of *Chromobacter*, in particular *Chromobacter viscosum*, a strain of *Coprinus*, in particular *Coprinus cinereus*, a strain of *Fusarium*, in particular *Fusarium oxysporum, Fusarium solani, Fusarium solani pisi, Fusarium roseum culmorum*, and *Fusarium venenatum*, a strain of *Geotricum*, in particular *Geotricum penicillatum*, a strain of *Hansenula*, in particular *Hansenula anomala*, a strain of *Humicola*, in particular *Humicola brevispora, Humicola brevis* var. *thermoidea*, and *Humicola insolens*, a strain of *Hyphozyma*, a strain of *Lactobacillus*, in particular *Lactobacillus curvatus*, a strain of *Metarhizium*, a strain of *Mucor*, a strain of *Paecilomyces*, a strain of *Penicillium*, in particular *Penicillium cyclopium, Penicillium crustosum* and *Penicillium expansum*, a strain of *Pseudomonas* in particular *Pseudomonas aeruginosa, Pseudomonas alcaligenes, Pseudomonas cepacia* (syn. *Burkholderia cepacia*), *Pseudomonas fluorescens, Pseudomonas fragi, Pseudomonas maltophilia, Pseudomonas mendocina, Pseudomonas mephitica lipolytica, Pseudomonas alcaligenes, Pseudomonas plantari, Pseudomonas pseudoalcaligenes, Pseudomonas putida, Pseudomonas stutzeri*, and *Pseudomonas wisconsinensis*, a strain of *Rhizoctonia*, in particular *Rhizoctonia solani*, a strain of *Rhizomucor*, in particular *Rhizomucor miehei*, a strain of *Rhizopus*, in particular *Rhizopus japonicus, Rhizopus microsporus*, and *Rhizopus nodosus*, a strain of *Rhodosporidium*, in particular *Rhodosporidium toruloides*, a strain of *Rhodotorula*, in particular *Rhodotorula glutinis*, a strain of *Sporobolomyces*, in particular *Sporobolomyces shibatanus*, a strain of *Thermomyces*, in particular *Thermomyces lanuginosus* (formerly *Humicola lanuginosa*), a strain of *Thiarosporella*, in particular *Thiarosporella phaseolina*, a strain of *Trichoderma*, in particular, *Trichoderma harzianum* and *Trichoderma reesei*, and/or a strain of *Verticillium*.

In a preferred aspect, the lipolytic enzyme or gene thereof is obtained from a strain of *Aspergillus, Achromobacter, Bacillus, Candida, Chromobacter, Fusarium, Humicola, Hyphozyma, Pseudomonas, Rhizomucor, Rhizopus*, or *Thermomyces*.

Preferred examples of lipase genes that can be used in the invention are obtained from *Absidia* sp. (WO 97/027276), *Candida antarctica* (EMBL accession number Z30645), *Candida cylindracea* (EMBL accession numbers X64703, X64704, X66006, X66007, and X66008), *Fusarium oxysporum* (WO 98/26057), *Penicillium camembertii* (Yamaguchi et al., 1991, *Gene* 103: 61-67), and *Thermomyces lanuginosus* (EMBL accession number AF054513).

In another preferred aspect, at least one esterase is a cutinase. Cutinases are enzymes which are able to degrade cutin. The cutinase or gene thereof may be obtained from any source. In a preferred aspect, the cutinase or gene thereof is obtained from a strain of *Aspergillus*, in particular *Aspergillus oryzae*, a strain of *Alternaria*, in particular *Alternaria brassiciola*, a strain of *Fusarium*, in particular *Fusarium solani, Fusarium solani pisi, Fusarium roseum culmorum*, or *Fusarium roseum sambucium*, a strain of *Helminthosporum*, in particular *Helminthosporum sativum*, a strain of *Humicola*, in particular *Humicola insolens*, a strain of *Pseudomonas*, in particular *Pseudomonas mendocina* or *Pseudomonas putida*, a strain of *Rhizoctonia*, in particular *Rhizoctonia solani*, a strain of *Streptomyces*, in particular *Streptomyces scabies*, or a strain of *Ulocladium*, in particular *Ulocladium consortiale*.

In a most preferred aspect, the cutinase or gene thereof is obtained from a strain of *Humicola insolens*, in particular *Humicola insolens* DSM 1800. *Humicola insolens* cutinase is described in WO 96/13580 which is hereby incorporated by reference. The cutinase gene may encode a variant such as one of the variants disclosed in WO 00/34450 and WO 01/92502, hereby incorporated by reference. Preferred cutinase variants include variants listed in Example 2 of WO 01/92502 which are hereby specifically incorporated by reference. An effective amount of cutinase is between 0.01 and 400 LU/g DS, preferably from about 0.1 to 100 LU/g DS, more preferably, 1 to 50 LU/g DS.

Preferred examples of cutinase genes that can be used in the invention are obtained from *Fusarium solani* (WO 90/09446; U.S. Pat. No. 5,827,719; WO 00/34450; and WO 01/92502) and *Humicola insolens* (WO 96/13580), and variants thereof.

In another preferred aspect, at least one esterase is a phospholipase. As used herein, the term "phospholipase" is an enzyme which has activity towards phospholipids. Phospholipids, such as lecithin or phosphatidylcholine, consist of glycerol esterified with two fatty acids in an outer (sn-1) and the middle (sn-2) positions and esterified with phosphoric acid in the third position. The phosphoric acid, in turn, may be esterified to an amino-alcohol. Several types of phospholipase activity can be distinguished, including phospholipases $A_1$ and $A_2$ which hydrolyze one fatty acyl group (in the sn-1 and sn-2 position, respectively) to form lysophospholipid; and lysophospholipase (or phospholipase B), which hydrolyze the remaining fatty acyl group in lysophospholipid. Phospholipase C and phospholipase D (phosphodiesterases) release diacyl glycerol or phosphatidic acid, respectively.

The term "phospholipase" includes enzymes with phospholipase activity, e.g., phospholipase A ($A_1$ or $A_2$), phospholipase B activity, phospholipase C activity, or phospholipase D activity. The phospholipase activity may be provided by enzymes having other activities as well, such as, e.g., a lipase with phospholipase activity. In other aspects of the invention, phospholipase activity is provided by an enzyme having essentially only phospholipase activity and wherein the phospholipase enzyme activity is not a side activity.

The phospholipase or gene thereof may be of any origin, e.g., of animal origin (e.g., mammalian such as from bovine or porcine pancreas), or snake venom or bee venom. Alternatively, the phospholipase may be of microbial origin, e.g., from filamentous fungi, yeast, or bacteria, such as *Aspergillus*, e.g., *Aspergillus fumigatus, Aspergillus awamori, Aspergillus foetidus, Aspergillus japonicus, Aspergillus niger*, and *Aspergillus oryzae, Dictyostelium*, e.g., *Dictyostelium discoideum; Fusarium*, e.g., *Fusarium culmorum, Fusarium heterosporum, Fusarium oxysporum, Fusarium solani*, and *Fusarium venenatum; Mucor*, e.g., *Mucor javanicus, Mucor mucedo*, and *Mucor subtilissimus; Neurospora*, e.g., *Neurospora crassa; Rhizomucor*, e.g., *Rhizomucor pusillus; Rhizopus*, e.g., *Rhizopus arrhizus, Rhizopus japonicus*, and *Rhizopus stolonifer, Sclerotinia*, e.g., *Sclerotinia libertiana; Trichophyton*, e.g., *Trichophyton rubrum; Whetze-* linia, e.g., *Whetzelinia sclerotiorum*; *Bacillus*, e.g., *Bacillus megaterium* and *Bacillus subtilis*; *Citrobacter*, e.g., *Citrobacter freundii*; *Enterobacter*, e.g., *Enterobacter aerogenes* and *Enterobacter cloacae*; *Edwardsiella*, *Edwardsiella tarda*; *Erwinia*, e.g., *Erwinia herbicola*; *Escherichia*, e.g., *E. coli*; *Klebsiella*, e.g., *Klebsiella pneumoniae*; *Proteus*, e.g., *Proteus vulgaris*; *Providencia*, e.g., *Providencia stuartii*; *Salmonella*, e.g., *Salmonella typhimurium*; *Serratia*, e.g., *Serratia liquefasciens* and *Serratia marcescens*; *Shigella*, e.g., *Shigella flexneri*; *Streptomyces*, e.g., *Streptomyces violeceoruber*, and *Yersinia*, e.g., *Yersinia enterocolitica*. Preferred commercial phospholipases include LECITASE™ and LECITASE™ ULTRA (available from Novozymes A/S, Denmark).

An effective amount of phospholipase is between 0.01 and 400 LU/g DS, preferably from about 0.1 to 100 LU/g DS, more preferably, 1 to 50 LU/g DS. Further optimization of the amount of phospholipase can hereafter be obtained using standard procedures known in the art.

Enzyme assays for phospholipases are well known in the art (see, for example, Kim et al., 1997, *Anal. Biochem.* 250: 109-116; Wu and Cho, 1994, *Anal. Biochem.* 221: 152-159; Hirashima et al., 1983, *Brain and Nerve* 35: 811-817; and Chen et al., 1997, *Infection and Immun.* 65: 405-411).

Preferred examples of phospholipase genes that can be used in the invention are obtained from *Fusarium venenatum* (WO 00/028044), *Aspergillus oryzae* (WO 01/029222), *Fusarium oxysporum* (WO 98/26057), *Penicillum notatum* (Masuda et al., 1991, *European Journal of Biochemistry* 202: 783-787), *Torulaspora delbrueckii* (Watanabe et al., 1994, *FEMS Microbiology Letters* 124: 29-34), *Saccharomyces cerevisiae* (Lee at al., 1994, *Journal of Biological Chemistry* 269: 19725-19730), *Aspergillus* (JP 10155493), *Neurospora crassa* (EMBL 042791), and *Schizosaccharomyces pombe* (EMBL 013857).

Proteases

In another preferred aspect, a protease may be useful in the degradation of plant cell wall polysaccharides into one or more products. The protease may be used, for example, to digest protein to produce free amino nitrogen (FAN), where such free amino acids function as nutrients for yeast, thereby enhancing the growth of the yeast and, consequently, the production of ethanol. Proteases may also liberate bound polysaccharide material.

The propagation of a fermenting microorganism with an effective amount of at least one protease may reduce the lag time of the fermenting microorganism. The action of the protease in the propagation process is believed to directly or indirectly result in the suppression or expression of genes which are detrimental or beneficial, respectively, to the fermenting microorganism during fermentation, thereby decreasing lag time and resulting in a faster fermentation cycle.

Proteases are well known in the art and refer to enzymes that catalyze the cleavage of peptide bonds. Suitable proteases include fungal and bacterial proteases. Preferred proteases are acidic proteases, i.e., proteases characterized by the ability to hydrolyze proteins under acidic conditions below pH 7. Acid fungal proteases or genes thereof can be obtained from *Aspergillus, Mucor, Rhizopus, Candida, Coriolus, Endothia, Enthomophtra, Irpex, Penicillium, Sclerotium*, and *Torulopsis*. In a preferred aspect, a protease or gene thereof is obtained from Preferably, the protease is an aspartic acid protease, as described, for example, in Handbook of Proteolytic Enzymes, Edited by A. J. Barrett, N. D. Rawlings and J. F. Woessner, Academic Press, San Diego, 1998, Chapter 270).

Enzyme assays for acid proteases, e.g., aspartic acid proteases, are well known in the art (see, for example, Litvinov et al., 1998, *Bioorg. Khim.* 24: 175-178).

Preferred examples of acid protease genes that can be used in the invention are obtained from *Aspergillus awamori* (Berka et al., 1990, *Gene* 86: 153-162), *Aspergillus niger* (Koaze et al., 1964, *Agr. Biol. Chem. Japan* 28: 216), *Aspergillus saitoi* (Yoshida, 1954, *J. Agr. Chem. Soc. Japan* 28: 66), *Aspergillus awamori* (Hayashida et al., 1977, *Agric. Biol. Chem.* 42: 927-933), *Aspergillus aculeatus* (WO 95/02044), and *Aspergillus oryzae* (Berka et al., 1993, *Gene* 125:195-198).

Peroxidases

A peroxidase may be any peroxidase (e.g., EC 1.11.1.7), or any fragment obtained therefrom, exhibiting peroxidase activity.

The peroxidase or gene thereof can be obtained from plants (e.g., horseradish or soybean peroxidase) or microorganisms (e.g., fungi or bacteria).

Some preferred fungi include strains belonging to the subdivision *Deuteromycotina*, class *Hyphomycetes*, e.g., *Fusarium, Humicola, Tricoderma, Myrothecium, Verticillum, Arthromyces, Caldariomyces, Ulocladium, Embellisia, Cladosporium* or *Dreschlera*, in particular *Fusarium oxysporum* (DSM 2672), *Humicola insolens, Trichoderma resii, Myrothecium verrucaria* (IFO 6113), *Verticillum alboatrum, Verticillum dahlie, Arthromyces ramosus* (FERM P-7754), *Caldariomyces fumago, Ulocladium chartarum, Embellisia alli*, and *Dreschlera halodes*.

Other preferred fungi include strains belonging to the subdivision *Basidiomycotina*, class *Basidiomycetes*, e.g., *Coprinus, Phanerochaete, Coriolus* or *Trametes*, in particular *Coprinus cinereus* f. *microsporus* (IFO 8371), *Coprinus macrorhizus, Phanerochaete chrysosporium* (e.g. NA-12), or *Trametes* (previously called *Polyporus*), e.g., *T. versicolor* (e.g. PR4 28-A).

Further preferred fungi include strains belonging to the subdivision *Zygomycotina*, class *Mycoraceae*, e.g., *Rhizopus* or *Mucor*, in particular *Mucor hiemalis*.

Some preferred bacteria include strains of the order *Actinomycetales*, e.g. *Streptomyces spheroides* (ATTC 23965), *Streptomyces thermoviolaceus* (IFO 12382), and *Streptoverticillum verticillium* ssp. *verticillium*.

Other preferred bacteria include *Rhodobacter sphaeroides, Rhodomonas palustri, Streptococcus lactis, Pseudomonas purrocinia* (ATCC 15958), *Pseudomonas fluorescens* (NRRL B-11), and *Bacillus* strains, e.g., *Bacillus pumilus* (ATCC 12905) and *Bacillus stearothermophilus*.

Further preferred bacteria include strains belonging to *Myxococcus*, e.g., *M. virescens*.

In a preferred aspect, a gene encoding a peroxidase is obtained from a *Coprinus* sp., in particular, *Coprinus macrorhizus* or *Coprinus cinereus* according to WO 92/16634.

In the present invention, genes encoding a peroxidase include peroxidases and peroxidase active fragments obtained from cytochromes, haemoglobin, or peroxidase enzymes.

One peroxidase unit (POXU) is the amount of enzyme which under the following conditions catalyzes the conversion of 1 µmole hydrogen peroxide per minute: 0.1 M phosphate buffer pH 7.0, 0.88 mM hydrogen peroxide, and 1.67 mM 2,2'-azino-bis(3-ethylbenzothiazoline-6-sulfonate) (ABTS) at 30° C. The reaction is followed for 60 seconds (15 seconds after mixing) by the change in absorbance at 418 nm, which should be in the range 0.15 to 0.30. For calculation of activity is used an absorption coefficient of oxidized ABTS of 36 mM$^{-1}$ cm$^{-1}$ and a stoichiometry of one µmole H$_2$O$_2$ converted per two µmole ABTS oxidized.

Preferred examples of peroxidase genes that can be used in the invention are obtained from *Bjerkandera adusta* (WO 2001/098469), *Ceriporiopsis subvermispora* (Conesa et al., 2002, *Journal of Biotechnology* 93: 143-158), *Coprinus cinereus* (Conesa et al., 2002, supra), *Phanerochaete chrysosporium* (Conesa et al., 2002, supra), *Phlebia radiata* (Conesa et al., 2002, supra), *Pleurotus eryngii* (Conesa et al., 2002, supra), and *Trametes versicolor* (Conesa et al., 2002, supra).

Laccases

In the present invention, the laccase may be any laccase or laccase-related enzyme including any laccase (EC 1.10.3.2), any catechol oxidase (EC 1.10.3.1), any bilirubin oxidase (EC 1.3.3.5), or any monophenol monooxygenase (EC 1.14.18.1).

The above-mentioned enzymes or genes thereof may be obtained from a microorganism, i.e., bacteria or fungi (including filamentous fungi and yeasts), or they may be obtained from plants.

Suitable fungal sources include *Aspergillus*, *Neurospora*, e.g., *Neurospora crassa*, *Podospora*, *Botrytis*, *Collybia*, *Fomes*, *Lentinus*, *Pleurotus*, *Trametes*, e.g., *Trametes villosa* and *Trametes versicolor*, *Rhizoctonia*, e.g., *Rhizoctonia solani*, *Coprinus*, e.g., *Coprinus cinereus*, *Coprinus comatus*, *Coprinus friesii*, and *Coprinus plicatilis*, *Psathyrella*, e.g., *Psathyrella condelleana*, *Panaeolus*, e.g., *Panaeolus papilionaceus*, *Myceliophthora*, e.g., *Myceliophthora thermophila*, *Scytalidium*, e.g., *Scytalidium thernophilum*, *Polyporus*, e.g., *Polyporus pinsitus*, *Pycnoporus*, e.g., *Pycnoporus cinnabarinus*, *Phlebia*, e.g., *Phlebia radita* (WO 92/01046), or *Coriolus*, e.g., *Coriolus hirsutus* (JP 2-238885). Suitable bacteria sources are *Bacillus*.

A laccase or gene thereof is perferably obtained from *Coprinus*, *Myceliophthora*, *Polyporus*, *Pycnoporus*, *Scytalidium* or *Rhizoctonia*; in particular *Coprinus cinereus*, *Myceliophthora thermophila*, *Polyporus pinsitus*, *Pycnoporus cinnabarinus*, *Scytalidium thermophilum*, or *Rhizoctonia solani*.

Laccase activity (LACU) is determined from the oxidation of syringaldazine under aerobic conditions. The violet colour produced is photometered at 530 nm. The analytical conditions are 19 mM syringaldazine, 23 mM acetate buffer, pH 5.5, 30° C., 1 minute reaction time. One laccase unit (LACU) is the amount of enzyme that catalyses the conversion of 1.0 µmole syringaldazine per minute at these conditions.

Laccase activity (LAMU) is determined from the oxidation of syringaldazine under aerobic conditions. The violet colour produced is photometered at 530 nm. The analytical conditions are 19 mM syringaldazine, 23 mM Tris/maleate pH 7.5, 30° C., 1 minute reaction time. One laccase unit (LAMU) is the amount of enzyme that catalyses the conversion of 1.0 µmole syringaldazine per minute at these conditions.

Preferred examples of laccase genes that can be used in the invention are obtained from *Cantharellus cibariusi* (Ng et al., 2004, *Biochemical and Biophysical Research Communications* 313: 37-41), *Coprinus cinereus* (WO 97/008325), *Lentinula edodes* (Nagai et al., 2002, *Applied Microbiology and Biotechnology* 60: 327-335, 2002), *Melanocarpus albomyces* (Kiiskinen et al., 2004, *FEBS Letters* 576: 251-255, 2004), *Myceliophthora thermophila* (WO 95/006815), *Polyporus pinsitus* (WO 96/000290), *Rigidoporus lignosus* (Garavaglia et al., 2004, *Journal of Molecular Biology* 342: 1519-1531), *Rhizoctonia solani* (WO 96/007988), *Scytalidium thermophilum* (WO 95/033837), and *Tricholoma giganteum* (Wang et al., 2004, *Biochemical and Biophysical Research Communications* 315: 450-454).

Nucleic Acid Constructs

An isolated gene encoding a plant cell wall polysaccharide degrading or converting enzyme, e.g., a cellulose-degrading enzyme, hemicellulase, esterase, laccase, ligninase, protease, or peroxidase may be manipulated in a variety of ways to provide for expression of the enzyme. Manipulation of the gene prior to its insertion into a vector may be desirable or necessary depending on the expression vector. The techniques for modifying nucleotide sequences utilizing recombinant DNA methods are well known in the art.

The term "nucleic acid construct" as used herein refers to a nucleic acid molecule, either single- or double-stranded, which is isolated from a naturally occurring gene or which has been modified to contain segments of nucleic acids in a manner that would not otherwise exist in nature. The term nucleic acid construct is synonymous with the term "expression cassette" when the nucleic acid construct contains the control sequences required for expression of a coding sequence of the present invention.

The term "control sequences" is defined herein to include all components, which are necessary or advantageous for the expression of a polypeptide having an enzyme activity of interest. Each control sequence may be native or foreign to the nucleotide sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

The term "operably linked" as used herein refers to a configuration in which a control sequence is placed at an appropriate position relative to the coding sequence of the DNA sequence such that the control sequence directs the expression of a polypeptide.

When used herein the term "coding sequence" is intended to cover a nucleotide sequence, which directly specifies the amino acid sequence of its protein product. The boundaries of the coding sequence are generally determined by an open reading frame, which usually begins with the ATG start codon or alternative start codons such as GTG and TTG. The coding sequence typically include DNA, cDNA, and recombinant nucleotide sequences.

The term "expression" includes any step involved in the production of the polypeptide including, but not limited to, transcription, post-transcriptional modification, translation, post-translational modification, and secretion.

The control sequence may be an appropriate promoter sequence, a nucleotide sequence which is recognized by a host for expression of the gene. The promoter sequence contains transcriptional control sequences which mediate the expression of the polypeptide. The promoter may be any nucleotide sequence which shows transcriptional activity in the host of choice including mutant, truncated, and hybrid promoters, and may be obtained from genes encoding extracellular or intracellular polypeptides either homologous or heterologous to the host.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionine (CUP1), and *Saccharomyces cerevisiae* 3-phosphoglycerate kinase. Other useful promoters for yeast hosts are described by Romanos et al., 1992, *Yeast* 8: 423-488.

In the case of the degradation or conversion of plant cell wall polysaccharides, the choice of the promoter necessarily requires that it be induced by growth of the host on the polysaccharide biomass.

The control sequence may also be a suitable transcription terminator sequence, a sequence recognized by a host to terminate transcription. The terminator sequence is operably linked to the 3' terminus of the gene encoding an enzyme. Any terminator which is functional in the host of choice may be used in the present invention.

Preferred terminators for filamentous fungal hosts are obtained from the genes for *Aspergillus oryzae* TAKA amylase, *Aspergillus niger* glucoamylase, *Aspergillus nidulans* anthranilate synthase, *Trichoderma reesei* CBHI, *Aspergillus niger* alpha-glucosidase, and *Fusarium oxysporum* trypsin-like protease.

Preferred terminators for yeast hosts are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast hosts are described by Romanos et al., 1992, supra.

The control sequence may also be a suitable leader sequence, a nontranslated region of an mRNA which is important for translation by the host. The leader sequence is operably linked to the 5' terminus of a gene. Any leader sequence that is functional in the host of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of a gene and which, when transcribed, is recognized by the host as a signal to add polyadenosine residues to transcribed mRNA. Any polyadenylation sequence which is functional in the host of choice may be used in the present invention.

Preferred polyadenylation sequences for filamentous fungal hosts are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast hosts are described by Guo and Sherman, 1995, *Molecular Cellular Biology* 15: 5983-5990.

The control sequence may also be a signal peptide coding region that codes for an amino acid sequence linked to the amino terminus of an enzyme and directs the encoded enzyme into the cell's secretory pathway. The 5' end of the coding sequence of the gene may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the enzyme. However, any signal peptide coding region which directs the expressed polypeptide into the secretory pathway of a host cell of choice, i.e., secreted into a culture medium, may be used in the present invention.

Effective signal peptide coding regions for filamentous fungal hosts are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola lanuginosa* lipase, *Trichoderma reesei* CBHI, *Trichoderma reesei* CBHII, *Trichoderma reesei* EGI, and *Trichoderma reesei* CBHIII.

Useful signal peptides for yeast hosts are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of an enzyme. The resultant polypeptide is known as a proenzyme or propolypeptide (or a zymogen in some cases). A propolypeptide is generally inactive and can be converted to a mature active enzyme by catalytic or autocatalytic cleavage of the propeptide from the propolypeptide. The propeptide coding region may be obtained from genes for *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of an enzyme, the propeptide region is positioned next to the amino terminus of the enzyme and the signal peptide region is positioned next to the amino terminus of the propeptide region.

It may also be desirable to add regulatory sequences which allow the regulation of the expression of an enzyme relative to the growth of the host. Examples of regulatory systems are those which cause the expression of a gene to be turned on or off in response to a chemical or physical stimulus, including the presence of a regulatory compound. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the gene would be operably linked with the regulatory sequence.

Expression Vectors

The various nucleic acids and control sequences described above may be joined together to produce a recombinant expression vector which may include one or more convenient restriction sites to allow for insertion or substitution of a gene at such sites. Alternatively, a gene may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The term "expression vector" encompasses a DNA molecule, linear or circular, that comprises a segment encoding an enzyme, and which is operably linked to additional segments that provide for its transcription.

The recombinant expression vector may be any vector (e.g., a plasmid or virus) which can be conveniently subjected to recombinant DNA procedures and can bring about the expression of a gene of interest. The choice of the vector will typically depend on the compatibility of the vector with the host into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host, is integrated into the genome and replicated together with the chromosome(s) into which it has been integrated. Furthermore, a single vector or plasmid or two or more vectors or plasmids which together contain the total DNA to be introduced into the genome of the host, or a transposon may be used.

The vectors preferably contain one or more selectable markers which permit easy selection of transformed hosts. A selectable marker is a gene the product of which provides for biocide or viral resistance, resistance to heavy metals, prototrophy to auxotrophs, and the like.

Suitable markers for yeast hosts are ADE2, HIS3, LEU2, LYS2, MET3, TRP1, and URA3. Selectable markers for use in a filamentous fungal host include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in *Aspergillus* are the amdS and pyrG genes of *Aspergillus nidulans* or *Aspergillus oryzae* and the bar gene of *Streptomyces hygroscopicus*. Preferred for use in *Trichoderma* are bar and amdS.

The vectors preferably contain an element(s) that permits integration of the vector into the host's genome or autonomous replication of the vector in the cell independent of the genome.

For integration into the host genome, the vector may rely on the gene's sequence or any other element of the vector for integration of the vector into the genome by homologous or nonhomologous recombination. Alternatively, the vector may contain additional nucleotide sequences for directing integration by homologous recombination into the genome of the host. The additional nucleotide sequences enable the vector to be integrated into the host genome at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which are highly homologous with the corresponding target sequence to enhance the probability of homologous recombination. The integrational elements may be any sequence that is homologous with the target sequence in the genome of the host. Furthermore, the integrational elements may be non-encoding or encoding nucleotide sequences. On the other hand, the vector may be integrated into the genome of the host by non-homologous recombination.

For autonomous replication, the vector may further comprise an origin of replication enabling the vector to replicate autonomously in the host in question. The origin of replication may be any plasmid replicator mediating autonomous replication which functions in a cell. The term "origin of replication" or "plasmid replicator" is defined herein as a sequence that enables a plasmid or vector to replicate in vivo. Examples of origins of replication for use in a yeast host are the 2 micron origin of replication, ARS1, ARS4, the combination of ARS1 and CEN3, and the combination of ARS4 and CEN6. Examples of origins of replication useful in a filamentous fungal cell are AMA1 and ANS1 (Gems et al., 1991, *Gene* 98: 61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a gene may be inserted into the host to increase production of the gene product. An increase in the copy number of the gene can be obtained by integrating at least one additional copy of the gene into the host genome or by including an amplifiable selectable marker gene with the nucleotide sequence where cells containing amplified copies of the selectable marker gene, and thereby additional copies of the gene, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Preparation of Spent Whole Fermentation Broth

In the methods of the present invention, the preparation of a spent whole fermentation broth of a recombinant microorganism can be achieved using any cultivation method known in the art resulting in the expression of a plant cell wall polysaccharide degrading or converting enzyme. Fermentation may, therefore, be understood as comprising shake flask cultivation, small- or large-scale fermentation (including continuous, batch, fed-batch, or solid state fermentations) in laboratory or industrial fermenters performed in a suitable medium and under conditions allowing the cellulase to be expressed or isolated. The term "spent whole fermentation broth" is defined herein as unfractionated contents of fermentation material that includes culture medium, extracellular proteins (e.g., enzymes), and cellular biomass. It is understood that the term "spent whole fermentation broth" also encompasses cellular biomass that has been lysed or permeabilized using methods well known in the art.

Generally, the recombinant microorganism is cultivated in a nutrient medium suitable for production of enzymes having plant cell wall degrading or converting activity. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). Temperature ranges and other conditions suitable for growth and cellulase production are known in the art (see, e.g., Bailey, J. E., and Ollis, D. F., Biochemical Engineering Fundamentals, McGraw-Hill Book Company, NY, 1986).

The enzymes may be detected using methods known in the art that are specific for the polypeptides, for example, as described supra.

In the methods of the present invention, the spent whole fermentation broth is preferably used "as is" without any processing or minimal treatment such as refrigeration to preserve activity, heat treatment to prvent or decrease organism viability, or addition of chemical agents that prevent or decrease organism viability.

The cellulose-degrading activity of the spent whole fermentation broth may be determined using carboxymethyl cellulose (CMC) as a substrate. Hydrolysis of carboxymethyl cellulose (CMC) decreases the viscosity of the assay mixture, which may be determined by a vibration viscosimeter (e.g., MIVI 3000 from Sofraser, France). Determination of cellulose-degrading activity, measured in terms of Cellulase Viscosity Unit (CEVU), quantifies the amount of catalytic activity present in the spent whole fermentation broth by measuring the ability of the sample to reduce the viscosity of a solution of carboxymethyl cellulose (CMC). The assay is carried out at 40° C.; pH 9.0; 0.1M phosphate buffer; time 30 minutes; CMC substrate (33.3 g/L carboxymethyl cellulose Hercules 7 LFD); enzyme concentration approx. 3.3-4.2 CEVU/ml. The CEVU activity is calculated relative to a declared enzyme standard, such as Celluzyme™ Standard 17-1194 (obtained from Novozymes A/S, Bagsværd, Denmark).

Other enzyme activities can be measured as described herein.

Supplements

In the methods of the present invention, the spent whole fermentation broth may be supplemented with one or more enzyme activities not expressed by the recombinant microorganism to improve the degradation or conversion of plant cell wall polysaccharides.

Preferred additional enzymes include, but are not limited to, endoglucanase (cellulase), cellobiohydrolase, beta-glucosidase, endo-beta-1,3(4)-glucanase, glucohydrolase, xyloglucanase, xylanase, xylosidase, alpha-arabinofuranosidase, alpha-glucuronidase, acetyl xylan esterase, mannanase, mannosidase, alpha-galactosidase, mannan acetyl esterase, galactanase, arabinanase, pectate lyase, pectin lyase, pectate lyase, polygalacturonase, pectin acetyl esterase, pectin methyl esterase, alpha-arabinofuranosidase, beta-galactosidase, galactanase, arabinanase, alpha-arabinofuranosidase, rhamnogalacturonase, rhamnogalacturonan lyase, rhamnogalacturonan acetyl esterase, xylogalacturonosidase, xylogalacturonase, rhamnogalacturonan lyase, lignin peroxidases, manganese-dependent peroxidases, hybrid peroxidases, with combined properties of lignin peroxidases and manganese-dependent peroxidases, and laccases.

The enzymes may be obtained from a suitable microbial or plant source or by recombinant means as described herein or may be obtained from commercial sources.

The additional enzyme(s) added as a supplement to the spent whole broth may be used "as is" or may be purified. The term "as is" as used herein refers to an enzyme preparation produced by fermentation that undergoes no or minimal recovery and/or purification. The term "purified" as used herein covers enzymes free from other components from the organism from which it is obtained. The term "purified" also covers enzymes free from components from the native organism from which it is obtained. The enzymes may be purified, with only minor amounts of other proteins being present. The term "purified" as used herein also refers to removal of other components, particularly other proteins and most particularly other enzymes present in the cell of origin of the enzyme. The enzyme may be "substantially pure," that is, free from other components from the organism in which it is produced, that is, for example, a host organism for enzymes produced by recombinant means. In preferred aspect, the enzymes are at least 20% pure, preferably at least 40% pure, more preferably at least 60% pure, more preferably at least 80% pure, even more preferably at least 90% pure, most preferably at least 95% pure, and even most preferably at least 99% pure, as determined by SDS-PAGE.

Where the enzyme(s) is obtained from a suitable microbial or plant source or by recombinant means, the enzyme may be recovered using recovery methods well known in the art. For example, the enzyme may be recovered from a nutrient medium by conventional procedures including, but not limited to, centrifugation, filtration, extraction, spray-drying, evaporation, or precipitation.

The enzyme(s) may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

The enzymes may also be obtained from commercial sources.

Examples of cellulases suitable for use in the present invention include, for example, CELLUCLAST™ (available from Novozymes A/S), NOVOZYM™ 188 (available from Novozymes A/S). Other commercially available preparations comprising cellulase which may be used include CELLUZYME™, CEREFLO™ and ULTRAFLO™ (Novozymes A/S), LAMINEX™ and SPEZYME™ CP (Genencor Int.) and ROHAMENT™ 7069 W (Röhm GmbH). The cellulase enzymes are added in amounts effective from about 0.001 to 5.0% wt. of solids, more preferably from about 0.025% to 4.0% wt. of solids, and most preferably from about 0.005% to 2.0% wt. of solids.

Preferred commercially available preparations comprising xylanase include SHEARZYME®, BIOFEED WHEAT®, BIO-FEED Plus® L, CELLUCLAST®, ULTRAFLO®, VISCOZYME®, PENTOPAN MONO® BG, PULPZYME® HC (Novozymes A/S); LAMINEX®, SPEZYME® CP (Genencor Int.). The hemicellulase is preferably added in an amount effective of from about 0.001 to 5.0% wt. of solids, more preferably from about 0.025 to 4.0% wt. of solids, and most preferably from about 0.005 to 2.0% wt. of solids.

A preferred commercially available preparation comprising hemicellulase includes VISCOZYME™ (Novozymes A/S). The hemicellulase enzymes are added in amounts effective from about 0.001 to 5.0% wt. of solids, more preferably from about 0.025% to 4.0% wt. of solids, and most preferably from about 0.005% to 2.0% wt. of solids.

Preferred commercial lipases include LECITASE™, LIPOLASE™ and LIPEX™ (Novozymes A/S, Denmark) and G AMANO™ 50 (Amano). Lipases are preferably added or present in amounts from about 1 to 400 LU/g DS, preferably 1 to 10 LU/g DS, and more preferably 1 to 5 LU/g DS.

Preferred commercial phospholipases include LECITASE™ and LECITASE™ ULTRA (Novozymes A/S, Denmark).

Preferred commercial proteases include ALCALASE™, SAVINASE™, and NEUTRASE™ (Novozymes A/S), GC106 (Genencor Int, Inc.), and NOVOZYM™ 50006 (Novozymes A/S).

The additional enzyme(s) used in the present invention may be in any form suitable for use in the processes described herein, such as, e.g., in the form of a dry powder or granulate, a non-dusting granulate, a liquid, a stabilized liquid, or a protected enzyme. Granulates may be produced, e.g., as disclosed in U.S. Pat. Nos. 4,106,991 and 4,661,452, and may optionally be coated by process known in the art. Liquid enzyme preparations may, for instance, be stabilized by adding stabilizers such as a sugar, a sugar alcohol or another polyol, lactic acid or another organic acid according to established process. Protected enzymes may be prepared according to the process disclosed in EP 238,216.

Processing of Plant Cell Wall Polysaccharides

The methods of the present invention may be used in the production of monosaccharides, disaccharides, and polysaccharides as chemical or fermentation feedstocks from biomass for the production of organic products, chemicals and fuels, plastics, and other products or intermediates. In particular, the value of processing residues (dried distillers grain, spent grains from brewing, sugarcane bagasse, etc.) can be increased by partial or complete solubilization of cellulose or hemicellulose. In addition to ethanol, some commodity and specialty chemicals that can be produced from cellulose and hemicellulose include xylose, acetone, acetate, glycine, lysine, organic acids (e.g., lactic acid), 1,3-propanediol, butanediol, glycerol, ethylene glycol, furfural, polyhydroxyalkanoates, cis, cis-muconic acid, and animal feed (Lynd, L. R., Wyman, C. E., and Gerngross, T. U., 1999, Biocommodity engineering, *Biotechnol. Prog.*, 15: 777-793; Philippidis, G. P., 1996, Cellulose bioconversion technology, in *Handbook on Bioethanol: Production and Utilization*, Wyman, C. E., ed., Taylor & Francis, Washington, D.C., 179-212; and Ryu, D. D. Y., and Mandels, M., 1980, Cellulases: biosynthesis and applications, *Enz. Microb. Technol.*, 2: 91-102). Potential coproduction benefits extend beyond the synthesis of multiple organic products from fermentable carbohydrate. Lignin-rich residues remaining after biological processing of a plant cell wall polysaccharide can be converted to lignin-obtained chemicals, or used for power production (Lynd et al., 1999, supra; Philippidis, 1996, supra; Ryu and Mandels, 1980, supra).

Conventional methods used to process the plant cell wall polysaccharides in accordance with the methods of the present invention are well understood to those skilled in the art. The methods of the present invention may be implemented using any conventional biomass processing apparatus configured to operate in accordance with the invention.

Such an apparatus may include, but is not limited to, a batch-stirred reactor, a continuous flow stirred reactor with ultrafiltration, a continuous plug-flow column reactor (Gusakov, A. V., and Sinitsyn, A. P., 1985, Kinetics of the enzymatic hydrolysis of cellulose: 1. A mathematical model for a batch reactor process, *Enz. Microb. Technol.*, 7: 346-352), an attrition reactor (Ryu, S. K., and Lee, J. M., 1983, Bioconversion of waste cellulose by using an attrition bioreactor, *Biotechnol. Bioeng.*, 25: 53-65), or a reactor with intensive stirring induced by electromagnetic field (Gusakov, A. V., Sinitsyn, A. P., Davydkin, I. Y., Davydkin, V. Y., Protas, O. V., 1996, Enhancement of enzymatic cellulose hydrolysis using a novel type of bioreactor with intensive stirring induced by electromagnetic field, *Appl. Biochem. Biotechnol.*, 56:141-153).

The conventional methods include, but are not limited to, saccharification, fermentation, separate hydrolysis and fermentation (SHF), simultaneous saccharification and fermentation (SSF), simultaneous saccharification and cofermentation (SSCF), hybrid hydrolysis and fermentation (HHF), and direct microbial conversion (DMC).

SHF uses separate process steps to first enzymatically hydrolyze cellulose to glucose and then ferment glucose to ethanol. In SSF, the enzymatic hydrolysis of cellulose and the fermentation of glucose to ethanol are combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF includes the coferementation of multiple sugars (Sheehan, J., and Himmel, M., 1999, Enzymes, energy and the environment: A strategic perspective on the U.S. Department of Energy's research and development activities for bioethanol, *Biotechnol. Prog.*, 15: 817-827). Hybrid hydrolysis and fermentation (HHF) process includes two separate steps carried out in the same reactor but at different temperatures, high temperature enzymatic saccharification followed by SSF at a lower temperature that the fermentation strain can tolerate. DMC combines all three processes (cellulase production, cellulose hydrolysis, and fermentation) in one step (Lynd, L. R., Weimer, P. J., van Zyl, W. H., and Pretorius, I. S., 2002, Microbial cellulose utilization: Fundamentals and biotechnology, *Microbiol. Mol. Biol. Reviews*, 66: 506-577).

"Fermentation" or "fermentation process" refers to any fermentation process or any process comprising a fermentation step. A fermentation process includes, without limitation, fermentation processes used to produce fermentation products including alcohols (e.g., arabinitol, butanol, ethanol, glycerol, methanol, 1,3-propanediol, sorbitol, and xylitol); organic acids (e.g., acetic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, propionic acid, succinic acid, and xylonic acid); ketones (e.g., acetone); amino acids (e.g., aspartic acid, glutamic acid, glycine, lysine, serine, and threonine); and/or gases (e.g., methane, hydrogen ($H_2$), carbon dioxide ($CO_2$), and carbon monoxide (CO)). Fermentation processes also include fermentation processes used in the consumable alcohol industry (e.g., beer and wine), dairy industry (e.g., fermented dairy products), leather industry, and tobacco industry.

The present invention also relates to methods for producing one or more organic substances, comprising: (a) saccharifying plant cell wall polysaccharides with an effective amount of a spent whole fermentation broth of a recombinant microorganism, wherein the recombinant microorganism expresses one or more heterologous genes encoding enzymes which degrade or convert the plant cell wall polysaccharides into saccharified material; (b) fermenting the saccharified material of step (a) with one or more fermenting microoganisms; and (c) recovering the one or more organic substances from the fermentation.

The organic substance can be any substance derived from the fermentation. In a preferred aspect, the organic substance is an alcohol. It will be understood that the term "alcohol" encompasses an organic substance that contains one or more hydroxyl moieties. In a more preferred aspect, the alcohol is arabinitol. In another more preferred aspect, the alcohol is butanol. In another more preferred aspect, the alcohol is ethanol. In another more preferred aspect, the alcohol is glycerol. In another more preferred aspect, the alcohol is methanol. In another more preferred aspect, the alcohol is 1,3-propanediol. In another more preferred aspect, the alcohol is sorbitol. In another more preferred aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, *Appl. Microbiol. Biotechnol.* 59: 400-408; Nigam, P., and Singh, D., 1995, Processes for fermentative production of xylitol—a sugar substitute, *Process Biochemistry* 30 (2): 117-124; Ezeji, T. C., Qureshi, N. and Blaschek, H. P., 2003, Production of acetone, butanol and ethanol by *Clostridium beijerinckii* BA101 and in situ recovery by gas stripping, *World Journal of Microbiology and Biotechnology* 19 (6): 595-603.

In another preferred aspect, the organic substance is an organic acid. In another more preferred aspect, the organic acid is acetic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo-D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another preferred aspect, the organic acid is 3-hydroxypropionic acid. In another more preferred aspect, the organic acid is itaconic acid. In another more preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen, R., and Lee, Y. Y., 1997, Membrane-mediated extractive fermentation for lactic acid production from cellulosic biomass, *Appl. Biochem. Biotechnol.* 63-65: 435-448.

In another preferred aspect, the organic substance is a ketone. It will be understood that the term "ketone" encompasses an organic substance that contains one or more ketone moieties. In another more preferred aspect, the ketone is acetone. See, for example, Qureshi and Blaschek, 2003, supra.

In another preferred aspect, the organic substance is an aldehyde. In another more preferred aspect, the aldehyde is a furfural.

In another preferred aspect, the organic substance is an amino acid. In another more preferred aspect, the organic acid is aspartic acid. In another more preferred aspect, the amino acid is alanine. In another more preferred aspect, the amino acid is arginine. In another more preferred aspect, the amino acid is asparagine. In another more preferred aspect, the amino acid is glutamine. In another more preferred aspect, the amino acid is glutamic acid. In another more preferred aspect, the amino acid is glycine. In another more preferred aspect, the amino acid is histidine. In another more preferred aspect, the amino acid is isoleucine. In another more preferred aspect, the amino acid is leucine. In another more preferred aspect, the amino acid is lysine. In another more preferred aspect, the amino acid is methionine. In another more preferred aspect, the amino acid is phenylalanine. In another more preferred aspect, the amino acid is proline. In another more preferred aspect, the amino acid is serine. In another more preferred aspect, the amino acid is threonine. In another more preferred aspect, the amino acid is tryptophan. In another more preferred aspect, the amino acid is tyrosine. In another more preferred aspect, the amino acid is valine. See, for example, Richard, A., and Margaritis, A., 2004, Empirical modeling of batch fermentation kinetics for poly(glutamic acid) production and other microbial biopolymers, *Biotechnology and Bioengineering* 87 (4): 501-515.

In another preferred aspect, the organic substance is a gas. In another more preferred aspect, the gas is methane ($CH_4$). In another more preferred aspect, the gas is hydrogen ($H_2$). In another more preferred aspect, the gas is carbon dioxide ($CO_2$). In another more preferred aspect, the gas is carbon monoxide (CO). See, for example, Kataoka, N., A. Miya, and K. Kiriyama, 1997, Studies on hydrogen production by continuous culture system of hydrogen-producing anaerobic bacteria, *Water Science and Technology* 36 (6-7): 41-47; and Gunaseelan V. N. in *Biomass and Bioenergy*, Vol. 13 (1-2), pp. 83-114, 1997, Anaerobic digestion of biomass for methane production: A review.

Production of an organic substance from polysaccharides, such as cellulose, typically requires four major steps. These four steps are pretreatment, enzymatic hydrolysis, fermentation, and recovery. Exemplified below is a process for producing ethanol, but it will be understood that similar processes can be used to produce other organic substances, for example, the substances described above.

Pretreatment.

In the pretreatment or pre-hydrolysis step, the cellulosic material is heated to break down the lignin and carbohydrate structure to make the cellulose fraction accessible to cellulolytic enzymes. The heating is performed either directly with steam or in slurry where a catalyst may also be added to the material to speed up the reactions. Catalysts include strong acids, such as sulfuric acid and $SO_2$, or alkali, such as sodium hydroxide. The purpose of the pre-treatment stage is to facilitate the penetration of the enzymes and microorganisms. Cellulosic biomass may also be subject to a hydrothermal steam explosion pre-treatment (See U.S. Patent Application No. 20020164730).

Saccharification.

In the enzymatic hydrolysis step, also known as saccharification, enzymes as described herein are added to the pretreated material to convert the cellulose fraction to glucose and/or other sugars. The saccharification is generally performed in stirred-tank reactors or fermentors under controlled pH, temperature, and mixing conditions. A saccharification step may last up to 200 hours. Saccharification may be carried out at temperatures from about 30° C. to about 65° C., in particular around 50° C., and at a pH in the range between about 4 and about 5, especially around pH 4.5. To produce glucose that can be metabolized by yeast, the hydrolysis is typically performed in the presence of a beta-glucosidase.

Fermentation.

In the fermentation step, sugars, released from the plant cell wall polysaccharides as a result of the pretreatment and enzymatic hydrolysis steps, are fermented to one or more organic substances, e.g., ethanol, by a fermenting organism, such as yeast, or fermenting organisms. The fermentation can also be carried out simultaneously with the enzymatic hydrolysis in the same vessels, again under controlled pH, temperature and mixing conditions. When saccharification and fermentation are performed simultaneously in the same vessel, the process is generally termed simultaneous saccharification and fermentation or SSF.

Any suitable plant cell wall biomass may be used in a fermentation process of the present invention. The plant cell wall biomass is generally selected based on the desired fermentation product(s) and the process employed, as well known in the art. Examples of substrates suitable for use in the methods of the present invention, include cellulose-containing materials, such as wood or plant residues or low molecular sugars $DP_{1-3}$ obtained from processed plant cell wall polysaccharides that can be metabolized by the fermenting microorganism, and which may be supplied by direct addition to the fermentation media.

The term "fermentation medium" will be understood to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism suitable for use in a desired fermentation process. Suitable fermenting microorganisms according to the invention are able to ferment, i.e., convert, sugars, such as glucose, xylose, arabinose, mannose, galactose, or oligosaccharides, directly or indirectly into the desired fermentation product(s). Examples of fermenting microorganisms include fungal organisms, such as yeast. Preferred yeast include strains of *Saccharomyces* spp., and in particular, *Saccharomyces cerevisiae*. Commercially available yeast include, e.g., Red Star®/Lesaffre Ethanol Red (available from Red Star/Lesaffre, USA) FALI (available from Fleischmann's Yeast, a division of Burns Philp Food Inc., USA), SUPERSTART (available from Alltech), GERT STRAND (available from Gert Strand AB, Sweden) and FERMIOL (available from DSM Specialties). Other microorganisms may also be used depending the fermentation product(s) desired. These other microorganisms include Gram positive bacteria, e.g., *Lactobacillus* such as *Lactobacillus lactis*, *Propionibacterium* such as *Propionibacterium freudenreichii*; *Clostridium* sp. such as *Clostridium butyricum*, *Clostridium beijerinckii*, *Clostridium diolis*, *Clostridium acetobutylicum*, and *Clostridium thermocellum*; Gram negative bacteria, e.g., *Zymomonas* such as *Zymomonas mobilis*; and filamentous fungi, e.g., *Rhizopus oryzae*.

In a preferred aspect, the yeast is a *Saccharomyces* sp. In a more preferred aspect, the yeast is *Saccharomyces cerevisiae*. In another more preferred aspect, the yeast is Saccharomyces distaticus. In another more preferred aspect, the yeast is *Saccharomyces uvarum*. In another preferred aspect, the yeast is a *Kluyveromyces*. In another more preferred aspect, the yeast is *Kluyveromyces marxianus*. In another more preferred aspect, the yeast is *Kluyveromyces fragilis*. In another preferred aspect, the yeast is a *Candida*. In another more preferred aspect, the yeast is *Candida pseudotropicalis*. In another more preferred aspect, the yeast is *Candida brassicae*. In another more preferred aspect, the yeast is a *Clavispora*. In another more preferred aspect, the yeast is *Clavispora lusitaniae*. In another more preferred aspect, the yeast is *Clavispora opuntiae*. In another preferred aspect, the yeast is a *Pachysolen*. In another more preferred aspect, the yeast is *Pachysolen tannophilus*. In another preferred aspect, the yeast is a *Bretannomyces*. In another more preferred aspect, the yeast is *Bretannomyces clausenii* (Philippidis, G. P., 1996, Cellulose bioconversion technology, in *Handbook on Bioethanol: Production and Utilization*, Wyman, C. E., ed., Taylor & Francis, Washington, D.C., 179-212).

Bacteria that can efficiently ferment glucose to ethanol include, for example, *Zymomonas mobilis* and *Clostridium thermocellum* (Philippidis, 1996, supra).

It is well known in the art that the organisms described above can also be used to produce other organic substances, as described herein.

The cloning of heterologous genes into *Saccharomyces cerevisiae* (Chen, Z., Ho, N. W. Y., 1993, Cloning and improving the expression of *Pichia stipitis* xylose reductase gene in *Saccharomyces cerevisiae*, *Appl. Biochem. Biotechnol.*, 39-40: 135-147; Ho, N. W. Y., Chen, Z, Brainard, A. P., 1998, Genetically engineered *Saccharomyces* yeast capable of effectively cofermenting glucose and xylose, *Appl. Environ. Microbiol.* 64: 1852-1859), or in bacteria such as *Escherichia coli* (Beall, D. S., Ohta, K., Ingram, L. O., 1991, Parametric studies of ethanol production from xylose and other sugars by recombinant *Escherichia coli*, *Biotech. Bioeng.* 38: 296-303), *Klebsiella oxytoca* (Ingram, L. O., Gomes, P. F., Lai, X., Moniruzzaman, M., Wood, B. E., Yomano, L. P., York, S. W., 1998, Metabolic engineering of bacteria for ethanol production, *Biotechnol. Bioeng.*, 58: 204-214), and *Zymomonas mobilis* (Zhang, M., Eddy, C., Deanda, K., Finkelstein, M., and Picataggio, S., 1995, Metabolic engineering of a pentose metabolism pathway in ethanologenic *Zymomonas mobilis*, *Science*, 267: 240-243; Deanda, K., Zhang, M., Eddy, C., and Picataggio, S., 1996, Development of an arabinose-fermenting *Zymomonas mobilis* strain by metabolic pathway engineering, *Appl. Environ. Microbiol*, 62: 4465-4470) has led to the construction of organisms capable of converting hexoses and pentoses to ethanol (cofermentation).

Yeast or other microorganisms are typically added to the hydrolysate and the fermentation is allowed to proceed for 24-96 hours, such as 35-60 hours. The temperature is typically between 26-40° C., in particular at about 32° C., and at pH 3-6, in particular about pH 4-5.

In a preferred aspect, yeast is applied to the hydrolysate and the fermentation proceeds for 24-96 hours, such as typically 35-60 hours. In another preferred aspect, the temperature is generally between 26-40° C., in particular about 32° C., and the pH is generally from pH 3 to 6, preferably about pH 4-5. Yeast cells are preferably applied in amounts of $10^5$ to $10^{12}$, preferably from $10^7$ to $10^{10}$, especially $5 \times 10^7$ viable yeast count per ml of fermentation broth. During the ethanol producing phase the yeast cell count should preferably be in the range from $10^7$ to $10^{10}$, especially around $2 \times 10^8$. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

The most widely used process in the art is the simultaneous saccharification and fermentation (SSF) process where there is no holding stage for the saccharification, meaning that the fermentating microorganism and enzyme are added together.

For ethanol production, following the fermentation the mash is distilled to extract the ethanol. The ethanol obtained according to the process of the invention may be used as, e.g., fuel ethanol; drinking ethanol, i.e., potable neutral spirits, or industrial ethanol.

A fermentation stimulator may be used in combination with any of the enzymatic processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, e.g., Alfenore et al., Improving ethanol production and viability of *Saccharomyces cerevisiae* by a vitamin feeding strategy during fed-batch process," Springer-Verlag (2002), which is hereby incorporated by reference. Examples of minerals include minerals and mineral salts that can supply nutrients comprising P, K, Mg, S, Ca, Fe, Zn, Mn, and Cu.

Recovery.

Following the fermentation, the organic substance of interest is recovered from the mash by any method known in the art. Such methods include, but are not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, distillation, or extraction. For example, in an ethanol fermentation, the alcohol is separated from the fermented plant cell wall polysaccharides and purified by conventional methods of distillation. Ethanol with a purity of up to about 96 vol. % ethanol can be obtained, which can be used as, e.g., fuel ethanol; drinking ethanol, i.e., potable neutral spirits; or industrial ethanol.

The present invention is further described by the following examples which should not be construed as limiting the scope of the invention.

EXAMPLES

Materials

Chemicals used as buffers and substrates were commercial products of at least reagent grade.

Strains

*Trichoderma reesei* (synonym *Hypocrea jecorina*) RutC30 was used as the source for cellulase. *Trichoderma reesei* RutC30 is available from the American Type Culture Collection (ATCC 56765). *Trichoderma reesei* SMA135-04 is a recombinant derivative of *Trichoderma reesei* RutC30 that harbors multiple copies of the *Aspergillus oryzae* beta-glucosidase gene expressed under the transcriptional control of the *Trichoderma reesei* cbh1 gene promoter.

Example 1

Construction of pAlLo01 Expression Vector

Expression vector pAlL01 was constructed by modifying pBANe6 (U.S. Pat. No. 6,461,837), which comprises a hybrid of the promoters from the genes for *Aspergillus niger* neutral alpha-amylase and *Aspergillus oryzae* triose phosphate isomerase (NA2-tpi promoter), *Aspergillus niger* amyloglucosidase terminator sequence (AMG terminator), and *Aspergillus nidulans* acetamidase gene (amdS). All mutagenesis steps were verified by sequencing using Big-Dye™ terminator chemistry (Applied Biosystems, Inc., Foster City, Calif.). Modification of pBANe6 was performed by first eliminating three Nco I restriction sites at positions 2051, 2722, and 3397 bp from the amdS selection marker by site-directed mutagenesis. All changes were designed to be "silent" leaving the actual protein sequence of the amdS gene product unchanged. Removal of these three sites was performed simultaneously with a GeneEditor™ in vitro Site-Directed Mutagenesis Kit (Promega, Madison, Wis.) according to the manufacturer's instructions using the following primers (underlined nucleotide represents the changed base):

```
AMDS3NcoMut (2050):                  (SEQ ID NO: 1)
5'-GTGCCCCATGATACGCCTCCGG-3'

AMDS2NcoMut (2721):                  (SEQ ID NO: 2)
5'-GAGTCGTATTTCCAAGGCTCCTGACC-3'

AMDS1NcoMut (3396):                  (SEQ ID NO: 3)
5'-GGAGGCCATGAAGTGGACCAACGG-3'
```

A plasmid comprising all three expected sequence changes was then submitted to site-directed mutagenesis, using a QuickChange™ Site-Directed Mutagenesis Kit (Stratagene, La Jolla, Calif.), to eliminate the Nco I restriction site at the end of the AMG terminator at position 1643. The following primers (underlined nucleotide represents the changed base) were used for mutagenesis:

Upper Primer to Mutagenize the AMG Terminator Sequence:

```
5'-                                  (SEQ ID NO: 4)
CACCGTGAAAGCCATGCTCTTTCCTTCGTGTAGAAGACCAGACAG-3'
```

Lower Primer to Mutagenize the AMG Terminator Sequence:

```
5'-                                  (SEQ ID NO: 5)
CTGGTCTTCTACACGAAGGAAAGAGCATGGCTTTCACGGTGTCTG-3'
```

Figure 6:
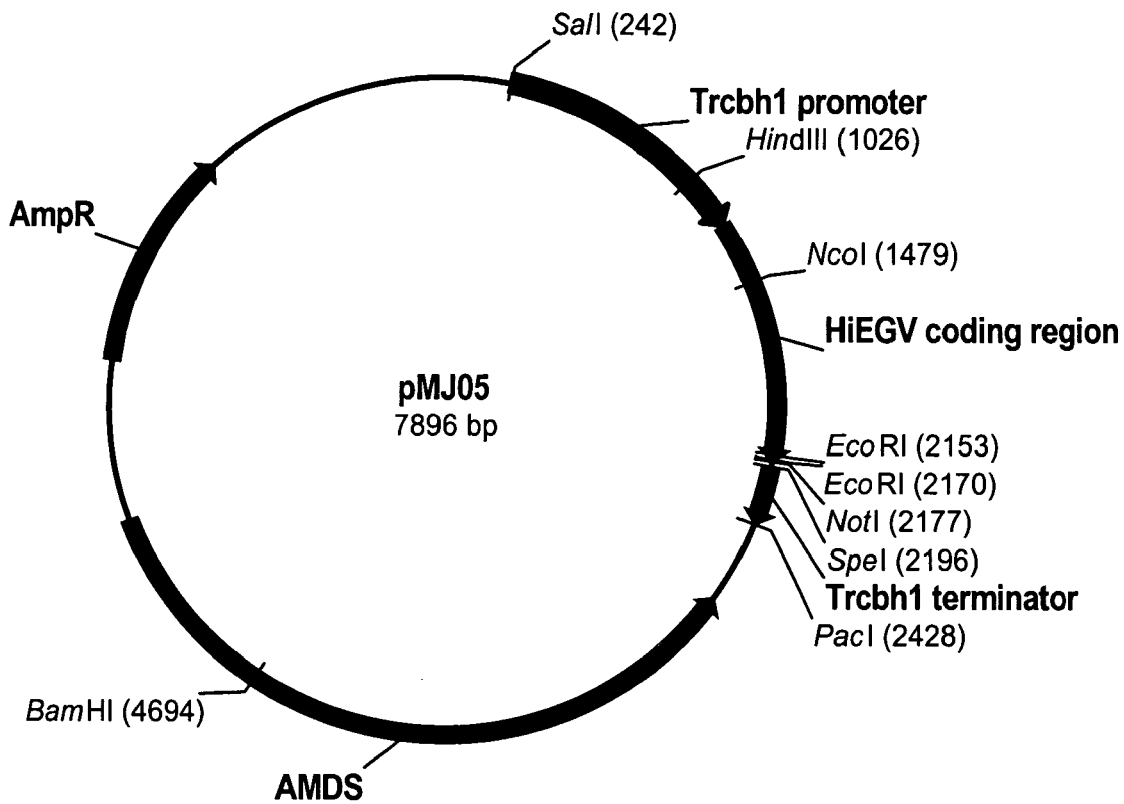
FIG. 6 shows a restriction map of pMJ05.

The last step in the modification of pBANe6 was the addition of a new Nco I restriction site at the beginning of the polylinker using a QuickChange™ Site-Directed Mutagenesis Kit and the following primers (underlined nucleotides represent the changed bases) to yield pAlL01 (FIG. 6).

Upper Primer to Mutagenize the NA2-tpi Promoter:

```
                                     (SEQ ID NO: 6)
5'-CTATATACACAACTGGATTTACCATGGGCCCGCGGCCGCAGATC-3'
```

Lower Primer to Mutagenize the NA2-tpi Promoter:

```
                                     (SEQ ID NO: 7)
5'-GATCTGCGGCCGCGGGCCCATGGTAAATCCAGTTGTGTATATAG-3'
```

Example 2

Construction of pMJ04 Expression Vector

Expression vector pMJ04 was constructed by PCR amplification of the *Trichoderma reesei* exocellobiohydrolase 1 gene (cbh1) terminator from *Trichoderma reesei* RutC30 genomic DNA using primers 993429 (antisense) and 993428 (sense) shown below. The antisense primer was engineered to have a PacI site at the 5'-end and a SpeI site at the 3'-end of the sense primer.

```
Primer 993429 (antisense):            (SEQ ID NO: 8)
5'-AACGTTAATTAAGGAATCGTTTTGTGTTT-3'

Primer 993428 (sense):                (SEQ ID NO: 9)
5'-AGTACTAGTAGCTCCGTGGCGAAAGCCTG-3'
```

*Trichoderma reesei* RutC30 genomic DNA was isolated using a DNeasy Plant Maxi Kit (QIAGEN Inc., Valencia, Calif.).

The amplification reactions (50 μl) were composed of 1× ThermoPol Reaction Buffer (New England BioLabs, Beverly, Mass.), 0.3 mM dNTPs, 100 ng of *Trichoderma reesei* RutC30 genomic DNA, 0.3 μM primer 993429, 0.3 μM primer 993428, and 2 units of Vent polymerase (New England BioLabs, Beverly, Mass.). The reactions were incubated in an Eppendorf Mastercycler 5333 programmed as follows: 30 cycles each for 30 seconds at 94° C., 30 seconds at 55° C., and 30 seconds at 72° C. (15 minute final extension).

The reaction products were isolated on a 1.0% agarose gel using 40 mM Tris base-20 mM sodium acetate-1 mM disodium EDTA (TAE) buffer where a 229 bp product band was excised from the gel and purified using a QIAGEN QIAquick Gel Extraction Kit according to the manufacturer's instructions.

Figure 1:
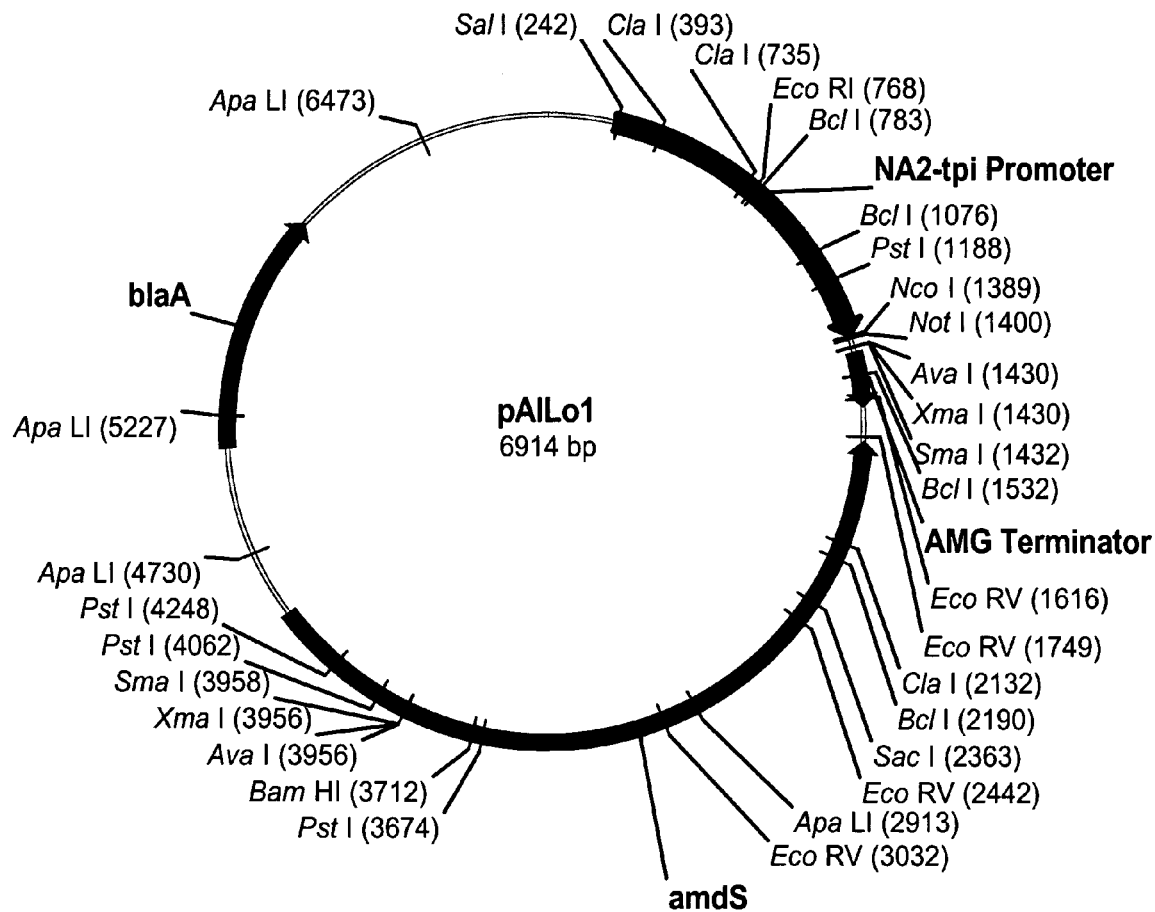
FIG. 1 shows a restriction map of pAlLo01.
Figure 2:
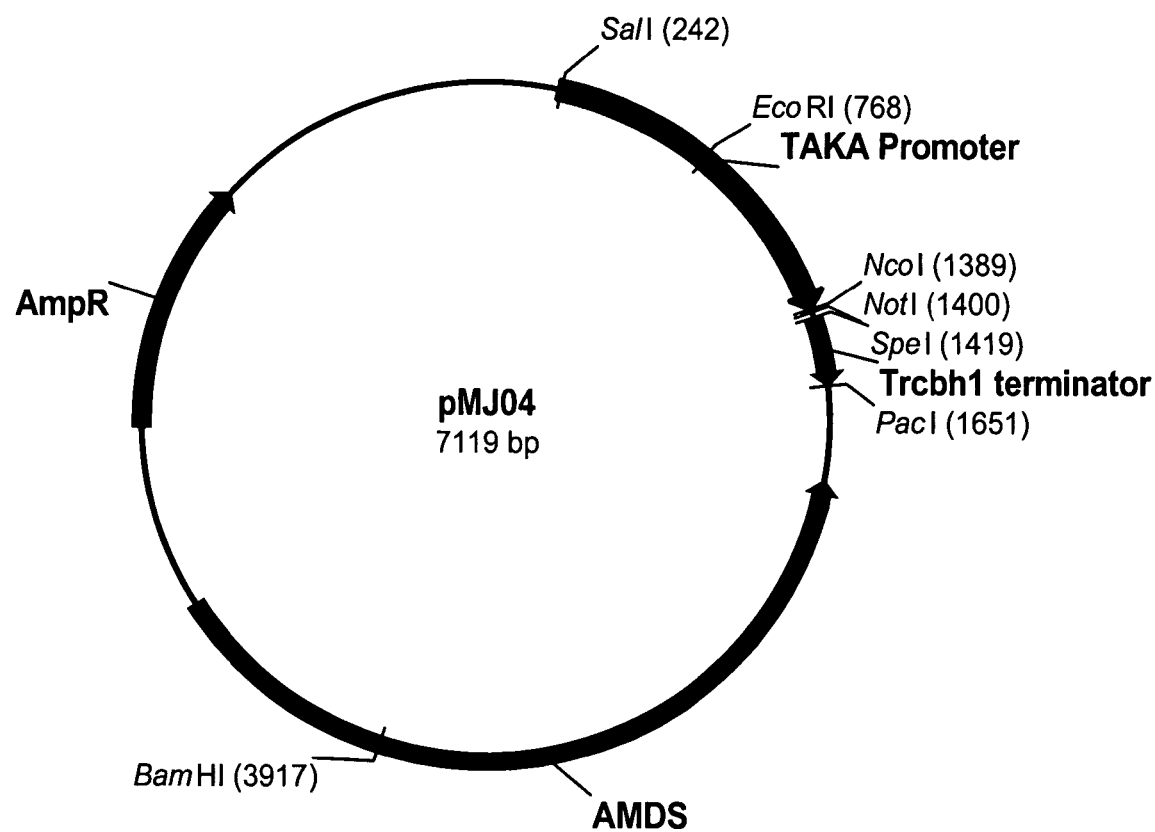
FIG. 2 shows a restriction map of pMJ04.

The resulting PCR fragment was digested with Pac I and Spe I and ligated into pAlLo1 digested with the same restriction enzymes using a Rapid Ligation Kit (Roche, Indianapolis, Ind.), to generate pMJ04 (FIG. 2).

Example 3

Construction of pCaHj568 Expression Vector

Expression plasmid pCaHj568 was constructed from pCaHj170 (U.S. Pat. No. 5,763,254) and pMT2188. Plasmid pCaHj170 comprises the *Humicola insolens* endoglucanase V (EGV) coding region. Plasmid pMT2188 was constructed as follows: The pUC19 origin of replication was PCR amplified from pCaHj483 (WO 98/00529) with primers 142779 and 142780 shown below. Primer 142780 introduces a Bbu I site in the PCR fragment.

```
142779:                               (SEQ ID NO: 10)
5'-TTGAATTGAAAATAGATTGATTTAAAACTTC-3'

142780:                               (SEQ ID NO: 11)
5'-TTGCATGCGTAATCATGGTCATAGC-3'
```

The Expand PCR System (Roche Molecular Biochemicals, Basel, Switserland) was used for the amplification following the manufacturer's instructions for this and the subsequent PCR amplifications. PCR products were separated on an agarose gel and an 1160 bp fragment was isolated and purified using a Jetquick Gel Extraction Spin Kit (Genomed, Wielandstr, Germany).

The URA3 gene was amplified from the general *Saccharomyces cerevisiae* cloning vector pYES2 (Invitrogen, Carlsbad, Calif.) using primers 140288 and 142778 below. Primer 140288 introduces an Eco RI site in the PCR fragment.

```
140288:                               (SEQ ID NO: 12)
5'-TTGAATTCATGGGTAATAACTGATAT-3'

142778:                               (SEQ ID NO: 13)
5'-AAATCAATCTATTTTCAATTCAATTCATCATT-3'
```

PCR products were separated on an agarose gel and an 1126 bp fragment was isolated and purified using a Jetquick Gel Extraction Spin Kit.

The two PCR fragments were fused by mixing and amplifed using primers 142780 and 140288 shown above by overlap method splicing (Horton et al., 1989, *Gene* 77: 61-68). PCR products were separated on an agarose gel and a 2263 bp fragment was isolated and purified using a Jetquick Gel Extraction Spin Kit.

Figure 3:
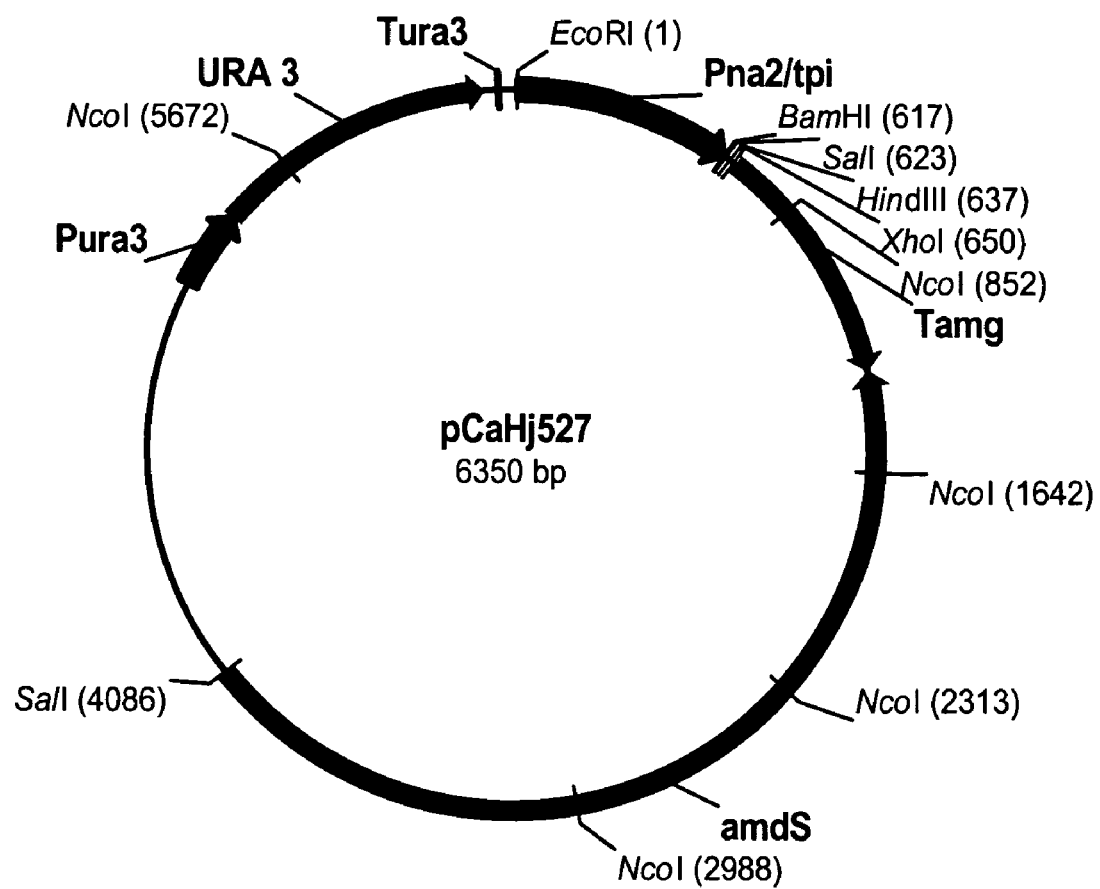
FIG. 3 shows a restriction map of pCaHj527.

The resulting fragment was digested with Eco RI and Bbu I and ligated to the largest fragment of pCaHj483 digested with the same enzymes. The ligation mixture was used to transform pyrF *E. coli* strain DB6507 (ATCC 35673) made competent by the method of Mandel and Higa, 1970, *J. Mol. Biol.* 45: 154. Transformants were selected on solid M9 medium (Sambrook et al., 1989, Molecular Cloning, A Laboratory Manual, 2nd edition, Cold Spring Harbor Laboratory Press) supplemented per liter with 1 g of casamino acids, 500 μg of thiamine, and 10 mg of kanamycin. A plasmid from one transformant was isolated and designated pCaHj527 (FIG. 3).

The NA2/tpi promoter present on pCaHj527 was subjected to site-directed mutagenesis by a simple PCR approach. Nucleotides 134-144 were converted from GTACTAAAACC to CCGTTAAATTT using mutagenic primer 141223:

```
Primer 141223:                        (SEQ ID NO: 14)
5'-GGATGCTGTTGACTCCGGAAATTTAACGGTTTGGTCTTGCATCCC-3'
```

Nucleotides 423-436 were converted from ATGCMTT-TAAACT to CGGCMTTTMCGG using mutagenic primer 141222:

```
Primer 141222:                        (SEQ ID NO: 15)
5'-GGTATTGTCCTGCAGACGGCAATTTAACGGCTTCTGCGAATCGC-3'
```

Figure 4:
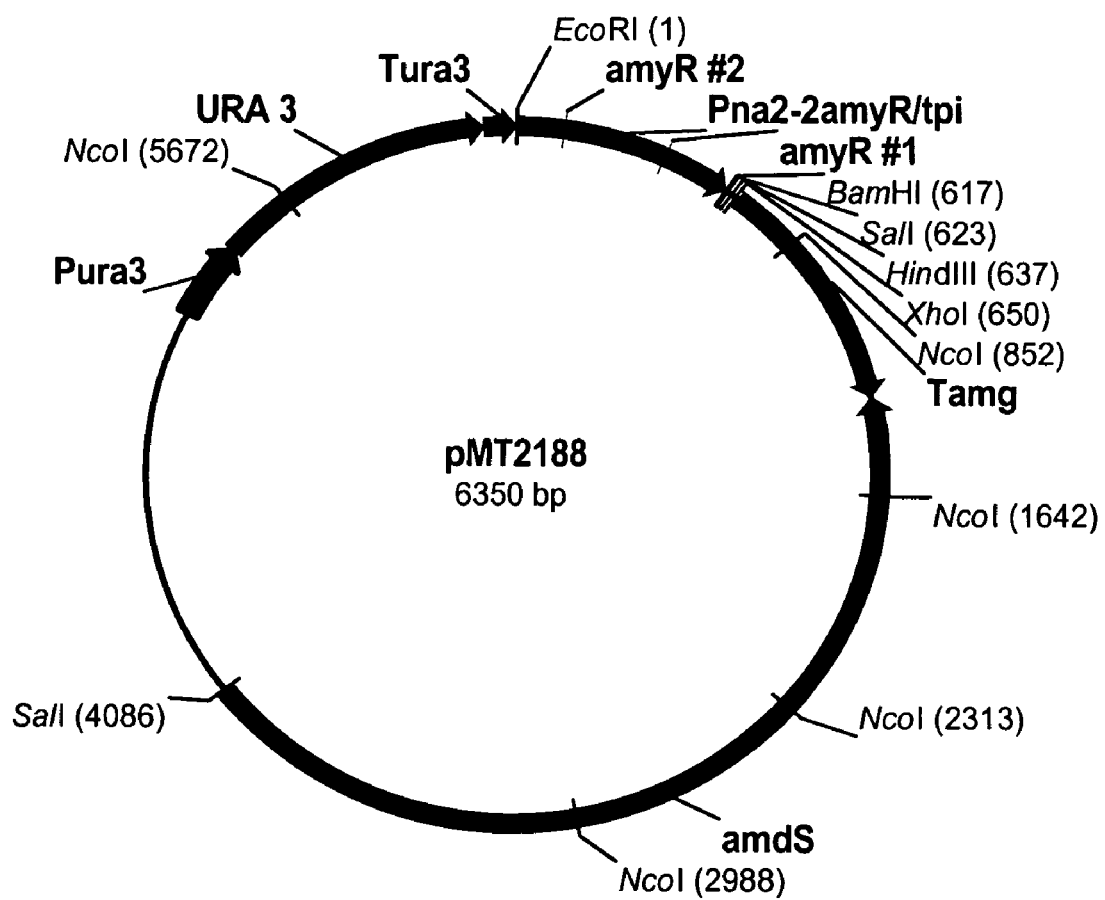
FIG. 4 shows a restriction map of pMT2188.

The resulting plasmid was designated pMT2188 (FIG. 4).

Figure 5:
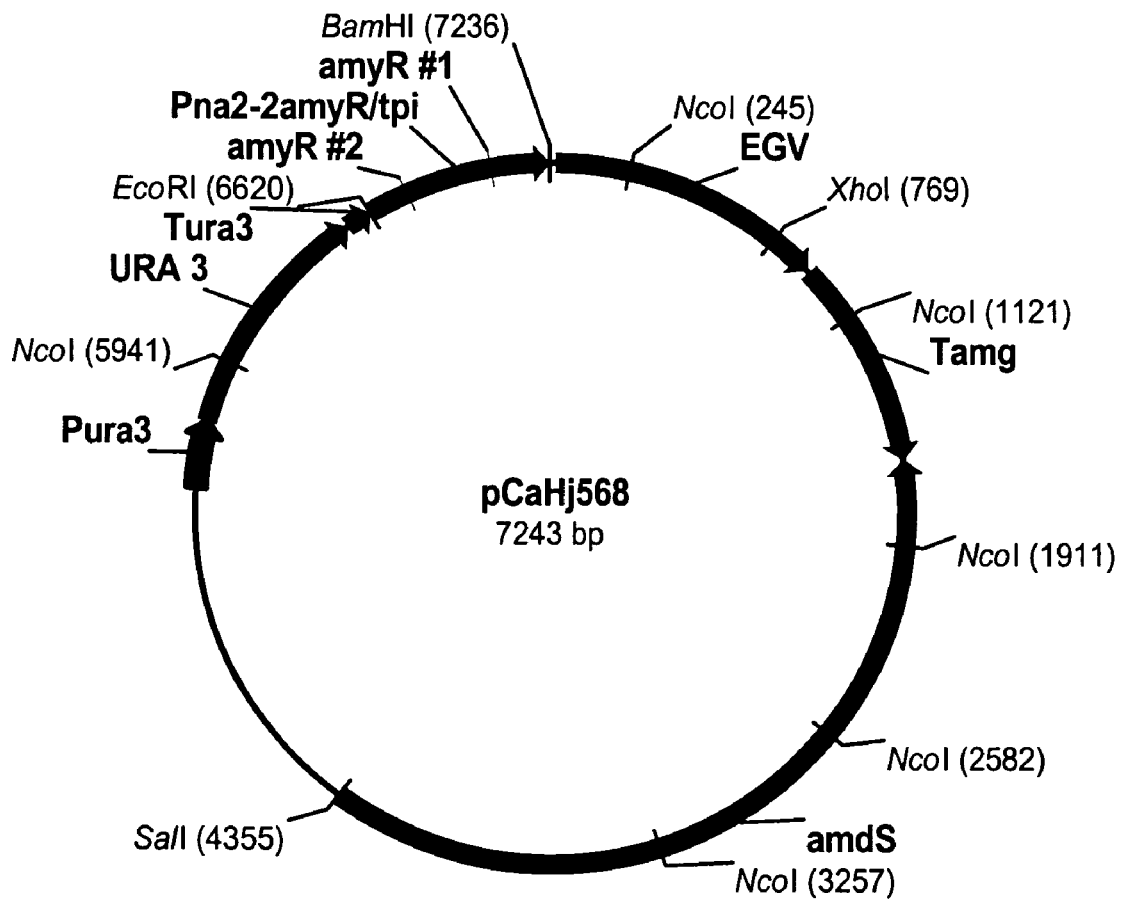
FIG. 5 shows a restriction map of pCaHj568.

The *Humicola insolens* endoglucanase V coding region was transferred from pCaHj170 as a Bam HI-Sal I fragment into pMT2188 digested with Bam HI and Xho I to generate pCaHj568 (FIG. 5).

Example 4

Construction of pMJ05 Expression Vector

Expression vector pMJ05 was constructed by PCR amplifying the 915 bp *Humicola insolens endoglucanase V coding region from pCaHj*568 using primers HiEGV-F and HiEGV-R shown below.

```
HiEGV-F (sense):                      (SEQ ID NO: 16)
5'-AAGCTTAAGCATGCGTTCCTCCCCCCTCC-3'

HiEGV-R (antisense):                  (SEQ ID NO: 17)
5'-CTGCAGAATTCTACAGGCACTGATGGTACCAG-3'
```

The amplification reactions (50 μl) were composed of 1× ThermoPol Reaction Buffer, 0.3 mM dNTPs, 10 ng/μl pCaHj568 plasmid, 0.3 μM HiEGV-F primer, 0.3 μM HiEGV-R primer, and 2 U of Vent polymerase. The reactions were incubated in an Eppendorf Mastercycler 5333 programmed as follows: 5 cycles each for 30 seconds at 94° C., 30 seconds at 50° C., and 60 seconds at 72° C., followed by 25 cycles each for 30 seconds at 94° C., 30 seconds at 65° C., and 120 seconds at 72° C. (5 minute final extension). The reaction products were isolated on a 1.0% agarose gel using TAE buffer where a 937 bp product band was excised from the gel and purified using a QIAquick Gel Extraction Kit according to the manufacturer's instructions.

This 937 bp purified fragment was used as template DNA for subsequent amplifications using the following primers:

```
HiEGV-R (antisense):                         (SEQ ID NO: 18)
5'-CTGCAGAATTCTACAGGCACTGATGGTACCAG-3'

HiEGV-F-overlap (sense):                     (SEQ ID NO: 19)
5'-ACCGCGGACTGCGCATCATGCGTTCCTCCCCCTCC-3'
```

Primer sequences in italics are homologous to 17 bp of the *Trichoderma reesei* cbh1 promoter and underlined primer sequences are homologous to 29 bp of the *Humicola insolens* endoglucanase V coding region. The 36 bp overlap between the promoter and the coding sequence allowed precise fusion of the 994 bp fragment comprising the *Trichoderma reesei* cbh1 promoter to the 918 bp fragment comprising the *Humicola insolens* endoglucanase V open reading frame.

The amplification reactions (50 µl) were composed of 1× ThermoPol Reaction Buffer, 0.3 mM dNTPs, 1 ul of 937 bp purified PCR fragment, 0.3 µM HiEGV-F-overlap primer, 0.3 µM HiEGV-R primer, and 2 U of Vent polymerase. The reactions were incubated in an Eppendorf Mastercycler 5333 programmed as follows: 5 cycles each for 30 seconds at 94° C., 30 seconds at 50° C., and 60 seconds at 72° C., followed by 25 cycles each for 30 seconds at 94° C., 30 seconds at 65° C., and 120 seconds at 72° C. (5 minute final extension). The reaction products were isolated on a 1.0% agarose gel using TAE buffer where a 945 bp product band was excised from the gel and purified using a QIAquick Gel Extraction Kit according to the manufacturer's instructions.

A separate PCR was performed to amplify the *Trichoderma reesei* cbh1 promoter sequence extending from 994 bp upstream of the ATG start codon of the gene from *Trichoderma reesei* RutC30 genomic DNA using the following primers (sense primer was engineered to have a Sal I restriction site at the 5'-end):

```
TrCBHIpro-F (sense):                         (SEQ ID NO: 20)
5'-AAACGTCGACCGAATGTAGGATTGTTATC-3'

TrCBHIpro-R (antisense):                     (SEQ ID NO: 21)
5'-GATGCGCAGTCCGCGGT-3'
```

The amplification reactions (50 µl) were composed of 1× ThermoPol Reaction Buffer, 0.3 mM dNTPs, 100 ng of *Trichoderma reesei* RutC30 genomic DNA, 0.3 µM TrCBHIpro-F primer, 0.3 µM TrCBHIpro-R primer, and 2 U of Vent polymerase. The reactions were incubated in an Eppendorf Mastercycler 5333 programmed as follows: 30 cycles each for 30 seconds at 94° C., 30 seconds at 55° C., and 120 seconds at 72° C. (5 minute final extension). The reaction products were isolated on a 1.0% agarose gel using TAE buffer where a 998 bp product band was excised from the gel and purified using a QIAquick Gel Extraction Kit according to the manufacturer's instructions.

The 998 bp purified PCR fragment was used as template DNA for subsequent amplifications using the following primers:

```
TrCBHIpro-F:                                 (SEQ ID NO: 22)
5'-AAACGTCGACCGAATGTAGGATTGTTATC-3'

TrCBHIpro-R-overlap:                         (SEQ ID NO: 23)
5'-GGAGGGGGGAGGAACGCATGATGCGCAGTCCGCGGT-3'
```

Sequences in italics are homologous to 17 bp of the *Trichoderma reesei* cbh1 promoter and underlined sequences are homologous to 29 bp of the Humicola insolens endoglucanase V coding region. The 36 bp overlap between the promoter and the coding sequence allowed precise fusion of the 994 bp fragment comprising the *Trichoderma reesei* cbh1 promoter to the 918 bp fragment comprising the *Humicola insolens* endoglucanase V open reading frame.

The amplification reactions (50 µl) were composed of 1× ThermoPol Reaction Buffer, 0.3 mM dNTPs, 1 µl of 998 bp purified PCR fragment, 0.3 µM TrCBH1pro-F primer, 0.3 µM TrCBH1pro-R-overlap primer, and 2 U of Vent polymerase. The reactions were incubated in an Eppendorf Mastercycler 5333 programmed as follows: 5 cycles each for 30 seconds at 94° C., 30 seconds at 50° C., and 60 seconds at 72° C., followed by 25 cycles each for 30 seconds at 94° C., 30 seconds at 65° C., and 120 seconds at 72° C. (5 minute final extension). The reaction products were isolated on a 1.0% agarose gel using TAE buffer where a 1017 bp product band was excised from the gel and purified using a QIAquick Gel Extraction Kit according to the manufacturer's instructions.

The 1017 bp *Trichoderma reesei* cbh1 promoter PCR fragment and the 945 bp *Humicola insolens* endoglucanase V PCR fragments were used as template DNA for subsequent amplification using the following primers to precisely fuse the 994 bp *Trichoderma reesei* cbh1 promoter to the 918 bp *Humicola insolens* endoglucanase V coding region using overlapping PCR:

```
TrCBHIpro-F:                                 (SEQ ID NO: 24)
5'-AAACGTCGACCGAATGTAGGATTGTTATC-3'

HiEGV-R:                                     (SEQ ID NO: 25)
5'-CTGCAGAATTCTACAGGCACTGATGGTACCAG-3'
```

The amplification reactions (50 µl) were composed of 1× ThermoPol Reaction Buffer, 0.3 mM dNTPs, 0.3 µM TrCBH1pro-F primer, 0.3 µM HiEGV-R primer, and 2 U of Vent polymerase. The reactions were incubated in an Eppendorf Mastercycler 5333 programmed as follows: 5 cycles each for 30 seconds at 94° C., 30 seconds at 50° C., and 60 seconds at 72° C., followed by 25 cycles each for 30 seconds at 94° C., 30 seconds at 65° C., and 120 seconds at 72° C. (5 minute final extension). The reaction products were isolated on a 1.0% agarose gel using TAE buffer where a 1926 bp product band was excised from the gel and purified using a QIAquick Gel Extraction Kit according to the manufacturer's instructions.

The resulting 1926 bp fragment was cloned into pCR-Blunt-II-TOPO (Invitrogen, Carlsbad, Calif.) using a Zero-Blunt TOPO PCR Cloning Kit following the manufacturer's protocol. The resulting plasmid was digested with Not I and Sal I and the 1926 bp fragment was purified and ligated into pMJ04, which was also digested with the same two restriction enzymes, to generate pMJ05 (FIG. 6).

Example 5

Construction of pSMai130 Expression Vector

A 2586 bp DNA fragment spanning from the ATG start codon to the TAA stop codon of the *Aspergillus oryzae* beta-glucosidase coding sequence (SEQ ID NO: 26 for cDNA sequence and SEQ ID NO: 27 for the deduced amino acid sequence; *E. coli* DSM 14240) was amplified by PCR from pJaL660 (WO 2002/095014) as template with primers 993467 (sense) and 993456 (antisense) shown below. A Spe I site was engineered at the 5' end of the antisense primer to facilitate ligation. Primer sequences in italics are homologous to 24 bp of the *Trichoderma reesei* cbh1 promoter and underlined sequences are homologous to 22 bp of the *Aspergillus oryzae* beta-glucosidase coding region.

Primer 993467:                                    (SEQ ID NO: 28)
5'-
ATAGTCAACCGCGGACTGCGCATC<u>ATGAAGCTTGGTTGGATCGAGG</u>-3'

Primer 993456:                                    (SEQ ID NO: 29)
5'-ACTAGTTTACTGGGCCTTAGGCAGCG-3'

The amplification reactions (50 µl) were composed of Pfx Amplification Buffer (Invitrogen, Carlsbad, Calif.), 0.25 mM dNTPs, 10 ng of pJaL660 plasmid, 6.4 µM primer 993467, 3.2 µM primer 993456, 1 mM MgCl$_2$, and 2.5 U of Pfx polymerase (Invitrogen, Carlsbad, Calif.). The reactions were incubated in an Eppendorf Mastercycler 5333 programmed as follows: 30 cycles each for 60 seconds at 94° C., 60 seconds at 55° C., and 180 seconds at 72° C. (15 minute final extension). The reaction products were isolated on a 1.0% agarose gel using TAE buffer where a 2586 bp product band was excised from the gel and purified using a QIAquick Gel Extraction Kit according to the manufacturer's instructions.

A separate PCR was performed to amplify the *Trichoderma reesei* cbh1 promoter sequence extending from 1000 bp upstream of the ATG start codon of the gene, using primer 993453 (sense) and primer 993463 (antisense) shown below to generate a 1000 bp PCR fragment. Primer sequences in italics are homologous to 24 bp of the *Trichoderma reesei* cbh1 promoter and underlined primer sequences are homologous to 22 bp of the *Aspergillus oryzae* beta-glucosidase coding region. The 46 bp overlap between the promoter and the coding sequence allows precise fusion of the 1000 bp fragment comprising the *Trichoderma reesei* cbh1 promoter to the 2586 bp fragment comprising the *Aspergillus oryzae* beta-glucosidase open reading frame.

Primer 993453:                                    (SEQ ID NO: 30)
5'-GTCGACTCGAAGCCCGAATGTAGGAT-3'

Primer 993463:                                    (SEQ ID NO: 31)
5'-
<u>CCTCGATCCAACCAAGCTTCAT</u>GATGCGCAGTCCGCGGTTGACTA-3'

The amplification reactions (50 µl) were composed of Pfx Amplification Buffer, 0.25 mM dNTPs, 100 ng of *Trichoderma reesei* RutC30 genomic DNA, 6.4 µM primer 993453, 3.2 µM primer 993463, 1 mM MgCl$_2$, and 2.5 U of Pfx polymerase. The reactions were incubated in an Eppendorf Mastercycler 5333 programmed as follows: 30 cycles each for 60 seconds at 94° C., 60 seconds at 55° C., and 180 seconds at 72° C. (15 minute final extension). The reaction products were isolated on a 1.0% agarose gel using TAE buffer where a 1000 bp product band was excised from the gel and purified using a QIAquick Gel Extraction Kit according to the manufacturer's instructions.

The purified fragments were used as template DNA for subsequent amplification using primer 993453 (sense) and primer 993456 (antisense) shown above to precisely fuse the 1000 bp *Trichoderma reesei* cbh1 promoter to the 2586 bp *Aspergillus oryzae* beta-glucosidase fragment by overlapping PCR.

The amplification reactions (50 µl) were composed of Pfx Amplification Buffer, 0.25 mM dNTPs, 6.4 µM primer 99353, 3.2 µM primer 993456, 1 mM MgCl$_2$, and 2.5 U of Pfx polymerase. The reactions were incubated in an Eppendorf Mastercycler 5333 programmed as follows: 30 cycles each for 60 seconds at 94° C., 60 seconds at 60° C., and 240 seconds at 72° C. (15 minute final extension).

Figure 7:
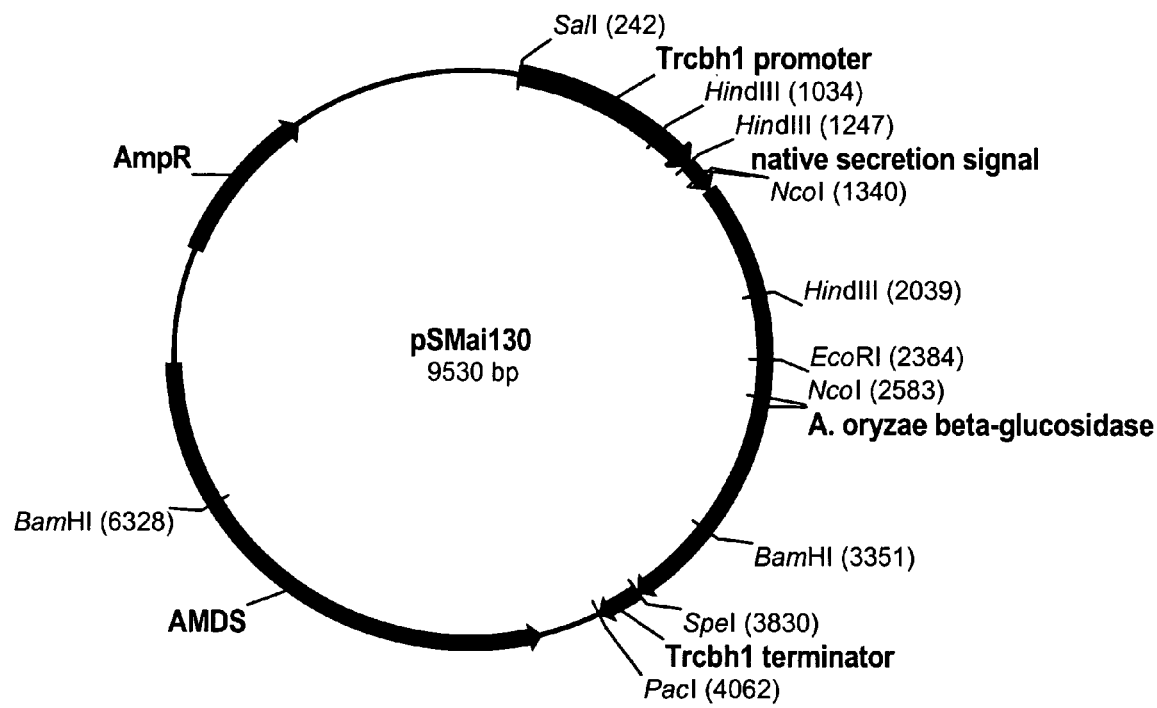
FIG. 7 shows a restriction map of pSMai130.

The resulting 3586 bp fragment was digested with Sal/I and SpeI and ligated into pMJ04, digested with the same two restriction enzymes, to generate pSMai130 (FIG. 7).

Example 6

Construction of pSMai135

The *Aspergillus oryzae* beta-glucosidase coding region (WO 2002/095014, *E. coli* DSM 14240, minus the signal sequence, see FIG. 8, DNA sequence (SEQ ID NO: 32) and deduced amino acid sequence (SEQ ID NO: 33)) from Lys-20 to the TAA stop codon was PCR amplified from pJaL660 (WO 2002/095014) as template with primer 993728 (sense) and primer 993727 (antisense) shown below. Sequences in italics are homologous to 20 bp of the *Humicola insolens* endoglucanase V signal sequence and sequences underlined are homologous to 22 bp of the *Aspergillus oryzae* beta-glucosidase coding region. A Spe I site was engineered into the 5' end of the antisense primer.

Primer 993728:                                    (SEQ ID NO: 34)
5'-*TGCCGGTGTTGGCCCTTGCC*<u>AAGGATGATCTCGCGTACTCCC</u>-3'

Primer 993727:                                    (SEQ ID NO: 35)
5'-GACTAGTCTTACTGGGCCTTAGGCAGCG-3'

The amplification reactions (50 µl) were composed of Pfx Amplification Buffer, 0.25 mM dNTPs, 10 ng/µl Jal660, 6.4 µM primer 993728, 3.2 µM primer 993727, 1 mM MgCl$_2$, and 2.5 U of Pfx polymerase. The reactions were incubated in an Eppendorf Mastercycler 5333 programmed as follows: 30 cycles each for 60 seconds at 94° C., 60 seconds at 55° C., and 180 seconds at 72° C. (15 minute final extension). The reaction products were isolated on a 1.0% agarose gel using TAE buffer where a 2523 bp product band was excised from the gel and purified using a QIAquick Gel Extraction Kit according to the manufacturer's instructions.

A separate PCR amplification was performed to amplify 1000 bp of the *Trichoderma reesei* Cel7A cellobiohydrolase 1 promoter and 63 bp of the putative *Humicola insolens* endoglucanase V signal sequence (ATG start codon to Ala-21, FIG. 9, SEQ ID NOs: 36 (DNA sequence) and 37 (deduced amino acid sequence; accession no. AAB03660 for DNA sequence), using primer 993724 (sense) and primer 993729 (antisense) shown below. Primer sequences in italics are homologous to 20 bp of the *Humicola insolens* endoglucanase V signal sequence and underlined primer sequences are homologous to 22 bp of the *Aspergillus oryzae* beta-glucosidase coding region. Plasmid pMJ05, which comprises the *Humicola insolens* endoglucanase V coding region under the control of the cbh1 promoter, was used as a template to generate a 1063 bp fragment comprising the *Trichoderma reesei* cbh1 promoter/*Humicola insolens* endoglucanase V signal sequence fragment. A 42 bp of overlap was shared between the *Trichoderma reesei* cbh1 promoter/*Humicola insolens* endoglucanase V signal sequence and the *Aspergillus oryzae* coding sequence to provide a perfect linkage between the promoter and the ATG start codon of the 2523 bp *Aspergillus oryzae* beta-glucosidase fragment.

Primer 993724:                                    (SEQ ID NO: 38)
5'-ACGCGTCGACCGAATGTAGGATTGTTATCC-3'

Primer 993729:                                    (SEQ ID NO: 39)
5'-<u>GGGAGTACGCGAGATCATCCTT</u>*GGCAAGGGCCAACACCGGCA*-3'

The amplification reactions (50 µl) were composed of Pfx Amplification Buffer, 0.25 mM dNTPs, 10 ng/µl pMJ05, 6.4

μM primer 993728, 3.2 μM primer 993727, 1 mM MgCl$_2$, and 2.5 U of Pfx polymerase. The reactions were incubated in an Eppendorf Mastercycler 5333 programmed as follows: 30 cycles each for 60 seconds at 94° C., 60 seconds at 60° C., and 240 seconds at 72° C. (15 minute final extension). The reaction products were isolated on a 1.0% agarose gel using TAE buffer where a 1063 bp product band was excised from the gel and purified using a QIAquick Gel Extraction Kit according to the manufacturer's instructions.

The purified overlapping fragments were used as a template for amplification using primer 993724 (sense) and primer 993727 (antisense) described above to precisely fuse the 1063 bp *Trichoderma reesei* cbh1 promoter/*Humicola insolens* endoglucanase V signal sequence fragment to the 2523 bp of *Aspergillus oryzae* beta-glucosidase fragment by overlapping PCR.

The amplification reactions (50 μl) were composed of Pfx Amplification Buffer, 0.25 mM dNTPs, 6.4 μM primer 993724, 3.2 μM primer 993727, 1 mM MgCl$_2$, and 2.5 U of Pfx polymerase. The reactions were incubated in an Eppendorf Mastercycler 5333 programmed as follows: 30 cycles each for 60 seconds at 94° C., 60 seconds at 60° C., and 240 seconds at 72° C. (15 minute final extension). The reaction products were isolated on a 1.0% agarose gel using TAE buffer where a 3591 bp product band was excised from the gel and purified using a QIAquick Gel Extraction Kit according to the manufacturer's instructions.

Figure 10:
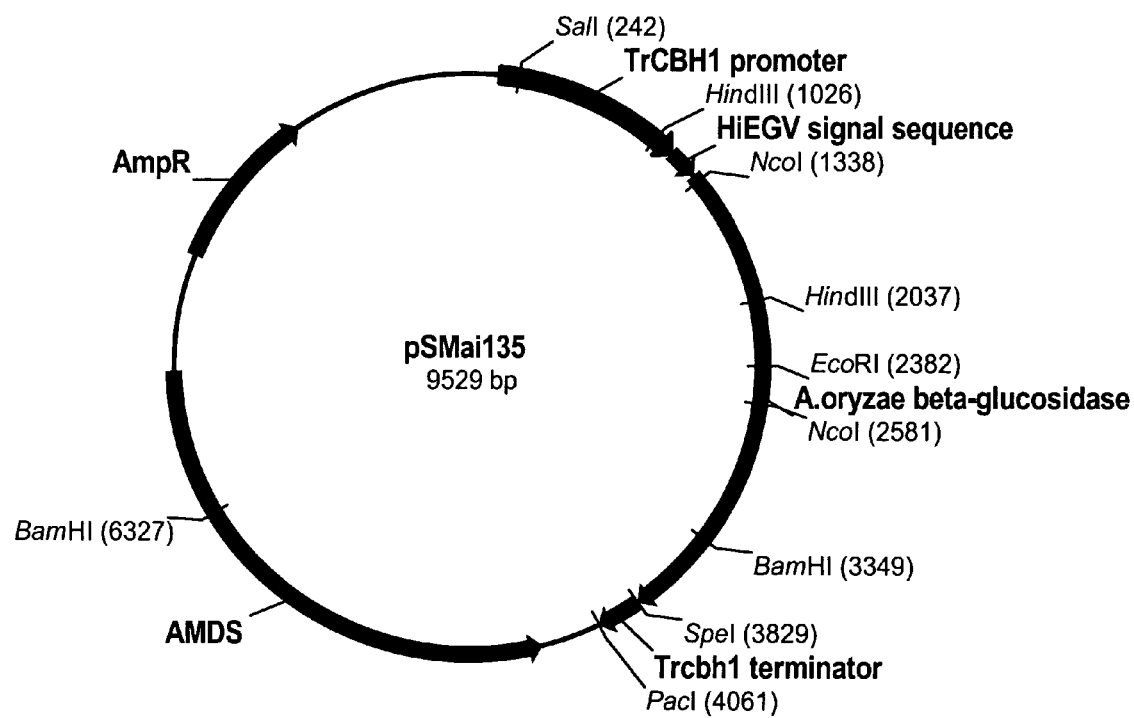
FIG. 10 shows a restriction map of pSMai135.

The resulting 3591 bp fragment was digested with Sal I and Spe I and ligated into pMJ04 digested with the same restriction enzymes to generate pSMai135 (FIG. 10).

Example 7

Expression of *Aspergillus oryzae* Beta-Glucosidase in *Trichoderma reesei*

Plasmid pSMai130, in which the *Aspergillus oryzae* beta-glucosidase is expressed from the cbh1 promoter and native secretion signal (FIG. 8), or pSMai135 encoding the mature *Aspergillus oryzae* beta-glucosidase enzyme linked to the *Humicola insolens* endoglucanase V secretion signal (FIG. 9), was introduced into *Trichoderma reesei* RutC30 by PEG-mediated transformation as described below. Both plasmids contain the *Aspergillus nidulans* amdS gene to enable transformants to grow on acetamide as the sole nitrogen source.

*Trichoderma reesei* RutC30 was cultivated at 27° C. and 90 rpm in 25 ml of YP medium (composed per liter of 10 g of yeast extract and 20 g of Bactopeptone) supplemented with 2% (w/v) glucose and 10 mM uridine for 17 hours. Mycelia were collected by filtration using Millipore's Vacuum Driven Disposable Filtration System (Millipore, Bedford, Mass.) and washed twice with deionized water and twice with 1.2 M sorbitol. Protoplasts were generated by suspending the washed mycelia in 20 ml of 1.2 M sorbitol containing 15 mg of Glucanex (Novozymes A/S, Bagsværd, Denmark) per ml and 0.36 units of chitinase (Sigma Chemical Co., St. Louis, Mo.) per ml and incubating for 15-25 minutes at 34° C. with gentle shaking at 90 rpm. Protoplasts were collected by centrifuging for 7 minutes at 400×g and washed twice with cold 1.2 M sorbitol. The protoplasts were counted using a haemacytometer and re-suspended in STC (1M sorbitol, 10 mM Tris-HCl, pH 6.5, 10 mM CaCl$_2$) to a final concentration of 1×10$^8$ protoplasts per ml. Excess protoplasts were stored in a Cryo 1° C. Freezing Container (Nalgene, Rochester, N.Y.) at −80° C.

Approximately 7 μg of Pme I digested expression plasmid (pSMai130 or pSMai135) was added to 100 μl of protoplast solution and mixed gently, followed by 260 μl of PEG buffer (60% PEG-4000, 10 mM Tris-HCl, pH 6.5, 10 mM CaCl$_2$), mixed, and incubated at room temperature for 30 minutes. STC (3 ml) was then added and mixed and then the transformation solution was plated onto COVE plates (composed per liter of 342.3 g of sucrose, 10 ml of 1 M acetamide solution, 10 ml of 1.5 M CsCl solution, 25 g of agar, and 20 ml of Cove salts solution; Cove salts solution was composed per liter of 26 g of KCl, 26 g of MgSO$_4$.7H$_2$O, 76 g of KH$_2$PO$_4$, and 50 ml of Cove trace metals solution; Cove trace metals solution was composed per liter of 0.04 g of Na$_2$B$_4$O$_7$.10H$_2$O, 0.4 g of CuSO$_4$.5H$_2$O, 1.2 g of FeSO$_4$.7H$_2$O, 0.7 g of MnSO$_4$.H$_2$O, 0.8 g of Na$_7$MoO$_7$.2H$_2$O, and 10 g of ZnSO$_4$.7H$_2$O). The plates were incubated at 28° C. for 5-7 days. Transformants were subcultured onto COVE2 plates (composed per liter of 30 g of sucrose, 10 ml of 1 M acetamide solution, 20 ml of Cove salts solution, and 25 g of agar) and grown at 28° C.

One hundred and ten amdS positive transformants were obtained with pSMai130 and 65 transformants with pSMai135. Twenty pSMai130 (native secretion signal) and 67 pSMai135 (heterologous secretion signal) transformants were subcultured onto fresh plates containing acetamide and allowed to sporulate for 7 days at 28° C.

The 20 pSMA130 and 67 pSMA135 *Trichoderma reesei* transformants were cultivated in 125 ml baffled shake flasks containing 25 ml of cellulase-inducing medium at pH 6.0 inoculated with spores of the transformants and incubated at 28° C. and 200 rpm for 7 days. *Trichoderma reesei* RutC30 was run as a control. Culture broth samples were removed at day 7. One ml of each culture broth was centrifuged at 15,700×g for 5 minutes in a micro-centrifuge and the supernatants transferred to new tubes. Samples were stored at 4° C. until enzyme assay. The supernatants were assayed for beta-glucosidase activity using p-nitrophenyl-beta-D-glucopyranoside as substrate, as described below.

Beta-glucosidase activity was determined at ambient temperature using 25 μl aliquots of culture supernatants, diluted 1:10 in 50 mM succinate pH 5.0, using 200 μl of 0.5 mg/ml p-nitrophenyl-beta-D-glucopyranoside as substrate in 50 mM succinate pH 5.0. After 15 minutes incubation the reaction was stopped by adding 100 μl of 1 M Tris-HCl pH 8.0 and the absorbance was read spectrophotometrically at 405 nm.

One unit of beta-glucosidase activity corresponded to production of 1 μmol of p-nitrophenyl per minute per liter at pH 5.0, ambient temperature. *Aspergillus niger* beta-glucosidase (Novozyme 188, Novozymes A/S, Bagsværd, Denmark) was used as an enzyme standard.

All 20 SMA130 transformants exhibited equivalent beta-glucosidase activity to that of the host strain, *Trichoderma reesei* RutC30. In contrast, a number of SMA135 transformants showed beta-glucosidase activities several fold more than that of *Trichoderma reesei* RutC30. Transformant SMA135-04 produced the highest beta-glucosidase activity, having seven times greater beta-glucosidase activity than produced by *Trichoderma reesei* RutC30 as a control.

SDS polyacrylamide electrophoresis was carried out using Criterion Tris-HCl (5% resolving) gels (BioRad, Hercules, Calif.) with The Criterion System (BioRad, Hercules, Calif.). Five μl of day 7 supernatants (see above) were suspended in 2× concentration of Laemmli Sample Buffer (BioRad, Hercules, Calif.) and boiled for 3 minutes in the presence of 5% beta-mercaptoethanol. The supernatant samples were loaded onto a polyacrylamide gel and subjected to electrophoresis with 1× Tris/Glycine/SDS as running buffer (BioRad, Hercules, Calif.). The resulting gel was stained with BioRad's Bio-Safe Coomassie Stain.

No beta-glucosidase protein was visible by SDS-PAGE for the *Trichoderma reesei* SMA130 transformant culture broth supernatants. In contrast, 26 of the 38 *Trichoderma reesei* SMA135 transformants produced a protein of approximately 110 kDa that was not visible in *Trichoderma reesei* RutC30 as control. Transformant *Trichoderma reesei* SMA135-04 produced the highest level of beta-glucosidase.

Example 8

Fermentation of *Trichoderma reesei* SMA135-04

Fermentations of *Trichoderma reesei* SMA135-04 were performed to determine the production level of beta-glucosidase activity. *Trichoderma reesei* RutC30 (host strain) was run as a control. Spores of *Trichoderma reesei* SMA135-04 were inoculated into 500 ml shake flasks, containing 100 ml of inoculum medium composed per liter of 20 g of glucose, 10 g of corn steep solids, 1.45 g of $(NH_4)_2SO_4$, 2.08 g of $KH_2PO_4$, 0.36 g of $CaCl_2.2H_2O$, 0.42 g of $MgSO_4.7H_2O$, and 0.2 ml of trace metals solution. The trace metals solution was composed per liter of 216 g of $FeCl_3.6H_2O$, 58 g of $ZnSO_4.7H_2O$, 27 g of $MnSO_4.H_2O$, 10 g of $CuSO_4.5H_2O$, 2.4 g of $H_3BO_3$, and 336 g of citric acid. The flasks were placed into an orbital shaker at 28° C. for approximately 48 hours at which time 50 ml of the culture was inoculated into 1.8 liters of fermentation medium composed per liter of 4 g of glucose, 10 g of corn steep solids, 30 g of cellulose, 2.64 g of $CaCl_2.2H_2O$, 3.8 g of $(NH_4)_2SO_4$, 2.8 g of $KH_2PO_4$, 1.63 g of of $MgSO_4.7H_2O$, 0.75 ml of trace metals solution (described above) in a 2 liter fermentation vessel. The fermentations were run at a pH of 5.0, 28° C., with minimum dissolved oxygen at a 25% at a 1.0 WM air flow and an agitation of 1100. Feed medium was delivered into the fermentation vessel at 18 hours with a feed rate of 3.6 g/hour for 33 hours and then 7.2 g/hour. The fermentations ran for 165 hours at which time the final fermentation broths were centrifuged and the supernatants stored at −20° C. until beta-glucosidase activity assay using the procedure described in Example 7.

Beta-glucosidase activity on the *Trichoderma reesei* SMA135-04 fermentation sample was determined to be approximately eight times greater than that produced by *Trichoderma reesei* RutC30.

Example 9

PCS Hydrolysis Using Fresh Fermentation Samples

PCS hydrolysis reactions were formulated using washed and milled corn stover that was pretreated with dilute sulfuric acid at elevated temperature and pressure. The following conditions were used for the pretreatment: acid concentration—1.4 wt %; temperature—165° C.; pressure 107 psi; time—8 minutes. Prior to enzymatic hydrolysis, the pretreated corn stover (PCS) was washed with a large volume of distilled-deionized (DDI) water on a glass filter. The dry weight of the water-washed PCS was found to be 24.54%. The water-insoluble solids in PCS contained 56.5% cellulose, 4.6% hemicellulose, and 28.4% lignin.

Prior to enzymatic hydrolysis, a suspension of milled PCS in DDI water was prepared as follows: DDI water-washed PCS was additionally washed with 95% ethanol on a 22 µm Millipore Filter (6P Express Membrane, Stericup), and then milled using a coffee-grinder to reduce the particle size. Dry weight of the milled PCS was found to be 41.8%. Milled PCS was washed with DDI water three times in order to remove the ethanol. After each washing, the suspension was centrifuged at 17,000×g for 10 minutes at 4° C. to separate the solids. Finally, DDI water was added to the milled water-washed solids to make 20 mg/ml suspension. The suspension was stored at 4° C. and used for 1 ml scale PCS hydrolysis at final concentration of 10 mg/ml.

*Trichoderma reesei* strains were grown in two-liter Applikon laboratory fermentors using a cellulase producing medium at 28° C., pH 4.5, and a growth time of approximately 120 hours. The cellulose producing medium was composed per liter of 5 g of glucose, 10 g of corn steep solids, 2.08 g of $CaCl_2$, 3.87 g of $(NH_4)_2SO_4$, 2.8 g of $KH_2PO_4$, 1.63 g of $MgSO_4.7H_2O$, 0.75 ml of trace metals solution, and 1.8 ml of pluronic with a feed of 20 g of cellulose per liter. The trace metals solution was composed per liter of 216 g of $FeCl_3.6H_2O$, 58 g of $ZnSO_4.7H_2O$, 27 g of $MnSO_4.H_2O$, 10 g of $CuSO_4.5H_2O$, 2.4 g of $H_3BO_3$, and 336 g of citric acid.

The procedure for preparation of whole fermentation broth (WB) and cell-free broth (CB) samples is outlined as follows. Briefly, two 50 ml aliquots of *Trichoderma reesei* culture were harvested aseptically in conical centrifuge tubes. One of these tubes was designated as the WB enzyme preparation without further treatment, and the other was centrifuged twice to remove cells and insoluble material to yield a CB enzyme sample. The first centrifugation was at low speed (1800×g for 10 minutes), and the second was at higher speed (12,000×g for 15 minutes).

PCS (10 mg/ml, 56.5% cellulose) was enzymatically hydrolyzed at 50° C. in 0.05 M sodium acetate buffer (pH 5.0) with intermittent mixing. Two types of enzyme preparations were used in these experiments: (a) Whole fermentation broth (WB) and (b) centrifuged fermentation broth (CB) as defined above. In one series of experiments CB that was centrifuged prior to storage (CB-A) for two weeks at 4° C. was compared with broth that was centrifuged after storage (CB-B). Four enzyme doses were tested: 2.5, 5.0, 10, and 20 mg/g of PCS. These doses were based on estimated protein concentrations of 60 g/L for standard lab-scale fermentations. The volume of each reaction was 1 ml in MicroWell96™ deep well plates (Fisher Scientific, Pittsburg, Pa.). At specified time points (1, 3, 6, 9, 12, 24, 48, 72, 96, and 120 hours) 20 µl aliquots were removed from the microplates using an 8-channel pipettor, and added to 180 µl of alkaline mixture (0.102 M $Na_2CO_3$+ 0.058 M $NaHCO_3$) in a 96-well flat-bottomed plate (Millipore, Billerica, Mass.) to terminate the reaction. The samples were centrifuged at 1800×g for 15 minutes to remove unreacted PCS residue. After appropriate dilutions, the filtrates were analyzed for reducing sugars (RS) using a microplate assay (see below).

The concentrations of reducing sugars (RS) in hydrolyzed PCS samples were measured using a p-hydroxybenzoic acid hydrazide (PHBAH) assay (Lever, 1972, *Anal. Biochem*, 47: 273-279), which was modified and adapted to a 96-well microplate format. Before the assay, the analyzed samples were diluted in water to bring the RS concentration into the 0.005-0.200 mg/ml range.

A 90 µl aliquot of each diluted reaction sample was placed in a 96-well conical-bottomed microplate (Corning Inc., Costar, clear polycarbonate). The reactions were started by addition of 60 µl of 1.25% PHBAH in 2% sodium hydroxide. Each assay plate was heated on a custom-made heating block for 10 minutes at 95° C., and allowed to cool at room temperature. After cooling, 60 µl of water was added to each well. A 100 µl aliquot was removed and transferred to a flat-bottomed 96-well plate (Corning Inc., Costar, medium binding polystyrene), and the absorbance at 405 nm ($A_{405}$) was measured using an UltraMark Microplate Reader (Bio-Rad, Hercules, Calif.). The $A_{405}$ values were translated into glucose equivalents using a standard curve. In order to increase the statistical precision of the assays, 32 replicates were done for each time point at each enzyme dose.

Standard curves were generated with eight glucose standards (0.000, 0.005, 0.010, 0.020, 0.030, 0.050, 0.075, and 0.100 mg/ml), which were treated similarly to the samples. Glucose standards were prepared by diluting a 10 mg/ml stock glucose solution with sodium carbonate/bicarbonate mixture (0.102 M $Na_2CO_3$+0.058 M $NaHCO_3$). Eight replicates of each standard were done to increase precision of the assays. The average correlation coefficient for the standard curves was greater than 0.99.

Glucose concentrations in each hydrolyzed sample were measured using an enzyme-linked assay method in which 50 µl of each diluted PCS hydrolysate were mixed with 100 µl of assay buffer (100 mM MOPS, pH 7, 0.01% Tween-20) and 150 µl of glucose assay reagent. The assay reagent contained the following ingredients (per liter): 0.5511 g of ATP, 0.9951 g of NAD, 0.5176 g of $MgSO_4.7H_2O$, 1000 Units/L hexokinase Type 300 (Sigma Chemical Co., St. Louis, Mo.), 1000 Units/L of glucose-6-phosphate dehydrogenase (Sigma Chemical Co., St. Louis, Mo.), 0.1 g of Tween-20, and 20.9 g of MOPS, pH 7.0. The reactions were incubated for 30 minutes at ambient temperature, and the absorbance was measured at 340 nm. Background absorbance was subtracted based on a zero glucose control, and the glucose concentrations were determined with respect to a standard curve generated with glucose concentrations ranging from 0.00 to 0.25 mg/ml.

The mean RS yield was calculated using data from all replicates at a particular enzyme dose and incubation time. Standard error of the mean (SEM) was calculated as the standard deviation divided by the square-root n, the number of replicates. The degree of cellulose conversion to reducing sugar (RS yield, percent) was calculated using the following equation:

$$RS\ Yield_{(\%)} = RS_{(mg/ml)} \times 100 \times 162/(5.65_{(mg/ml)} \times 180)$$

$$= RS_{(mg/ml)} \times 100/(5.65_{(mg/ml)} \times 1.111)$$

In this equation, RS is the concentration of reducing sugar in solution measured in glucose equivalents (mg/ml), 5.65 mg/ml is the initial concentration of cellulose, and the factor 1.111 reflects the weight gain in converting cellulose to glucose.

The probability that WB and CB data points represented statistically different populations was estimated using a Student t-test (with unequal variance) at each time point.

Figure 11:
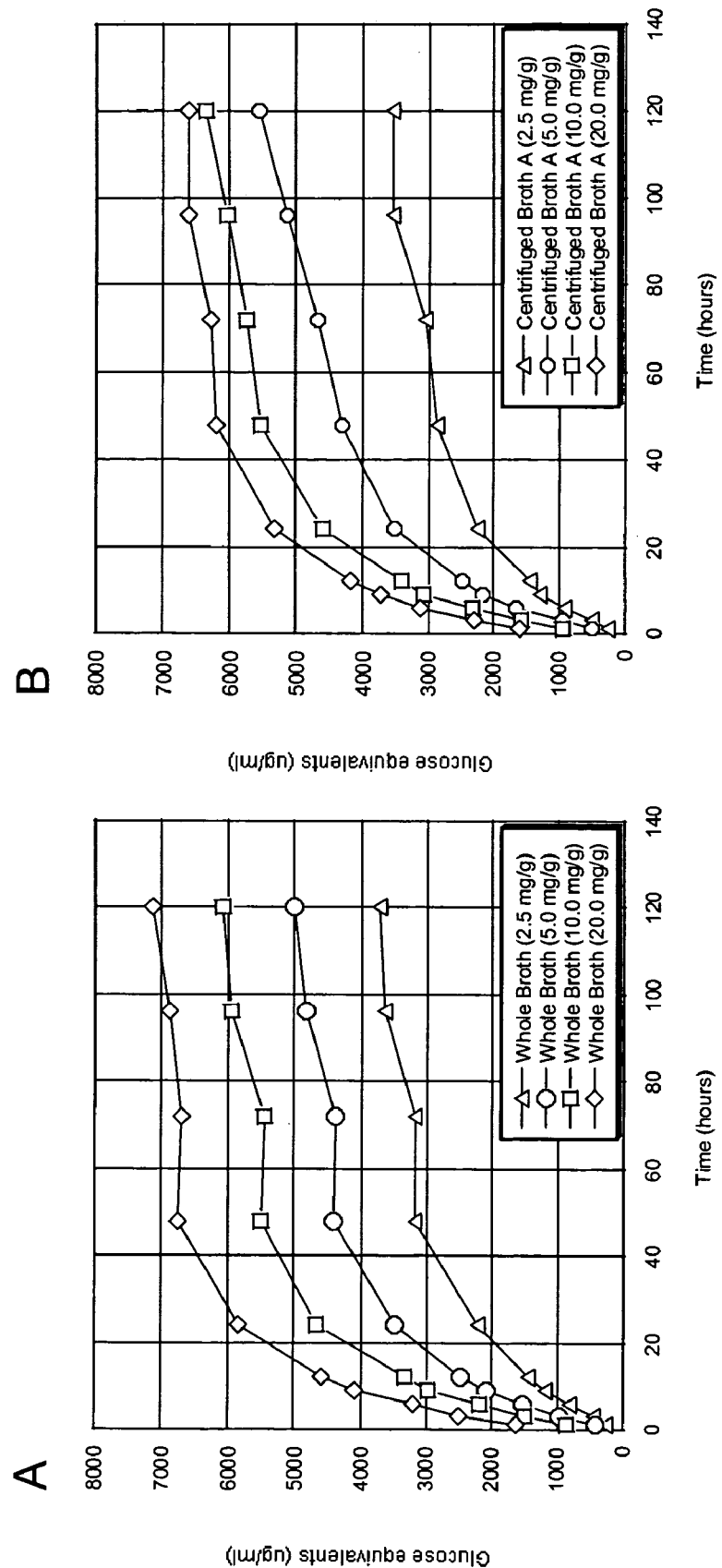
FIG. 11 shows the PCS hydrolysis profiles of whole fermentation broth (WB) (panel A) and cell-free broth (CB) (panel B) at enzyme doses ranging from 2.5 to 20 mg/g of PCS (noted in the lower right of each panel).
Figure 12:
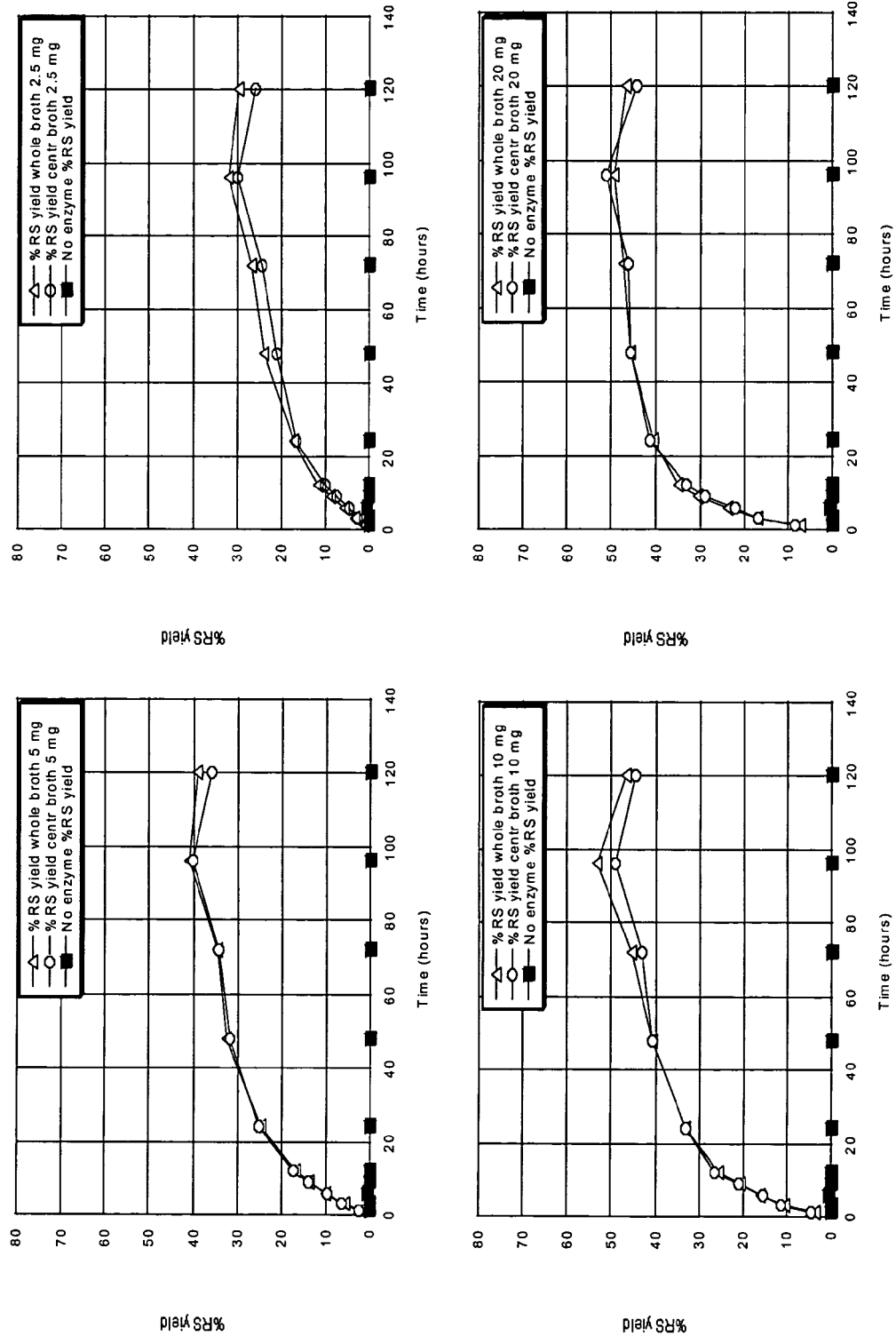
FIG. 12 shows the PCS hydrolysis curves for WB and CB samples derived from freshly harvested *Trichoderma reesei* RutC30 fermentation material. Each profile is plotted as % RS yield (% of theoretical maximum reducing sugar based on the glucan composition of 10 mg of PCS per ml) as a function of hydrolysis time (1-120 hours). Enzyme doses are noted in the upper right of each panel.

As shown in FIG. 11, the use of freshly harvested enzyme samples (WB and CB) produced PCS hydrolysis profiles that were nearly identical. These profiles could not be differentiated with a Student t-test suggesting that they were statistically indistinguishable. Using enzyme samples from *Trichoderma reesei* RutC30, the final RS yields ranged from approximately 30% conversion of the total glucan at the lowest enzyme dose to about 50% at the highest dose (FIG. 11). When the concentration of glucose was measured instead of reducing sugars, a similar picture emerged in that the glucose yields were comparable regardless of whether WB or CB was used (FIG. 12). However, it may be noteworthy that the glucose yields were approximately 20 to 25% lower than the reducing sugar concentrations suggesting that beta-glucosidase might be a limiting enzyme activity under these conditions.

Figure 13:
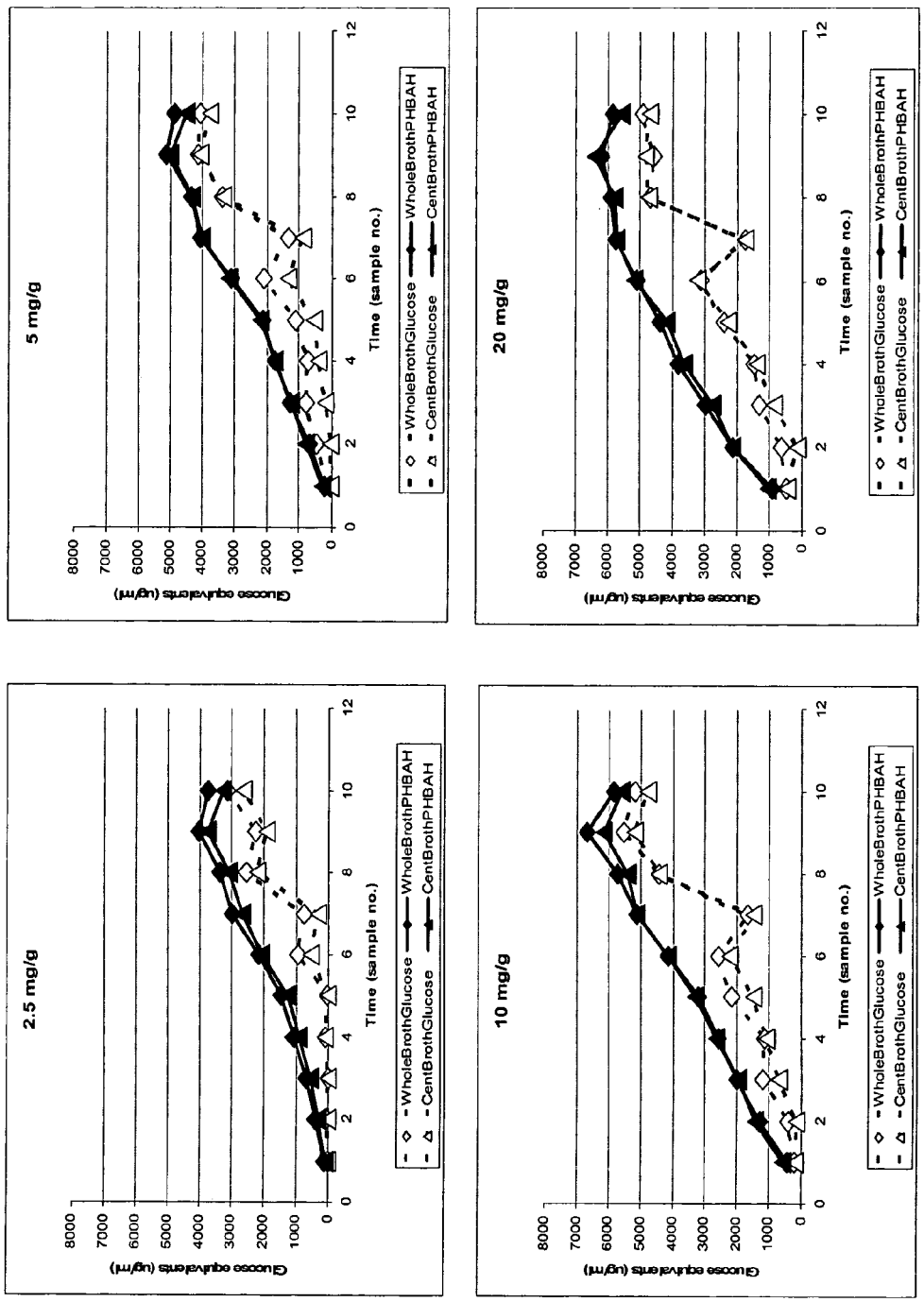
FIG. 13 shows a comparison of total reducing sugar (RS) and glucose liberated during PCS hydrolysis reactions using WB and CB samples from *Trichoderma reesei* RutC30. Enzyme doses are noted at the top of each panel. The sample numbers noted on the X-axis correspond to hydrolysis times spanning 1 to 120 hours.

In an effort to convert a higher percentage of RS to glucose, enzyme samples were deployed from the recombinant *Trichoderma reesei* strain SMA135-04 which expresses an *Aspergillus oryzae* beta-glucosidase gene. When these preparations with elevated β-glucosidase activity were employed, several differences were observed based on a comparison to the results from *Trichoderma reesei* RutC30 enzyme samples. First, within the limits of systematic and experimental errors the PCS hydrolysis curves for WB and CB were very similar (FIG. 13). Second, at the lowest enzyme dose (2.5 mg/g of PCS) the final RS yields obtained from *Trichoderma reesei* SAM135-04 enzyme samples were approximately 40% of the total glucan hydrolyzed compared to 30% for *Trichoderma reesei* RutC30 enzyme. Third, the final RS titers at higher enzyme doses were essentially unchanged compared to those obtained when using WB and CB preparations derived from *Trichoderma reesei* RutC30 (FIG. 13). The reasons for this phenomenon are unclear, but it may reflect either thermal inactivation of endoglucanases and cellobiohydrolases during prolonged incubation at 50° C. or end product inhibition of the *Aspergillus oryzae* β-glucosidase. On the basis of these comparisons the data consistently suggested that there is little difference between WB and CB hydrolysis profiles. Both the reaction kinetics and final RS titers appeared to be similar.

Figure 14:
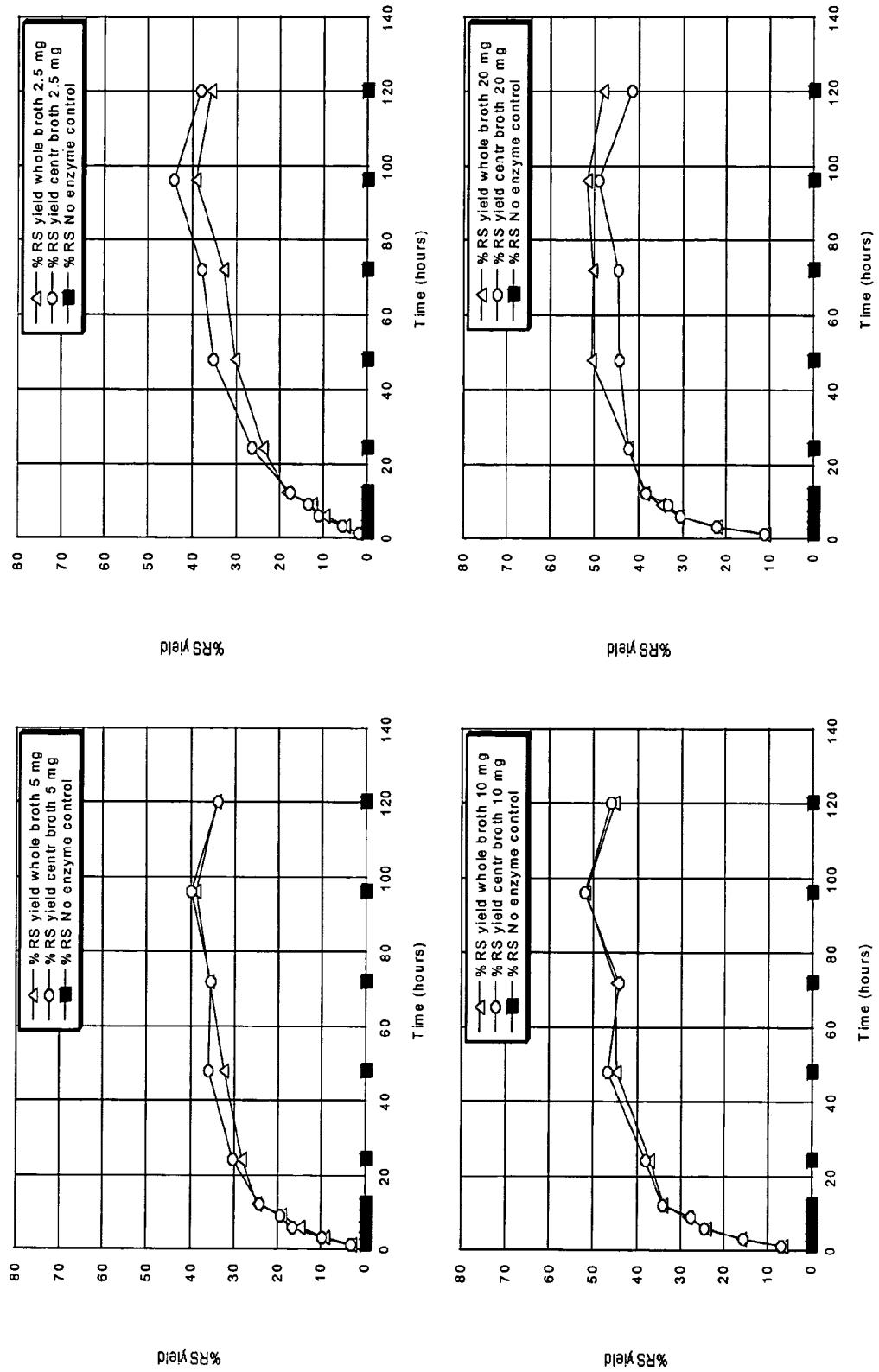
FIG. 14 shows the PCS hydrolysis curves for WB and CB samples derived from freshly harvested *Trichoderma reesei*

When the RS and glucose yields generated from WB and CB samples of *Trichoderma reesei* SMA135-04 were compared to those obtained from *Trichoderma reesei* RutC30 preparations, we observed that a higher percentage of RS was converted to glucose by SMA135-04 enzyme samples (FIG. 14). This was not unexpected since Trichoderma reesei SMA135-04 produces higher levels of β-glucosidase than *Trichoderma reesei* RutC30. Interestingly, at early time points (up to 24 hours), the RS and glucose levels generated from the *Trichoderma reesei* SMA135-04 enzyme preparations differed by only a few percent (FIG. 14). However, during later stages of the reactions, the RS and glucose curves diverge perceptibly, suggesting that the beta-glucosidase activity may be declining in the later stages of PCS hydrolysis under these conditions. This was particularly apparent at later times for the highest enzyme dose (20 mg/g of PCS). In addition, it appeared that WB was outperforming CB in generation of both RS and glucose over this same time period. A Student t-test predicted that the variance in RS values was statistically significant (P<0.05) over the time frame of 48-120 hours. Whether the observed difference in performance can be attributed to specific enzyme(s) or non-specific effects attributed to the presence of the mycelia is unknown. However, it should be noted that the phenomenon was not observed when using WB and CB enzyme samples from *Trichoderma reesei* RutC30 (FIG. 15), suggesting instability of the heterologous *Aspergillus oryzae* beta-glucosidase expressed by *Trichoderma reesei* SMA135-04 during prolonged incubation.

Example 10

PCS Hydrolysis Using Fermentation Broth Stored for Two Weeks at 4° C.

A biomass-to-ethanol process scheme involving on-site enzyme manufacturing should incorporate enough flexibility to allow for finite storage of enzyme preparations without significant loss of potency. Therefore, whether prolonged cold storage of enzyme samples affected their performance in microtiter-scale PCS hydrolysis reactions was investigated. In addition to WB, two types of CB preparations were tested. CB-A samples were centrifuged at time of harvest and stored at 4° C. as cell-free supernatant; CB-B preparations were stored at 4° C. as whole broth, then centrifuged to remove cells at the time of the assay.

The PCS hydrolysis reactins were performed as described in Example 9.

FIGS. 16 and 17 shows that the hydrolysis curves for WB, CB-A, and CB-B were principally similar. Statistical analyses using Student t-tests supported that these data points were not appreciably different. Furthermore, the final RS yields obtained using enzyme samples that were stored for two weeks were essentially the same as those obtained from the use of fresh fermentation broth. As was observed with fresh broth material, the lowest dose of *Trichoderma reesei* SMA135-04 enzyme (2.5 mg/g of PCS) gave slightly higher RS yields than the same dose of Tv10 material, ostensibly because of higher beta-glucosidase levels produced by *Trichoderma reesei* SMA135-04.

These results can be summarized as follows:

1. WB appears to perform as well as CB for hydrolysis of PCS under the assay conditions described in this series of experiments.
2. It is possible to store WB and CB enzyme samples from *Trichoderma reesei* fermentations for at least two weeks at 4° C. without significant loss of potency in our hydrolysis assay.
3. CB may be processed from WB that has been stored for two weeks at 4° C. without appreciable loss of activity in our hydrolysis assay.

Collectively, the results suggested that it is possible to achieve similar PCS hydrolysis results using WB instead of fractionated or formulated culture filtrates. It should be highlighted that the hydrolysis experiments were dosed on an equal volume basis, and they were not normalized on the basis of enzyme activity or protein concentration. Consequently, it was surprising to have observed equivalent performance of WB and CB dosed in this manner, because the fungal cell mass accounted for approximately 20-30% of the volume in WB. This implied that the effective dose of extracellular enzyme in the WB preparations was about 20-30% lower than that of CB.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. A method for degrading or converting plant cell wall polysaccharides into glucose, comprising: treating the plant cell wall polysaccharides with an effective amount of a spent whole fermentation broth of a recombinant *Trichoderma reesei* cell comprising a heterologous polynucleotide encoding the beta-glucosidase of SEQ ID NO: 27, wherein the *Trichoderma reesei* cell comprises one or more native genes encoding enzymes that degrade or convert plant cell wall polysaccharides and the spent whole fermentation broth degrades or converts the plant cell wall polysaccharides into glucose.

2. The method of claim 1, wherein the *Trichoderma reesei* cell further comprises one or more heterologous polynucleotides encoding a cellulase, an endoglucanase, a cellobiohydrolase, or a combination thereof.

3. The method of claim 1, wherein the method is a pretreatment process.

4. The method of claim 1, wherein the method is a step in a simultaneous saccharification and fermentation process (SSF).

5. The method of claim 1, wherein the method is a step in a hybrid hydrolysis and fermentation process (HHF).

6. The method of claim 1, further comprising recovering the glucose obtained from the degraded or converted plant cell wall polysaccharides.

7. The method of claim 1, wherein the plant cell wall polysaccharides are also degraded or converted to xylose, mannose, galactose, arabinose, or a combination thereof.

8. The method of claim 1, wherein the spent whole fermentation broth is supplemented with one or more enzyme activities not expressed by the recombinant microorganism to improve the degradation or the conversion of the plant cell wall polysaccharides.

9. The method of claim 1, wherein the *Trichoderma reesei* cell is *Trichoderma reesei* RutC30.

* * * * *

```
                          SEQUENCE LISTING

<160> NUMBER OF SEQ ID NOS: 39

<210> SEQ ID NO 1
<211> LENGTH: 22
<212> TYPE: DNA
<213> ORGANISM: Aspergillus nidulens

<400> SEQUENCE: 1
gtgccccatg atacgcctcc gg                                            22

<210> SEQ ID NO 2
<211> LENGTH: 26
<212> TYPE: DNA
<213> ORGANISM: Aspergillus nidulens

<400> SEQUENCE: 2
gagtcgtatt tccaaggctc ctgacc                                        26

<210> SEQ ID NO 3
<211> LENGTH: 24
<212> TYPE: DNA
<213> ORGANISM: Aspergillus nidulens

<400> SEQUENCE: 3
ggaggccatg aagtggacca acgg                                          24

<210> SEQ ID NO 4
<211> LENGTH: 45
<212> TYPE: DNA
<213> ORGANISM: Aspergillus niger

<400> SEQUENCE: 4
caccgtgaaa gccatgctct ttccttcgtg tagaagacca gacag                   45
```

```
<210> SEQ ID NO 5
<211> LENGTH: 45
<212> TYPE: DNA
<213> ORGANISM: Aspergillus niger

<400> SEQUENCE: 5
ctggtcttct acacgaagga aagagcatgg ctttcacggt gtctg              45

<210> SEQ ID NO 6
<211> LENGTH: 44
<212> TYPE: DNA
<213> ORGANISM: Aspergillus niger

<400> SEQUENCE: 6
ctatatacac aactggattt accatgggcc cgcggccgca gatc               44

<210> SEQ ID NO 7
<211> LENGTH: 44
<212> TYPE: DNA
<213> ORGANISM: Aspergillus niger

<400> SEQUENCE: 7
gatctgcggc cgcgggccca tggtaaatcc agttgtgtat atag               44

<210> SEQ ID NO 8
<211> LENGTH: 29
<212> TYPE: DNA
<213> ORGANISM: Trichoderma reesei

<400> SEQUENCE: 8
aacgttaatt aaggaatcgt tttgtgttt                                29

<210> SEQ ID NO 9
<211> LENGTH: 29
<212> TYPE: DNA
<213> ORGANISM: Trichoderma reesei

<400> SEQUENCE: 9
agtactagta gctccgtggc gaaagcctg                                29

<210> SEQ ID NO 10
<211> LENGTH: 31
<212> TYPE: DNA
<213> ORGANISM: Humicola insolens

<400> SEQUENCE: 10
ttgaattgaa aatagattga tttaaaactt c                             31

<210> SEQ ID NO 11
<211> LENGTH: 25
<212> TYPE: DNA
<213> ORGANISM: Humicola insolens

<400> SEQUENCE: 11
ttgcatgcgt aatcatggtc atagc                                    25

<210> SEQ ID NO 12
<211> LENGTH: 26
<212> TYPE: DNA
<213> ORGANISM: Saccharomyces cerevisiae

<400> SEQUENCE: 12
ttgaattcat gggtaataac tgatat                                   26
```

```
<210> SEQ ID NO 13
<211> LENGTH: 32
<212> TYPE: DNA
<213> ORGANISM: Saccharomyces cerevisiae

<400> SEQUENCE: 13
aaatcaatct attttcaatt caattcatca tt                              32

<210> SEQ ID NO 14
<211> LENGTH: 45
<212> TYPE: DNA
<213> ORGANISM: Aspergillus nidulens

<400> SEQUENCE: 14
ggatgctgtt gactccggaa atttaacggt ttggtcttgc atccc                45

<210> SEQ ID NO 15
<211> LENGTH: 44
<212> TYPE: DNA
<213> ORGANISM: Aspergillus nidulens

<400> SEQUENCE: 15
ggtattgtcc tgcagacggc aatttaacgg cttctgcgaa tcgc                 44

<210> SEQ ID NO 16
<211> LENGTH: 29
<212> TYPE: DNA
<213> ORGANISM: Humicola insolens

<400> SEQUENCE: 16
aagcttaagc atgcgttcct ccccctcc                                   29

<210> SEQ ID NO 17
<211> LENGTH: 32
<212> TYPE: DNA
<213> ORGANISM: Humicola insolens

<400> SEQUENCE: 17
ctgcagaatt ctacaggcac tgatggtacc ag                              32

<210> SEQ ID NO 18
<211> LENGTH: 32
<212> TYPE: DNA
<213> ORGANISM: Humicola insolens

<400> SEQUENCE: 18
ctgcagaatt ctacaggcac tgatggtacc ag                              32

<210> SEQ ID NO 19
<211> LENGTH: 36
<212> TYPE: DNA
<213> ORGANISM: Humicola insolens

<400> SEQUENCE: 19
accgcggact gcgcatcatg cgttcctccc ccctcc                          36

<210> SEQ ID NO 20
<211> LENGTH: 29
<212> TYPE: DNA
<213> ORGANISM: Trichoderma reesei

<400> SEQUENCE: 20
aaacgtcgac cgaatgtagg attgttatc                                  29
```

```
<210> SEQ ID NO 21
<211> LENGTH: 17
<212> TYPE: DNA
<213> ORGANISM: Trichoderma reesei

<400> SEQUENCE: 21
gatgcgcagt ccgcggt                                                    17

<210> SEQ ID NO 22
<211> LENGTH: 29
<212> TYPE: DNA
<213> ORGANISM: Trichoderma reesei

<400> SEQUENCE: 22
aaacgtcgac cgaatgtagg attgttatc                                       29

<210> SEQ ID NO 23
<211> LENGTH: 36
<212> TYPE: DNA
<213> ORGANISM: Trichoderma reesei

<400> SEQUENCE: 23
ggagggggga ggaacgcatg atgcgcagtc cgcggt                               36

<210> SEQ ID NO 24
<211> LENGTH: 29
<212> TYPE: DNA
<213> ORGANISM: Trichoderma reesei

<400> SEQUENCE: 24
aaacgtcgac cgaatgtagg attgttatc                                       29

<210> SEQ ID NO 25
<211> LENGTH: 32
<212> TYPE: DNA
<213> ORGANISM: Humicola insolens

<400> SEQUENCE: 25
ctgcagaatt ctacaggcac tgatggtacc ag                                   32

<210> SEQ ID NO 26
<211> LENGTH: 2771
<212> TYPE: DNA
<213> ORGANISM: Aspergillus oryzae
<220> FEATURE:
<221> NAME/KEY: CDS
<222> LOCATION: (30)..(2612)
<220> FEATURE:
<221> NAME/KEY: mat_peptide
<222> LOCATION: (87)..()

<400> SEQUENCE: 26
ctgttctgct ggttacctgc cacgttatc atg aag ctt ggt tgg atc gag gtg       53
                                 Met Lys Leu Gly Trp Ile Glu Val
                                                 -15 gcc gca ttg gcg gct gcc tca gta gtc agt gcc aag gat gat ctc gcg      101
Ala Ala Leu Ala Ala Ala Ser Val Val Ser Ala Lys Asp Asp Leu Ala
    -10              -5              -1 1                   5 tac tcc cct cct ttc tac cct tcc cca tgg gca gat ggt cag ggt gaa      149
Tyr Ser Pro Pro Phe Tyr Pro Ser Pro Trp Ala Asp Gly Gln Gly Glu
            10              15                  20 tgg gcg gaa gta tac aaa cgc gct gta gac ata gtt tcc cag atg acg      197
Trp Ala Glu Val Tyr Lys Arg Ala Val Asp Ile Val Ser Gln Met Thr
        25                  30                  35
```

```
ttg aca gag aaa gtc aac tta acg act gga aca gga tgg caa cta gag       245
Leu Thr Glu Lys Val Asn Leu Thr Thr Gly Thr Gly Trp Gln Leu Glu
        40                  45                  50 agg tgt gtt gga caa act ggc agt gtt ccc aga ctc aac atc ccc agc       293
Arg Cys Val Gly Gln Thr Gly Ser Val Pro Arg Leu Asn Ile Pro Ser
 55                  60                  65 ttg tgt ttg cag gat agt cct ctt ggt att cgt ttc tcg gac tac aat       341
Leu Cys Leu Gln Asp Ser Pro Leu Gly Ile Arg Phe Ser Asp Tyr Asn
 70                  75                  80                  85 tca gct ttc cct gcg ggt gtt aat gtc gct gcc acc tgg gac aag acg       389
Ser Ala Phe Pro Ala Gly Val Asn Val Ala Ala Thr Trp Asp Lys Thr
                 90                  95                 100 ctc gcc tac ctt cgt ggt cag gca atg ggt gag gag ttc agt gat aag       437
Leu Ala Tyr Leu Arg Gly Gln Ala Met Gly Glu Glu Phe Ser Asp Lys
                105                 110                 115 ggt att gac gtt cag ctg ggt cct gct gct ggc cct ctc ggt gct cat       485
Gly Ile Asp Val Gln Leu Gly Pro Ala Ala Gly Pro Leu Gly Ala His
        120                 125                 130 ccg gat ggc ggt aga aac tgg gaa ggt ttc tca cca gat cca gcc ctc       533
Pro Asp Gly Gly Arg Asn Trp Glu Gly Phe Ser Pro Asp Pro Ala Leu
        135                 140                 145 acc ggt gta ctt ttt gcg gag acg att aag ggt att caa gat gct ggt       581
Thr Gly Val Leu Phe Ala Glu Thr Ile Lys Gly Ile Gln Asp Ala Gly
150                 155                 160                 165 gtc att gcg aca gct aag cat tat atc atg aac gaa caa gag cat ttc       629
Val Ile Ala Thr Ala Lys His Tyr Ile Met Asn Glu Gln Glu His Phe
                170                 175                 180 cgc caa caa ccc gag gct gcg ggt tac gga ttc aac gta agc gac agt       677
Arg Gln Gln Pro Glu Ala Ala Gly Tyr Gly Phe Asn Val Ser Asp Ser
                185                 190                 195 ttg agt tcc aac gtt gat gac aag act atg cat gaa ttg tac ctc tgg       725
Leu Ser Ser Asn Val Asp Asp Lys Thr Met His Glu Leu Tyr Leu Trp
        200                 205                 210 ccc ttc gcg gat gca gta cgc gct gga gtc ggt gct gtc atg tgc tct       773
Pro Phe Ala Asp Ala Val Arg Ala Gly Val Gly Ala Val Met Cys Ser
        215                 220                 225 tac aac caa atc aac aac agc tac ggt tgc gag aat agc gaa act ctg       821
Tyr Asn Gln Ile Asn Asn Ser Tyr Gly Cys Glu Asn Ser Glu Thr Leu
230                 235                 240                 245 aac aag ctt ttg aag gcg gag ctt ggt ttc caa ggc ttc gtc atg agt       869
Asn Lys Leu Leu Lys Ala Glu Leu Gly Phe Gln Gly Phe Val Met Ser
                250                 255                 260 gat tgg acc gct cat cac agc ggc gta ggc gct gct tta gca ggt ctg       917
Asp Trp Thr Ala His His Ser Gly Val Gly Ala Ala Leu Ala Gly Leu
        265                 270                 275 gat atg tcg atg ccc ggt gat gtt acc ttc gat agt ggt acg tct ttc       965
Asp Met Ser Met Pro Gly Asp Val Thr Phe Asp Ser Gly Thr Ser Phe
        280                 285                 290 tgg ggt gca aac ttg acg gtc ggt gtc ctt aac ggt aca atc ccc caa      1013
Trp Gly Ala Asn Leu Thr Val Gly Val Leu Asn Gly Thr Ile Pro Gln
295                 300                 305 tgg cgt gtt gat gac atg gct gtc cgt atc atg gcc gct tat tac aag      1061
Trp Arg Val Asp Asp Met Ala Val Arg Ile Met Ala Ala Tyr Tyr Lys
310                 315                 320                 325 gtt ggc cgc gac acc aaa tac acc cct ccc aac ttc agc tcg tgg acc      1109
Val Gly Arg Asp Thr Lys Tyr Thr Pro Pro Asn Phe Ser Ser Trp Thr
                330                 335                 340
```

```
                                              -continued
agg gac gaa tat ggt ttc gcg cat aac cat gtt tcg gaa ggt gct tac       1157
Arg Asp Glu Tyr Gly Phe Ala His Asn His Val Ser Glu Gly Ala Tyr
            345                 350                 355 gag agg gtc aac gaa ttc gtg gac gtg caa cgc gat cat gcc gac cta       1205
Glu Arg Val Asn Glu Phe Val Asp Val Gln Arg Asp His Ala Asp Leu
        360                 365                 370 atc cgt cgc atc ggc gcg cag agc act gtt ctg ctg aag aac aag ggt       1253
Ile Arg Arg Ile Gly Ala Gln Ser Thr Val Leu Leu Lys Asn Lys Gly
    375                 380                 385 gcc ttg ccc ttg agc cgc aag gaa aag ctg gtc gcc ctt ctg gga gag       1301
Ala Leu Pro Leu Ser Arg Lys Glu Lys Leu Val Ala Leu Leu Gly Glu
390                 395                 400                 405 gat gcg ggt tcc aac tcg tgg ggc gct aac ggc tgt gat gac cgt ggt       1349
Asp Ala Gly Ser Asn Ser Trp Gly Ala Asn Gly Cys Asp Asp Arg Gly
                410                 415                 420 tgc gat aac ggt acc ctt gcc atg gcc tgg ggt agc ggt act gcg aat       1397
Cys Asp Asn Gly Thr Leu Ala Met Ala Trp Gly Ser Gly Thr Ala Asn
            425                 430                 435 ttc cca tac ctc gtg aca cca gag cag gcg att cag aac gaa gtt ctt       1445
Phe Pro Tyr Leu Val Thr Pro Glu Gln Ala Ile Gln Asn Glu Val Leu
        440                 445                 450 cag ggc cgt ggt aat gtc ttc gcc gtg acc gac agt tgg gcg ctc gac       1493
Gln Gly Arg Gly Asn Val Phe Ala Val Thr Asp Ser Trp Ala Leu Asp
    455                 460                 465 aag atc gct gcg gct gcc cgc cag gcc agc gta tct ctc gtg ttc gtc       1541
Lys Ile Ala Ala Ala Arg Gln Ala Ser Val Ser Leu Val Phe Val
470                 475                 480                 485 aac tcc gac tca gga gaa agc tat ctt agt gtg gat gga aat gag ggc       1589
Asn Ser Asp Ser Gly Glu Ser Tyr Leu Ser Val Asp Gly Asn Glu Gly
                490                 495                 500 gat cgt aac aac atc act ctg tgg aag aac ggc gac aat gtg gtc aag       1637
Asp Arg Asn Asn Ile Thr Leu Trp Lys Asn Gly Asp Asn Val Val Lys
            505                 510                 515 acc gca gcg aat aac tgt aac aac acc gtg gtc atc atc cac tcc gtc       1685
Thr Ala Ala Asn Asn Cys Asn Asn Thr Val Val Ile Ile His Ser Val
        520                 525                 530 gga cca gtt ttg atc gat gaa tgg tat gac cac ccc aat gtc act ggt       1733
Gly Pro Val Leu Ile Asp Glu Trp Tyr Asp His Pro Asn Val Thr Gly
    535                 540                 545 att ctc tgg gct ggt ctg cca ggc cag gag tct ggt aac tcc atc gcc       1781
Ile Leu Trp Ala Gly Leu Pro Gly Gln Glu Ser Gly Asn Ser Ile Ala
550                 555                 560                 565 gat gtg ctg tac ggt cgt gtc aac cct ggc gcc aag tct cct ttc act       1829
Asp Val Leu Tyr Gly Arg Val Asn Pro Gly Ala Lys Ser Pro Phe Thr
                570                 575                 580 tgg ggc aag acc cgg gag tcg tat ggt tct ccc ttg gtc aag gat gcc       1877
Trp Gly Lys Thr Arg Glu Ser Tyr Gly Ser Pro Leu Val Lys Asp Ala
            585                 590                 595 aac aat ggc aac gga gcg ccc cag tct gat ttc acc cag ggt gtt ttc       1925
Asn Asn Gly Asn Gly Ala Pro Gln Ser Asp Phe Thr Gln Gly Val Phe
        600                 605                 610 atc gat tac cgc cat ttc gat aag ttc aat gag acc cct atc tac gag       1973
Ile Asp Tyr Arg His Phe Asp Lys Phe Asn Glu Thr Pro Ile Tyr Glu
    615                 620                 625 ttt ggc tac ggc ttg agc tac acc acc ttc gag ctc tcc gac ctc cat       2021
Phe Gly Tyr Gly Leu Ser Tyr Thr Thr Phe Glu Leu Ser Asp Leu His
630                 635                 640                 645 gtt cag ccc ctg aac gcg tcc cga tac act ccc acc agt ggc atg act       2069
Val Gln Pro Leu Asn Ala Ser Arg Tyr Thr Pro Thr Ser Gly Met Thr
                650                 655                 660
```

```
gaa gct gca aag aac ttt ggt gaa att ggc gat gcg tcg gag tac gtg      2117
Glu Ala Ala Lys Asn Phe Gly Glu Ile Gly Asp Ala Ser Glu Tyr Val
            665                 670                 675 tat ccg gag ggg ctg gaa agg atc cat gag ttt atc tat ccc tgg atc      2165
Tyr Pro Glu Gly Leu Glu Arg Ile His Glu Phe Ile Tyr Pro Trp Ile
        680                 685                 690 aac tct acc gac ctg aag gca tcg tct gac gat tct aac tac ggc tgg      2213
Asn Ser Thr Asp Leu Lys Ala Ser Ser Asp Asp Ser Asn Tyr Gly Trp
    695                 700                 705 gaa gac tcc aag tat att ccc gaa ggc gcc acg gat ggg tct gcc cag      2261
Glu Asp Ser Lys Tyr Ile Pro Glu Gly Ala Thr Asp Gly Ser Ala Gln
710                 715                 720                 725 ccc cgt ttg ccc gct agt ggt ggt gcc gga gga aac ccc ggt ctg tac      2309
Pro Arg Leu Pro Ala Ser Gly Gly Ala Gly Gly Asn Pro Gly Leu Tyr
                730                 735                 740 gag gat ctt ttc cgc gtc tct gtg aag gtc aag aac acg ggc aat gtc      2357
Glu Asp Leu Phe Arg Val Ser Val Lys Val Lys Asn Thr Gly Asn Val
            745                 750                 755 gcc ggt gat gaa gtt cct cag ctg tac gtt tcc cta ggc ggc ccg aat      2405
Ala Gly Asp Glu Val Pro Gln Leu Tyr Val Ser Leu Gly Gly Pro Asn
        760                 765                 770 gag ccc aag gtg gta ctg cgc aag ttt gag cgt att cac ttg gcc cct      2453
Glu Pro Lys Val Val Leu Arg Lys Phe Glu Arg Ile His Leu Ala Pro
    775                 780                 785 tcg cag gag gcc gtg tgg aca acg acc ctt acc cgt cgt gac ctt gca      2501
Ser Gln Glu Ala Val Trp Thr Thr Thr Leu Thr Arg Arg Asp Leu Ala
790                 795                 800                 805 aac tgg gac gtt tcg gct cag gac tgg acc gtc act cct tac ccc aag      2549
Asn Trp Asp Val Ser Ala Gln Asp Trp Thr Val Thr Pro Tyr Pro Lys
                810                 815                 820 acg atc tac gtt gga aac tcc tca cgg aaa ctg ccg ctc cag gcc tcg      2597
Thr Ile Tyr Val Gly Asn Ser Ser Arg Lys Leu Pro Leu Gln Ala Ser
            825                 830                 835 ctg cct aag gcc cag taaggggcaa gtcctgattg tacagagcat ttcgagattt      2652
Leu Pro Lys Ala Gln
            840 atgatgtaca tgtttatgaa tgacctaggg tagggtaata cttagtaggg ttagttctaa    2712 ttcttggagt caagtattga ctcactgggc cgataaaaaa aaaaaaaaaa aaaaaaaa      2771

<210> SEQ ID NO 27
<211> LENGTH: 861
<212> TYPE: PRT
<213> ORGANISM: Aspergillus oryzae

<400> SEQUENCE: 27

Met Lys Leu Gly Trp Ile Glu Val Ala Ala Leu Ala Ala Ala Ser Val
                -15                 -10                  -5

Val Ser Ala Lys Asp Asp Leu Ala Tyr Ser Pro Pro Phe Tyr Pro Ser
         -1   1               5                  10

Pro Trp Ala Asp Gly Gln Gly Glu Trp Ala Glu Val Tyr Lys Arg Ala
            15                  20                  25

Val Asp Ile Val Ser Gln Met Thr Leu Thr Glu Lys Val Asn Leu Thr
 30                  35                  40                  45

Thr Gly Thr Gly Trp Gln Leu Glu Arg Cys Val Gly Gln Thr Gly Ser
                 50                  55                  60

Val Pro Arg Leu Asn Ile Pro Ser Leu Cys Leu Gln Asp Ser Pro Leu
             65                  70                  75
```

```
Gly Ile Arg Phe Ser Asp Tyr Asn Ser Ala Phe Pro Ala Gly Val Asn
        80                  85                  90

Val Ala Ala Thr Trp Asp Lys Thr Leu Ala Tyr Leu Arg Gly Gln Ala
 95                 100                 105

Met Gly Glu Glu Phe Ser Asp Lys Gly Ile Asp Val Gln Leu Gly Pro
110                 115                 120                 125

Ala Ala Gly Pro Leu Gly Ala His Pro Asp Gly Gly Arg Asn Trp Glu
                130                 135                 140

Gly Phe Ser Pro Asp Pro Ala Leu Thr Gly Val Leu Phe Ala Glu Thr
                145                 150                 155

Ile Lys Gly Ile Gln Asp Ala Gly Val Ile Ala Thr Ala Lys His Tyr
            160                 165                 170

Ile Met Asn Glu Gln Glu His Phe Arg Gln Pro Glu Ala Ala Gly
            175                 180                 185

Tyr Gly Phe Asn Val Ser Asp Ser Leu Ser Ser Asn Val Asp Asp Lys
190                 195                 200                 205

Thr Met His Glu Leu Tyr Leu Trp Pro Phe Ala Asp Ala Val Arg Ala
                210                 215                 220

Gly Val Gly Ala Val Met Cys Ser Tyr Asn Gln Ile Asn Asn Ser Tyr
                225                 230                 235

Gly Cys Glu Asn Ser Glu Thr Leu Asn Lys Leu Leu Lys Ala Glu Leu
                240                 245                 250

Gly Phe Gln Gly Phe Val Met Ser Asp Trp Thr Ala His His Ser Gly
                255                 260                 265

Val Gly Ala Ala Leu Ala Gly Leu Asp Met Ser Met Pro Gly Asp Val
270                 275                 280                 285

Thr Phe Asp Ser Gly Thr Ser Phe Trp Gly Ala Asn Leu Thr Val Gly
                290                 295                 300

Val Leu Asn Gly Thr Ile Pro Gln Trp Arg Val Asp Asp Met Ala Val
                305                 310                 315

Arg Ile Met Ala Ala Tyr Tyr Lys Val Gly Arg Asp Thr Lys Tyr Thr
            320                 325                 330

Pro Pro Asn Phe Ser Ser Trp Thr Arg Asp Glu Tyr Gly Phe Ala His
            335                 340                 345

Asn His Val Ser Glu Gly Ala Tyr Glu Arg Val Asn Glu Phe Val Asp
350                 355                 360                 365

Val Gln Arg Asp His Ala Asp Leu Ile Arg Arg Ile Gly Ala Gln Ser
                370                 375                 380

Thr Val Leu Leu Lys Asn Lys Gly Ala Leu Pro Leu Ser Arg Lys Glu
            385                 390                 395

Lys Leu Val Ala Leu Leu Gly Glu Asp Ala Gly Ser Asn Ser Trp Gly
                400                 405                 410

Ala Asn Gly Cys Asp Asp Arg Gly Cys Asp Asn Gly Thr Leu Ala Met
            415                 420                 425

Ala Trp Gly Ser Gly Thr Ala Asn Phe Pro Tyr Leu Val Thr Pro Glu
430                 435                 440                 445

Gln Ala Ile Gln Asn Glu Val Leu Gln Gly Arg Gly Asn Val Phe Ala
                450                 455                 460

Val Thr Asp Ser Trp Ala Leu Asp Lys Ile Ala Ala Ala Arg Gln
                465                 470                 475

Ala Ser Val Ser Leu Val Phe Val Asn Ser Asp Ser Gly Glu Ser Tyr
            480                 485                 490
```

```
Leu Ser Val Asp Gly Asn Glu Gly Asp Arg Asn Asn Ile Thr Leu Trp
    495                 500                 505

Lys Asn Gly Asp Asn Val Val Lys Thr Ala Ala Asn Asn Cys Asn Asn
510                 515                 520                 525

Thr Val Val Ile Ile His Ser Val Gly Pro Val Leu Ile Asp Glu Trp
                530                 535                 540

Tyr Asp His Pro Asn Val Thr Gly Ile Leu Trp Ala Gly Leu Pro Gly
            545                 550                 555

Gln Glu Ser Gly Asn Ser Ile Ala Asp Val Leu Tyr Gly Arg Val Asn
        560                 565                 570

Pro Gly Ala Lys Ser Pro Phe Thr Trp Gly Lys Thr Arg Glu Ser Tyr
    575                 580                 585

Gly Ser Pro Leu Val Lys Asp Ala Asn Asn Gly Asn Gly Ala Pro Gln
590                 595                 600                 605

Ser Asp Phe Thr Gln Gly Val Phe Ile Asp Tyr Arg His Phe Asp Lys
                610                 615                 620

Phe Asn Glu Thr Pro Ile Tyr Glu Phe Gly Tyr Gly Leu Ser Tyr Thr
            625                 630                 635

Thr Phe Glu Leu Ser Asp Leu His Val Gln Pro Leu Asn Ala Ser Arg
        640                 645                 650

Tyr Thr Pro Thr Ser Gly Met Thr Glu Ala Ala Lys Asn Phe Gly Glu
    655                 660                 665

Ile Gly Asp Ala Ser Glu Tyr Val Tyr Pro Glu Gly Leu Glu Arg Ile
670                 675                 680                 685

His Glu Phe Ile Tyr Pro Trp Ile Asn Ser Thr Asp Leu Lys Ala Ser
                690                 695                 700

Ser Asp Asp Ser Asn Tyr Gly Trp Glu Asp Ser Lys Tyr Ile Pro Glu
            705                 710                 715

Gly Ala Thr Asp Gly Ser Ala Gln Pro Arg Leu Pro Ala Ser Gly Gly
        720                 725                 730

Ala Gly Gly Asn Pro Gly Leu Tyr Glu Asp Leu Phe Arg Val Ser Val
    735                 740                 745

Lys Val Lys Asn Thr Gly Asn Val Ala Gly Asp Glu Val Pro Gln Leu
750                 755                 760                 765

Tyr Val Ser Leu Gly Gly Pro Asn Glu Pro Lys Val Val Leu Arg Lys
                770                 775                 780

Phe Glu Arg Ile His Leu Ala Pro Ser Gln Glu Ala Val Trp Thr Thr
            785                 790                 795

Thr Leu Thr Arg Arg Asp Leu Ala Asn Trp Asp Val Ser Ala Gln Asp
        800                 805                 810

Trp Thr Val Thr Pro Tyr Pro Lys Thr Ile Tyr Val Gly Asn Ser Ser
    815                 820                 825

Arg Lys Leu Pro Leu Gln Ala Ser Leu Pro Lys Ala Gln
830                 835                 840

<210> SEQ ID NO 28
<211> LENGTH: 46
<212> TYPE: DNA
<213> ORGANISM: Aspergillus oryzae

<400> SEQUENCE: 28
atagtcaacc gcggactgcg catcatgaag cttggttgga tcgagg                46
```

```
<210> SEQ ID NO 29
<211> LENGTH: 26
<212> TYPE: DNA
<213> ORGANISM: Aspergillus oryzae

<400> SEQUENCE: 29
actagtttac tgggccttag gcagcg                                    26

<210> SEQ ID NO 30
<211> LENGTH: 26
<212> TYPE: DNA
<213> ORGANISM: Aspergillus oryzae

<400> SEQUENCE: 30
gtcgactcga agcccgaatg taggat                                    26

<210> SEQ ID NO 31
<211> LENGTH: 45
<212> TYPE: DNA
<213> ORGANISM: Aspergillus oryzae

<400> SEQUENCE: 31
cctcgatcca accaagcttc atgatgcgca gtccgcggtt gacta               45

<210> SEQ ID NO 32
<211> LENGTH: 57
<212> TYPE: DNA
<213> ORGANISM: Aspergillus oryzae

<400> SEQUENCE: 32
atgaagcttg gttggatcga ggtggccgca ttggcggctg cccctcagta gcagtgc   57

<210> SEQ ID NO 33
<211> LENGTH: 19
<212> TYPE: PRT
<213> ORGANISM: Aspergillus oryzae

<400> SEQUENCE: 33

Met Lys Leu Gly Trp Ile Glu Val Ala Ala Leu Ala Ala Ala Ser Val
1               5                   10                  15

Val Ser Ala

<210> SEQ ID NO 34
<211> LENGTH: 42
<212> TYPE: DNA
<213> ORGANISM: Aspergillus oryzae

<400> SEQUENCE: 34
tgccggtgtt ggcccttgcc aaggatgatc tcgcgtactc cc                  42

<210> SEQ ID NO 35
<211> LENGTH: 28
<212> TYPE: DNA
<213> ORGANISM: Aspergillus oryzae

<400> SEQUENCE: 35
gactagtctt actgggcctt aggcagcg                                  28

<210> SEQ ID NO 36
<211> LENGTH: 63
<212> TYPE: DNA
<213> ORGANISM: Humicola insolens
```

```
-continued

<400> SEQUENCE: 36
atgcgttcct cccccctcct ccgctccgcc gttgtggccg ccctgccggt gttggccctt    60
gcc                                                                 63

<210> SEQ ID NO 37
<211> LENGTH: 21
<212> TYPE: PRT
<213> ORGANISM: Humicola insolens

<400> SEQUENCE: 37

Met Arg Ser Ser Pro Leu Leu Arg Ser Ala Val Val Ala Ala Leu Pro
1               5                   10                  15

Val Leu Ala Leu Ala
            20

<210> SEQ ID NO 38
<211> LENGTH: 30
<212> TYPE: DNA
<213> ORGANISM: Aspergillus oryzae

<400> SEQUENCE: 38
acgcgtcgac cgaatgtagg attgttatcc                                    30

<210> SEQ ID NO 39
<211> LENGTH: 42
<212> TYPE: DNA
<213> ORGANISM: Aspergillus oryzae

<400> SEQUENCE: 39
gggagtacgc gagatcatcc ttggcaaggg ccaacaccgg ca                      42
```